(12) United States Patent
Jung et al.

(10) Patent No.: US 11,374,177 B2
(45) Date of Patent: Jun. 28, 2022

(54) COMPOUND AND ORGANIC LIGHT EMITTING DEVICE COMPRISING THE SAME

(71) Applicant: SOULBRAIN CO., LTD., Seongnam-si (KR)

(72) Inventors: Kwang Ju Jung, Seongnam-si (KR); Sung Soo Kim, Seongnam-si (KR); Hyun Young Yoo, Seongnam-si (KR); Jong Jin Ha, Seongnam-si (KR); Seok Jong Lee, Seongnam-si (KR); Chun Young Lee, Seongnam-si (KR)

(*) Notice: Subject to any disclaimer, the term of this patent is extended or adjusted under 35 U.S.C. 154(b) by 433 days.

(21) Appl. No.: 16/676,441

(22) Filed: Nov. 7, 2019

(65) Prior Publication Data

US 2020/0235309 A1    Jul. 23, 2020

Related U.S. Application Data

(63) Continuation of application No. PCT/KR2019/006482, filed on May 30, 2019.

(30) Foreign Application Priority Data

Jan. 23, 2019  (KR) .................. 10-2019-0008873
Apr. 12, 2019  (KR) .................. 10-2019-0043217

(51) Int. Cl.
  C07D 403/10       (2006.01)
  C07D 405/14       (2006.01)
  (Continued)

(52) U.S. Cl.
  CPC ........ H01L 51/0067 (2013.01); C07D 403/10 (2013.01); C07D 405/14 (2013.01);
  (Continued)

(58) Field of Classification Search
  CPC . C07D 403/10; C07D 405/14; H01L 51/0067; H01L 51/0072; H01L 51/0073;
  (Continued)

(56) References Cited

FOREIGN PATENT DOCUMENTS

CN    105308035 A    2/2016
CN    108352449 A    7/2018
(Continued)

*Primary Examiner* — Vu A Nguyen
(74) *Attorney, Agent, or Firm* — Jongkook Park

(57) ABSTRACT

Provided are a compound represented by the following Chemical Formulas and an organic light emitting device comprising the same.

(Continued)

-continued
2
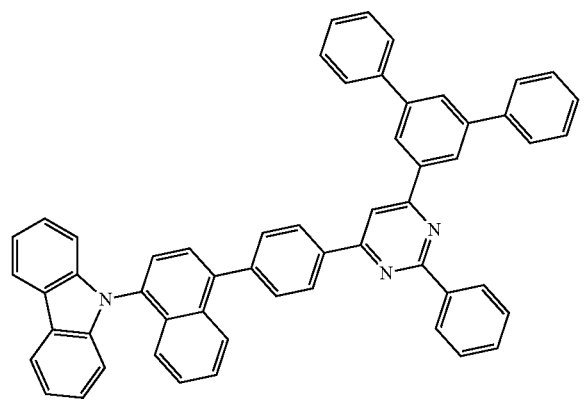
5
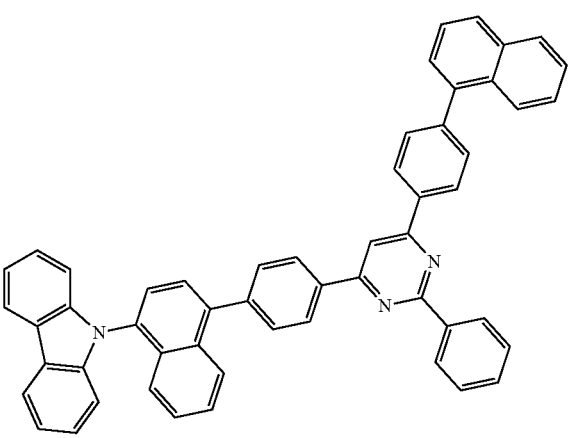
3
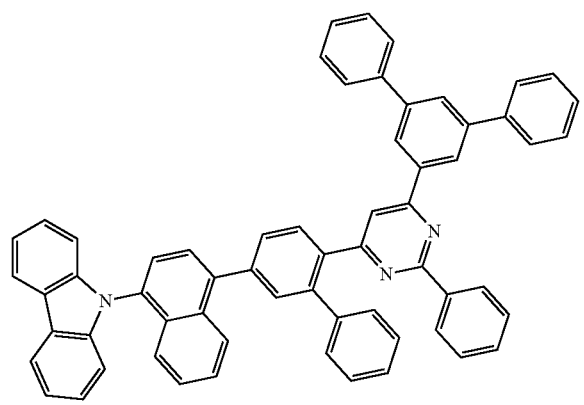
4
6
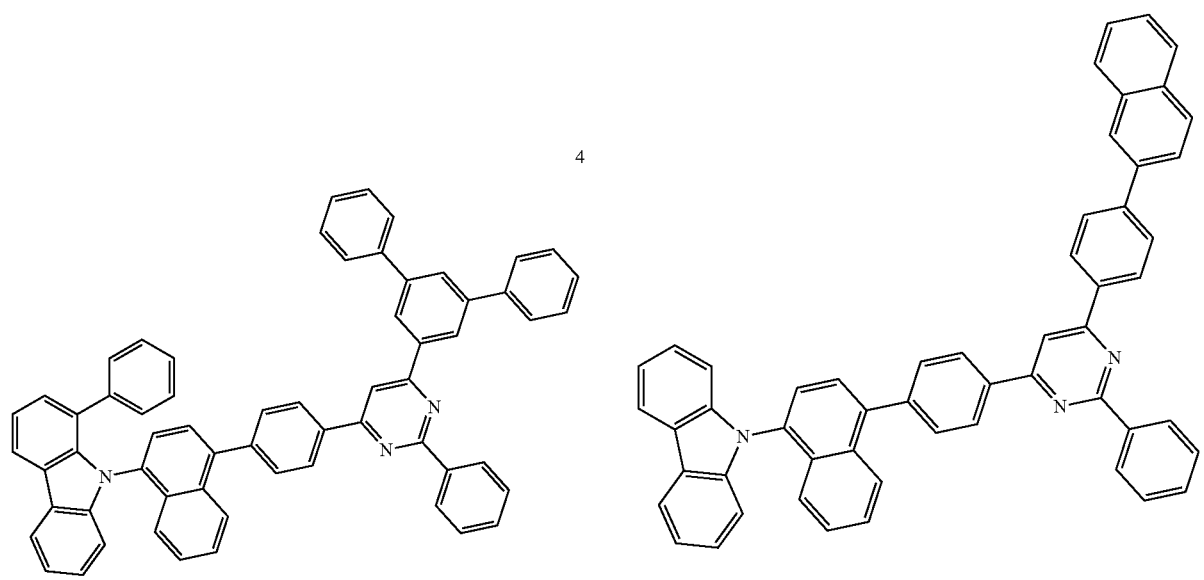

-continued
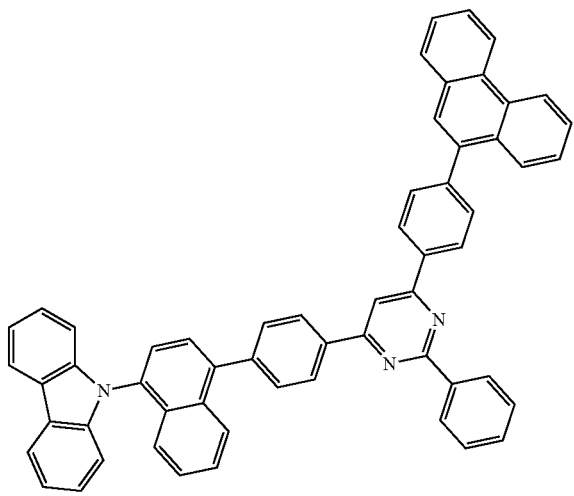
7
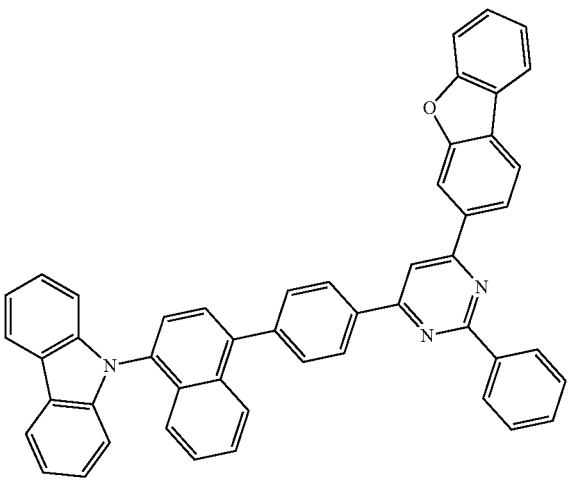
9
9 Claims, 40 Drawing Sheets
(51) Int. Cl.
*H01L 51/00* (2006.01)
*H01L 51/50* (2006.01)
*H01L 51/56* (2006.01)
(52) U.S. Cl.
CPC ...... *H01L 51/0072* (2013.01); *H01L 51/0073* (2013.01); *H01L 51/001* (2013.01); *H01L 51/5004* (2013.01); *H01L 51/5012* (2013.01); *H01L 51/5056* (2013.01); *H01L 51/5072* (2013.01); *H01L 51/5092* (2013.01); *H01L 51/56* (2013.01); *H01L 2251/552* (2013.01); *H01L 2251/558* (2013.01)
(58) Field of Classification Search
CPC ............. H01L 51/5012; H01L 51/5056; H01L 51/5072; H01L 51/5092
See application file for complete search history.
(56) References Cited
FOREIGN PATENT DOCUMENTS
| EP | 3202872 A1 | 8/2017 |
|---|---|---|
| EP | 3373353 A1 | 9/2018 |
| KR | 1020140006708 A | 1/2014 |
| WO | 2016052819 A1 | 4/2016 |
8

COMPOUND AND ORGANIC LIGHT EMITTING DEVICE COMPRISING THE SAME

CROSS-REFERENCE TO RELATED APPLICATIONS

This application claims priority under 35 U.S.C. § 119 to Korean Patent Application No. 10-2019-0008873, filed on Jan. 23, 2019, and Korean Patent Application No. 10-2019-0043217, filed on Apr. 12, 2019, in the Korean Intellectual Property Office, the disclosures of which are incorporated herein by reference in their entirety.

TECHNICAL FIELD

The following disclosure relates to a compound and an organic light emitting device comprising the same.

BACKGROUND

Organic light emitting diodes (OLEDs) are self-emitting devices that have advantages of not only wide viewing angle and excellent contrast, but also fast response time, excellent luminance, driving voltage and response speed, and multi-color capability. In general, an organic light emitting diode may include an anode and a cathode, and an organic layer interposed between the anode and the cathode. The organic layer may comprise a hole injection layer, a hole transport layer, a light emitting layer, an electron transport layer, an electron injection layer, and the like. When a voltage is applied between the anode and the cathode, holes injected from the anode move to the light emitting layer via the hole transport layer, and electrons injected from the cathode move to the light emitting layer via the electron transport layer. Carriers such as holes and electrons recombine in the region of the light emitting layer to generate excitons, and light is generated as the excitons move to a ground state. Generally, in view of probability, of the excitons generated when driving the organic light emitting diodes, 25% are generated in singlet states and 75% are generated in triplet states. In the case of a fluorescent light emitting material, light is only emitted by the 25% of excitons generated in the singlet state, and thus the internal quantum efficiency remains at a maximum of 25%. In order to improve these characteristics, iridium or platinum complexes that are capable of utilizing the energy of triplets are employed, and these complexes are known to have excellent quantum efficiency characteristics. However, these materials are expensive, and have limitations in their application due to causing instability of blue light emitting materials.

SUMMARY

An embodiment of the present disclosure is directed to providing a compound having excellent electrochemical and thermal stability to achieve excellent lifetime characteristics and high luminous efficiency even at a low driving voltage, and an organic light emitting device comprising the same.

In one aspect, the present disclosure provides a compound comprising one or more selected from the group consisting of Chemical Formulas 1 to 9 as follows:

[Chemical Formula 1]

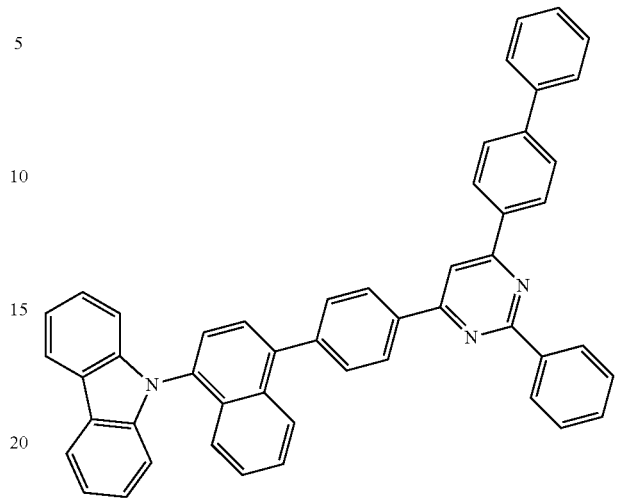

[Chemical Formula 2]

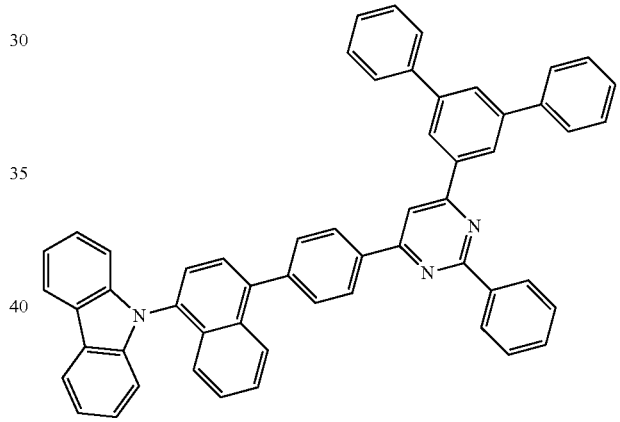

[Chemical Formula 3]

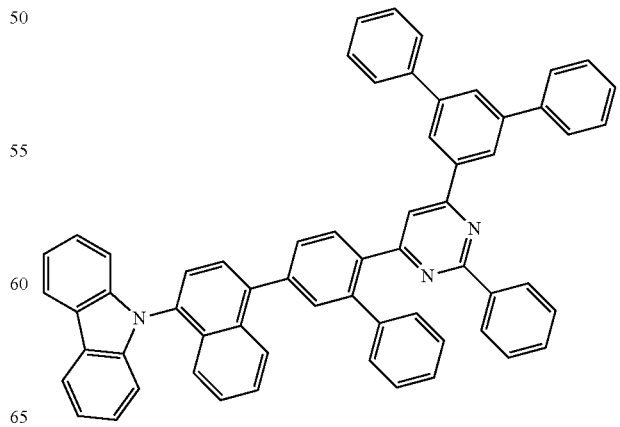

[Chemical Formula 4]
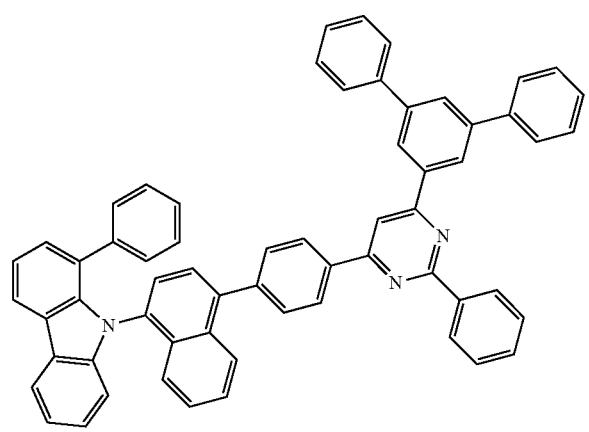
[Chemical Formula 5]
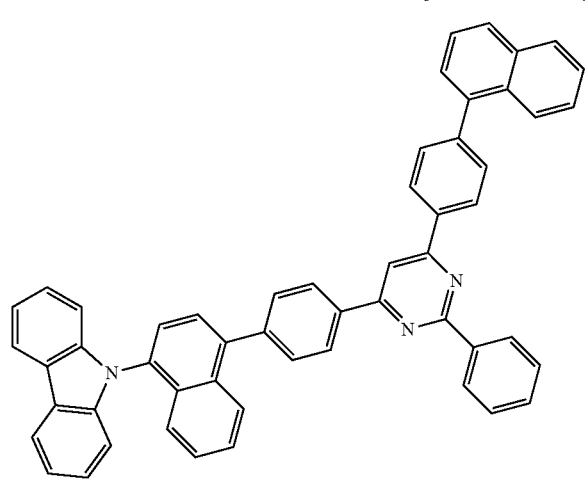
[Chemical Formula 6]
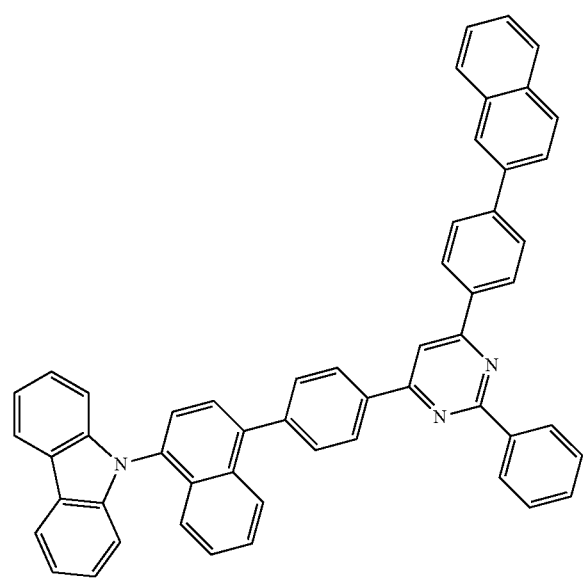
[Chemical Formula 7]
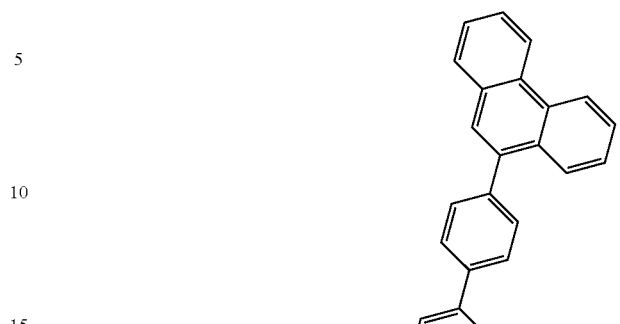
[Chemical Formula 8]
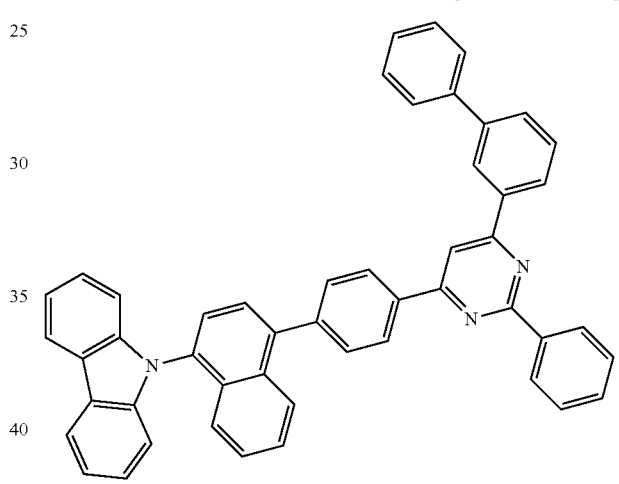
[Chemical Formula 9]
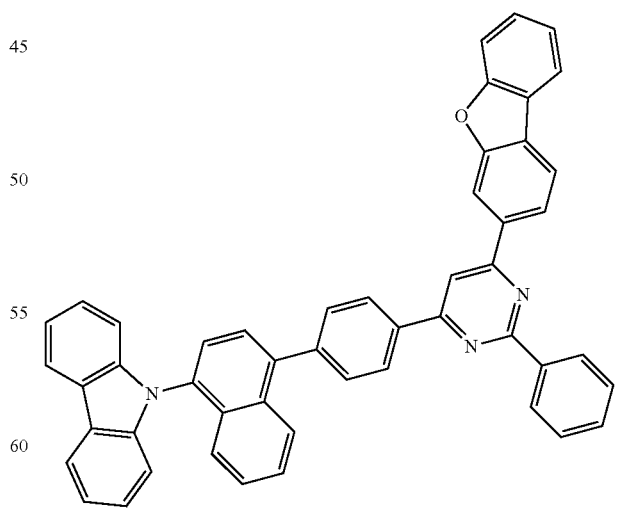
In another aspect, the present disclosure provides a material for use in an organic light emitting device comprising the compound described above.

In yet another aspect, the present disclosure provides an organic light emitting device comprising the compound above.

In still another aspect, the present disclosure provides electronic equipment comprising the organic light emitting device above.

DETAILED DESCRIPTION OF EMBODIMENTS

Figure 1:
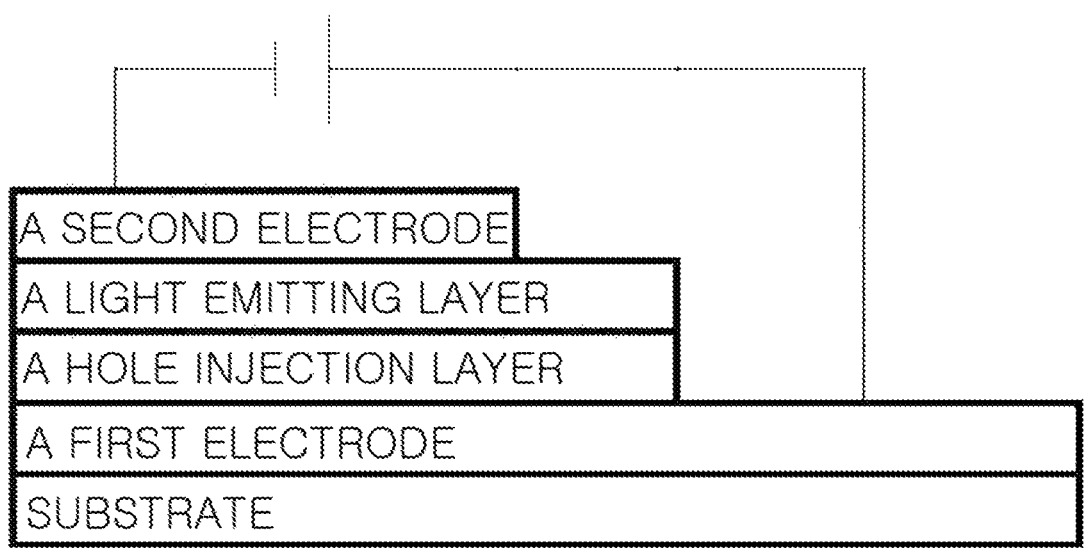
FIG. 1 schematically illustrates a stacked structure of an organic light emitting device according to an embodiment of the present disclosure.
Figure 2A:
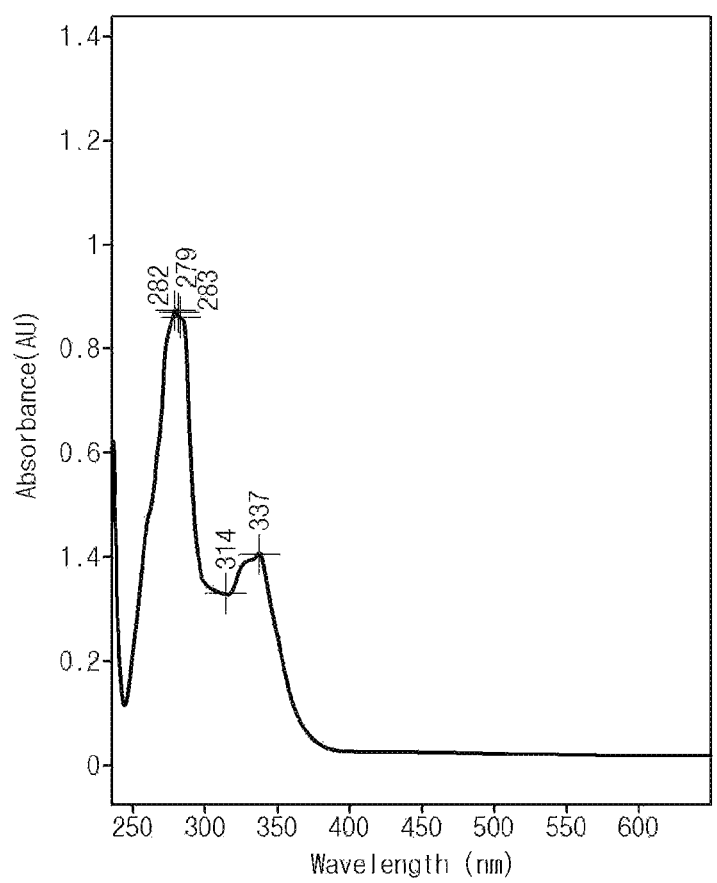
FIGS. 2A, 2B, and 2C illustrate the UV-Vis spectrum, the photoluminescence (PL) spectroscopy results, and the low temperature photoluminescence (LTPL) spectroscopy results, respectively, of Compound 1 of the present disclosure.
Figure 2B:
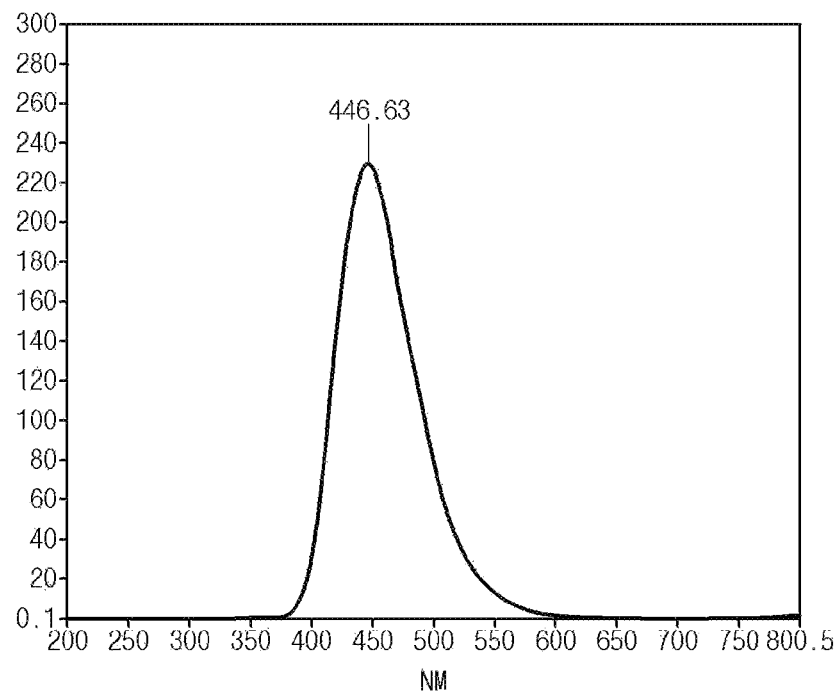
Figure 2C:
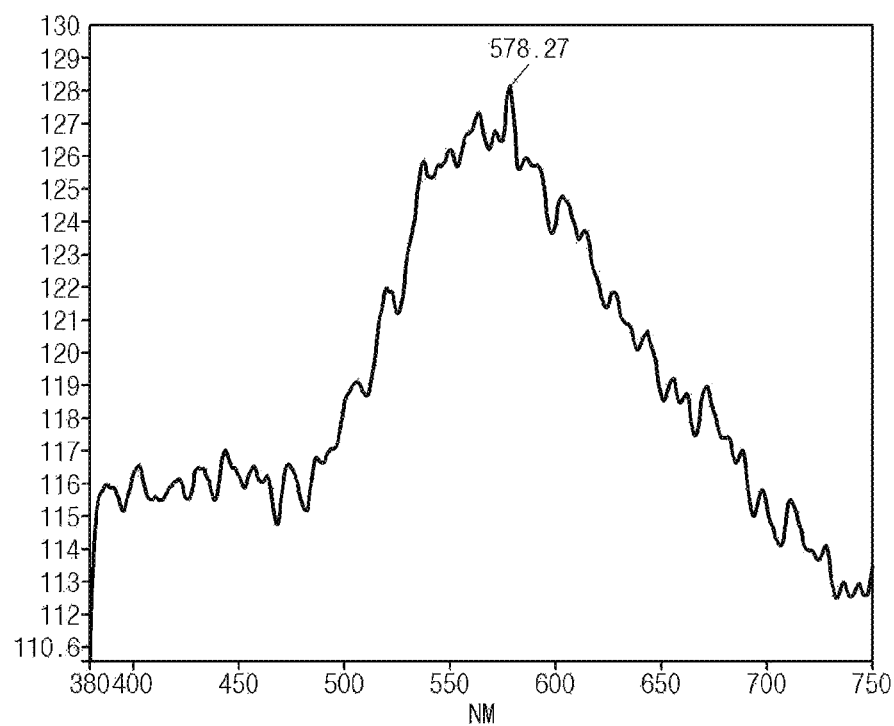
Figure 3A:
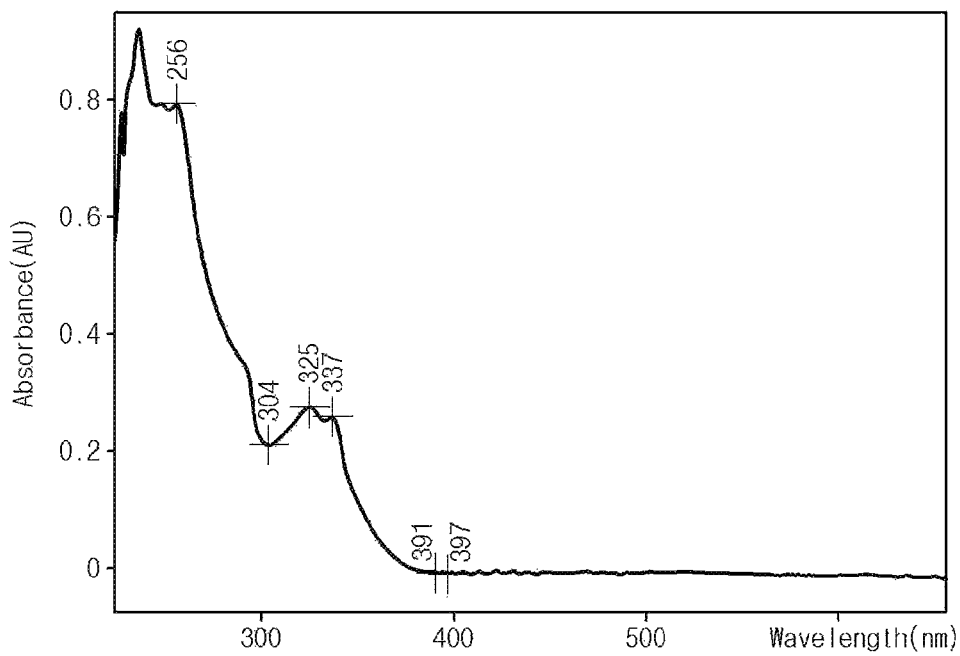
FIGS. 3A, 3B, and 3C illustrate the UV-Vis spectrum, the PL spectroscopy results, and the LTPL spectroscopy results, respectively, of Compound 2 of the present disclosure.
Figure 3B:
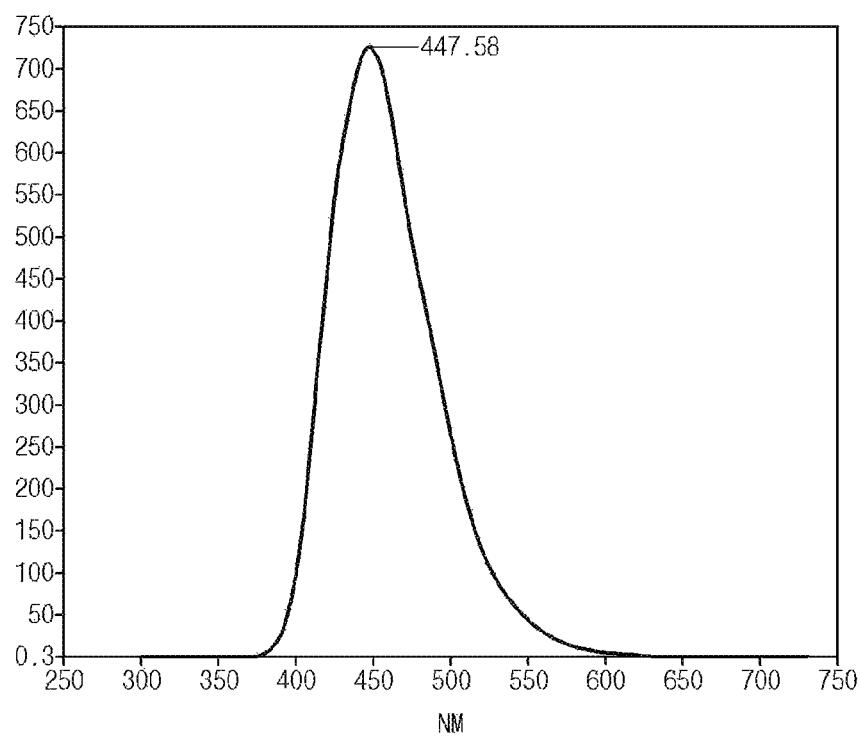
Figure 3C:
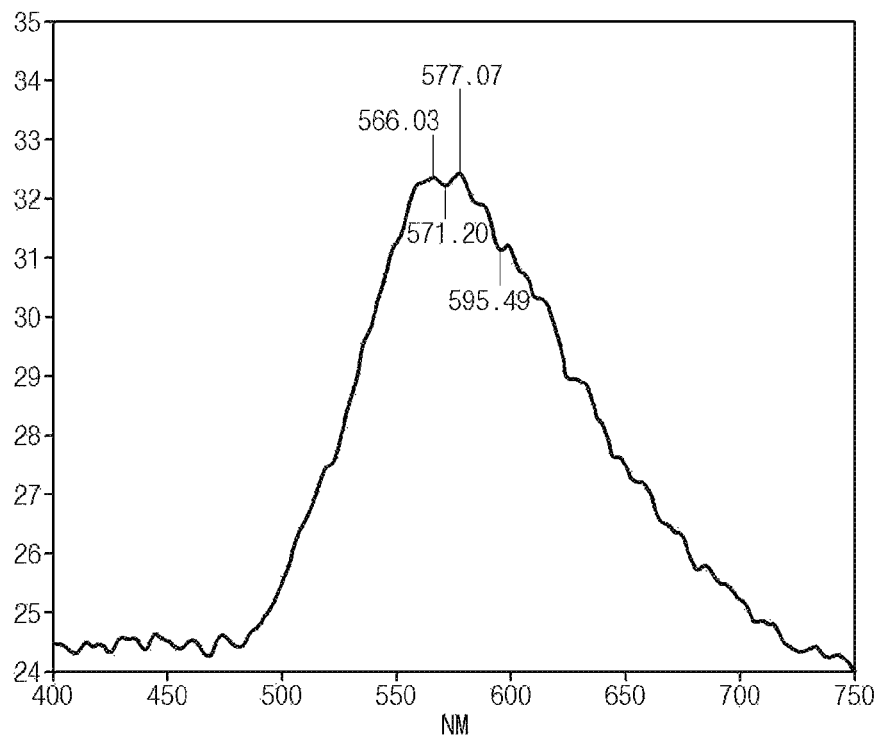
Figure 4A:
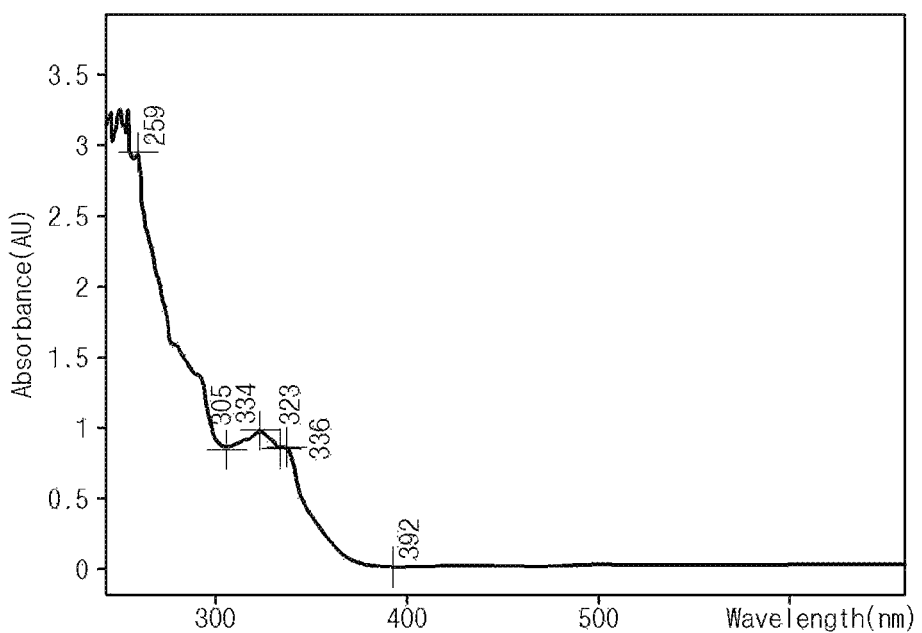
FIGS. 4A, 4B, and 4C illustrate the UV-Vis spectrum, the PL spectroscopy results, and the LTPL spectroscopy results, respectively, of Compound 3 of the present disclosure.
Figure 4B:
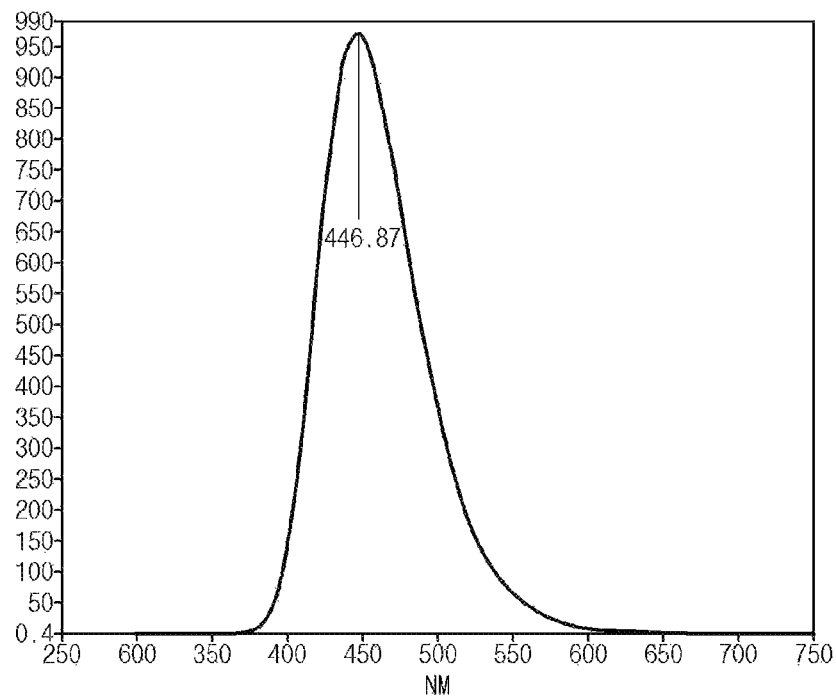
Figure 4C:
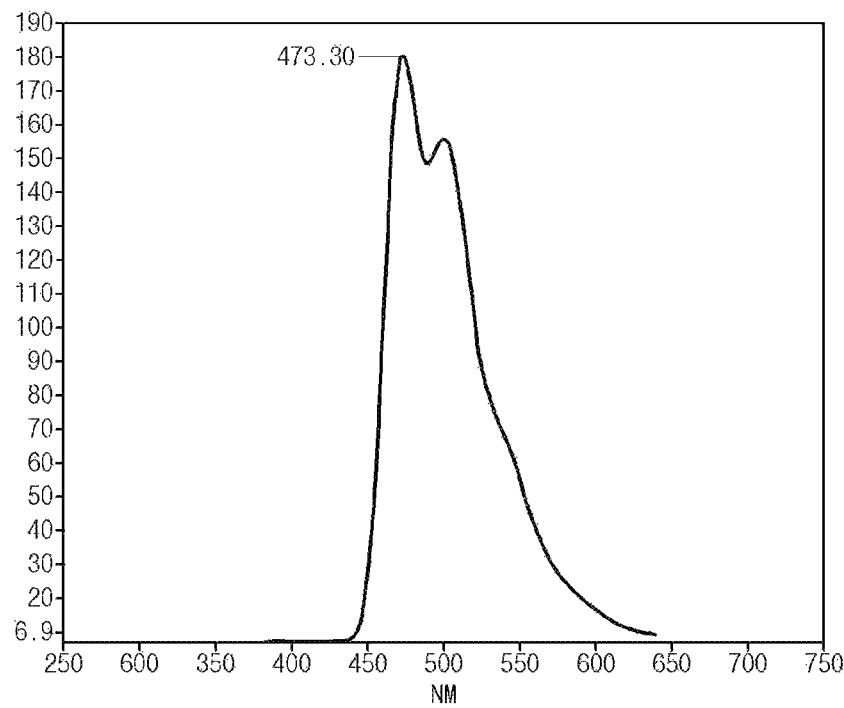
Figure 5A:
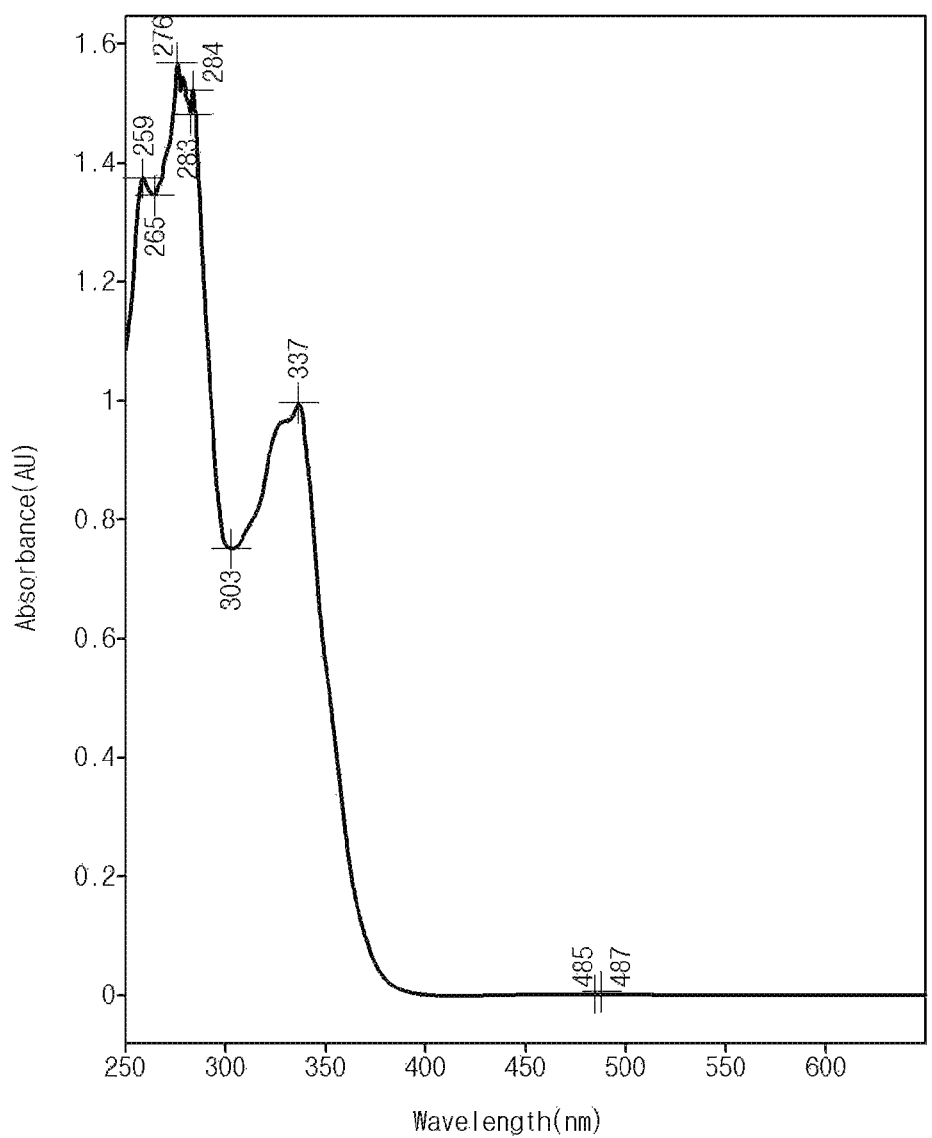
FIGS. 5A, 5B, and 5C illustrate the UV-Vis spectrum, the PL spectroscopy results, and the LTPL spectroscopy results, respectively, of Compound 5 of the present disclosure.
Figure 5B:
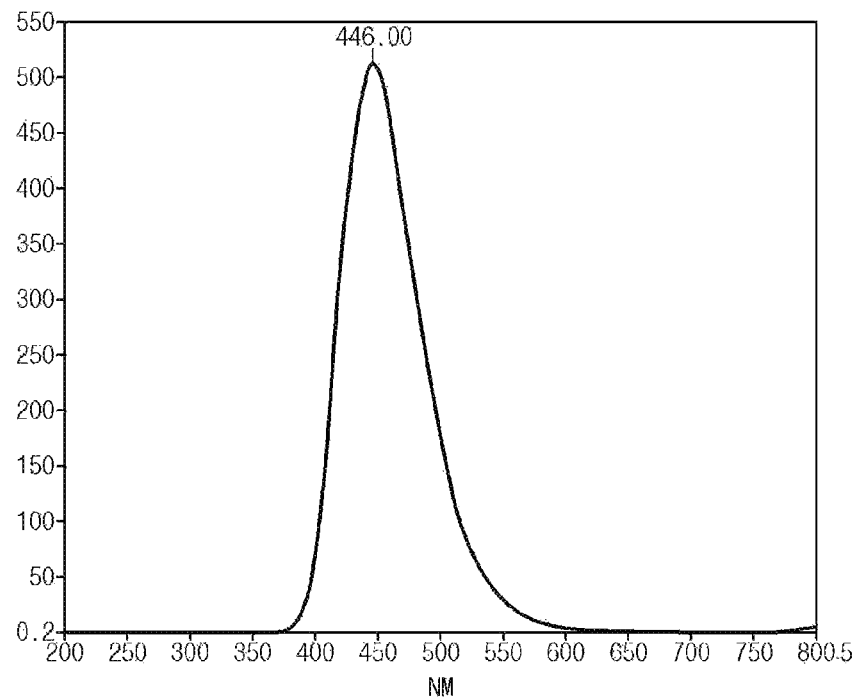
Figure 5C:
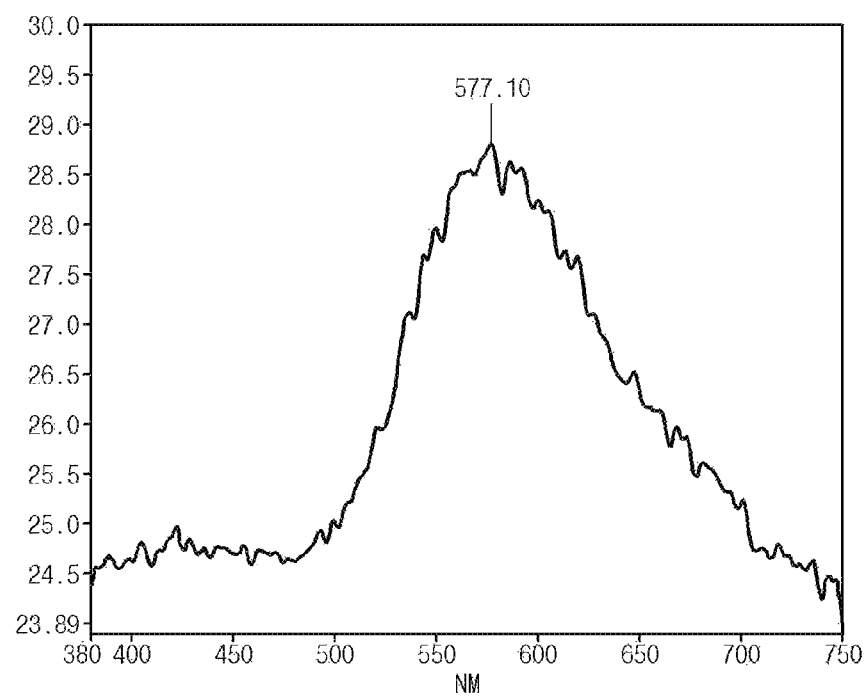
Figure 6A:
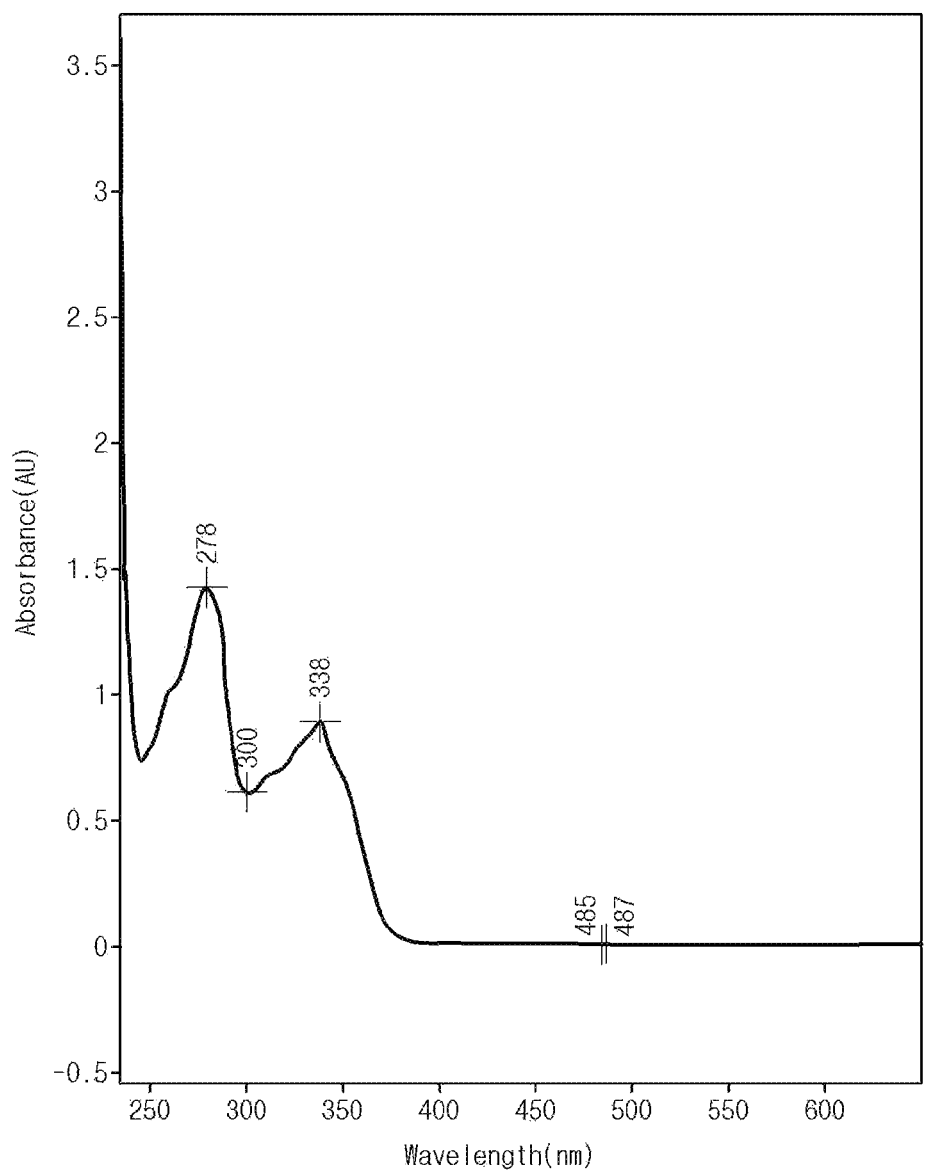
FIGS. 6A, 6B, and 6C illustrate the UV-Vis spectrum, the PL spectroscopy results, and the LTPL spectroscopy results, respectively, of Compound 6 of the present disclosure.
Figure 6B:
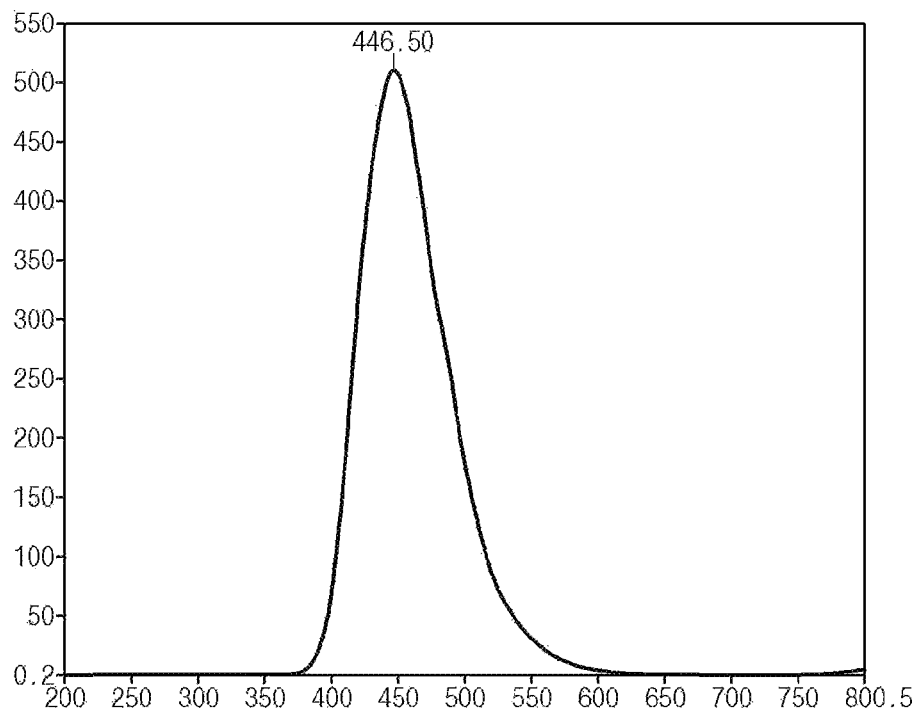
Figure 6C:
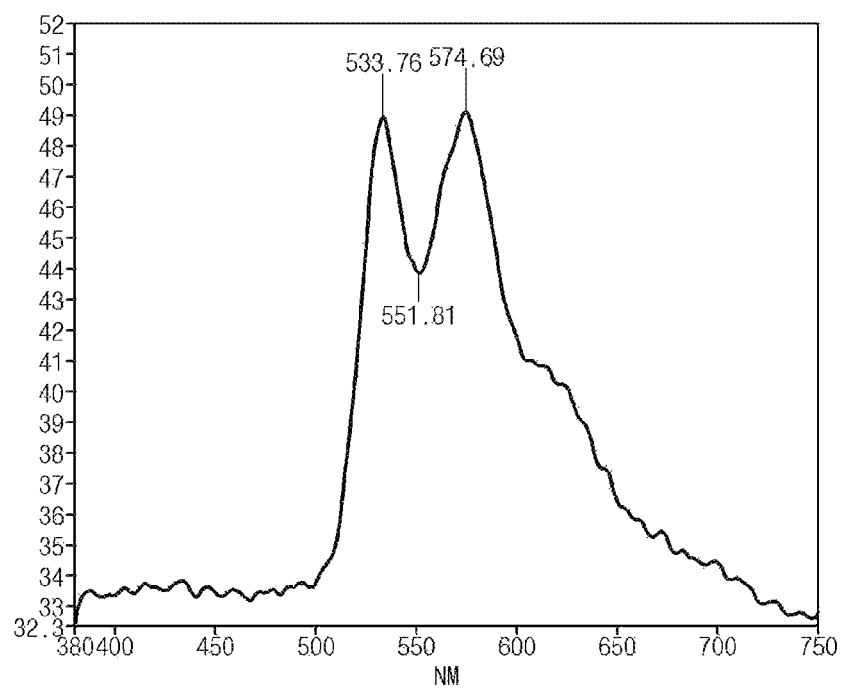
Figure 7A:
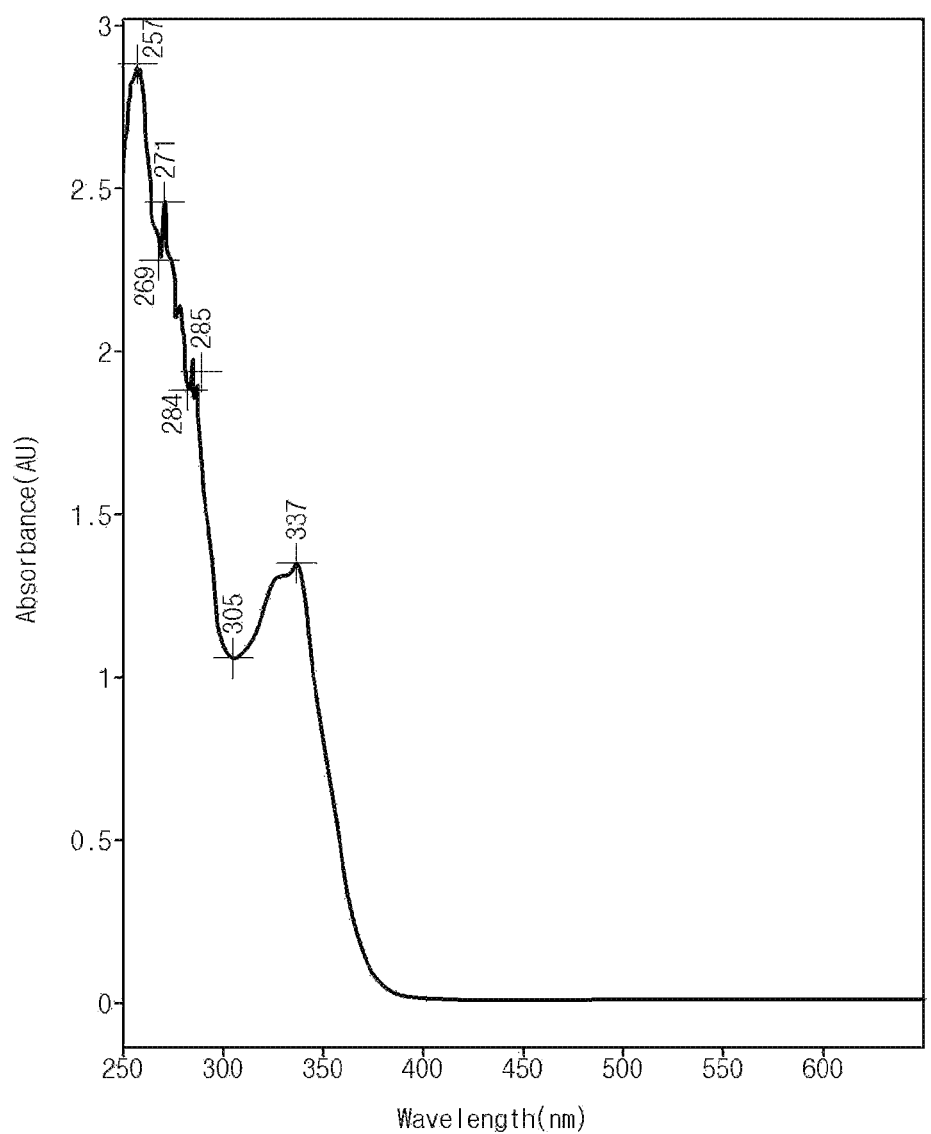
FIGS. 7A, 7B, and 7C illustrate the UV-Vis spectrum, the PL spectroscopy results, and the LTPL spectroscopy results, respectively, of Compound 7 of the present disclosure.
Figure 7B:
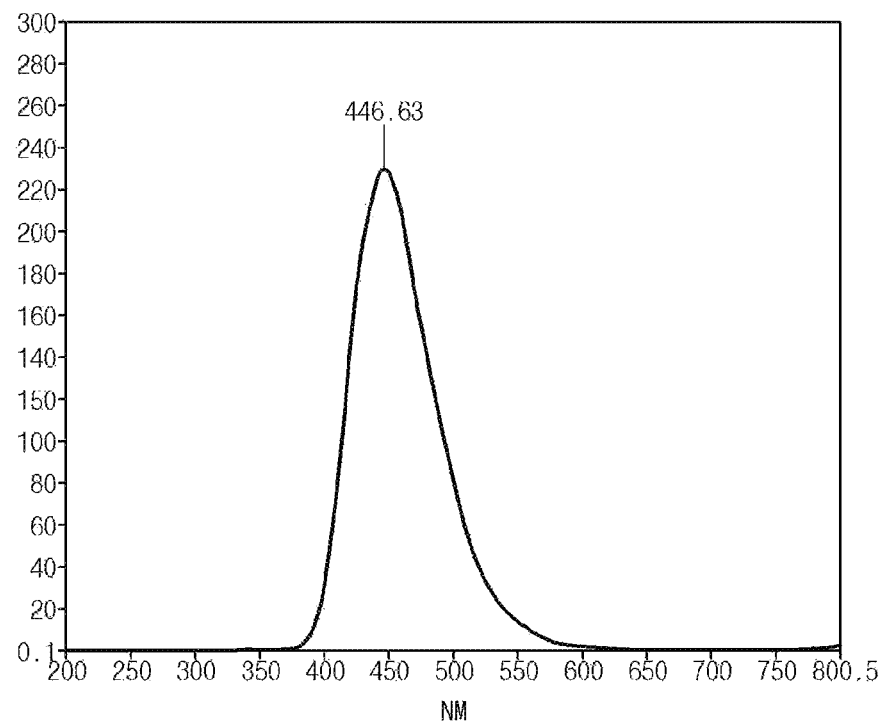
Figure 7C:
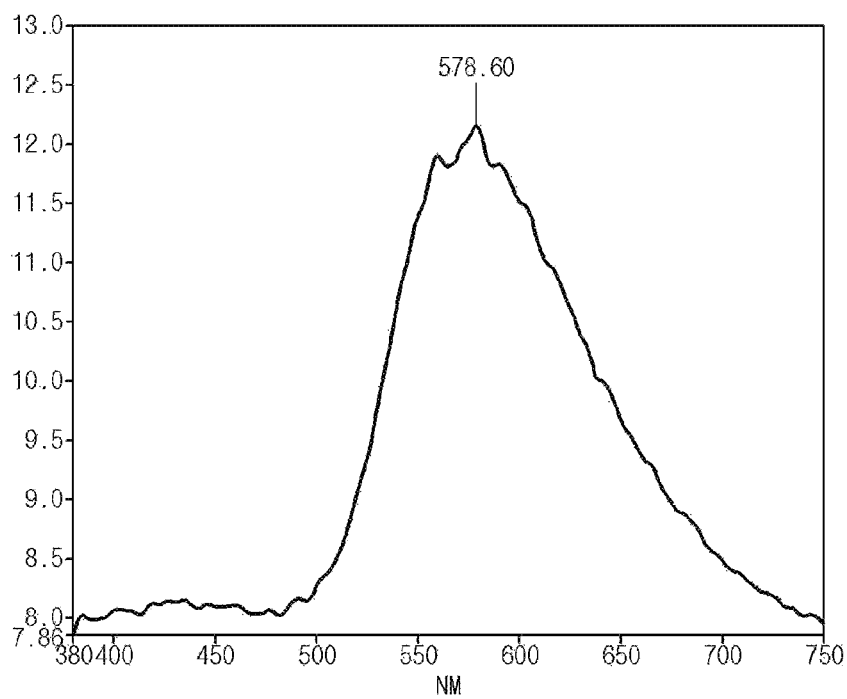
Figure 8A:
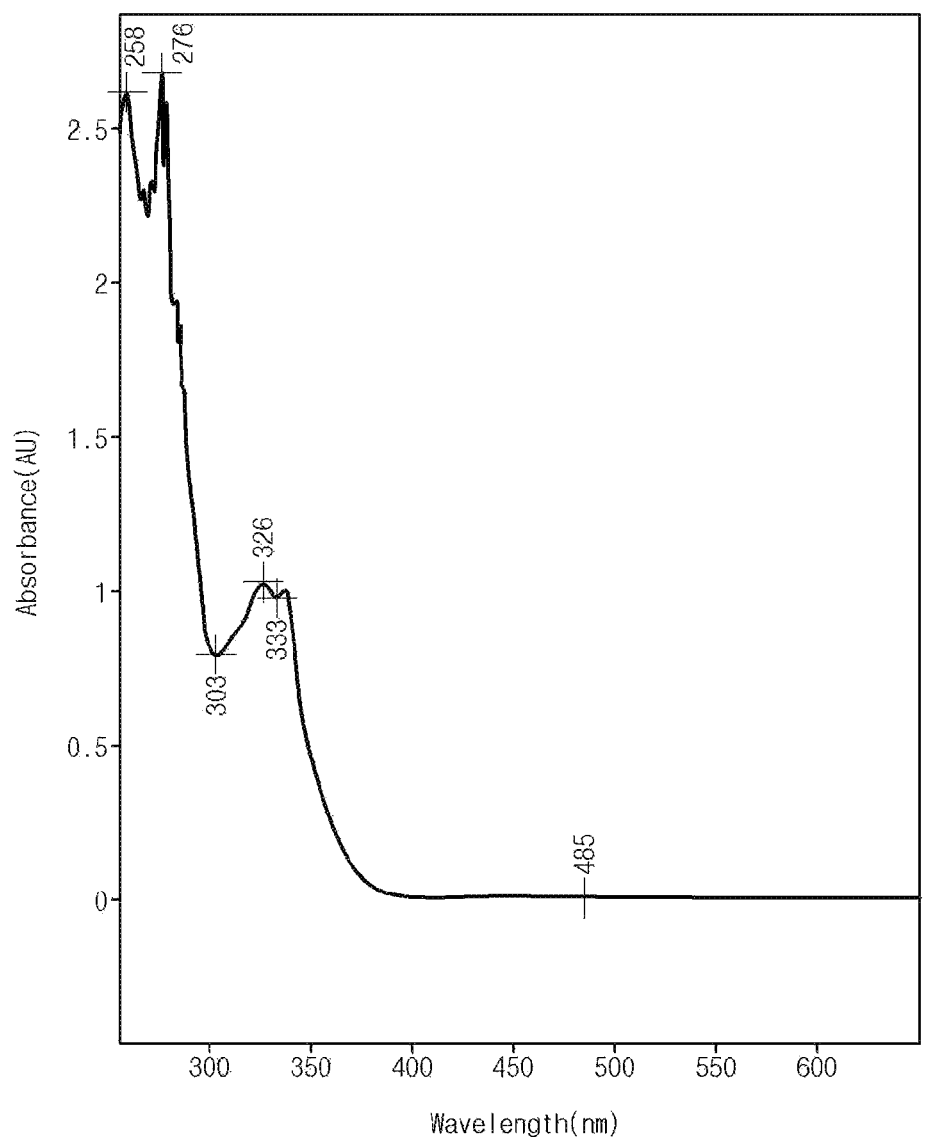
FIGS. 8A, 8B, and 8C illustrate the UV-Vis spectrum, the PL spectroscopy results, and the LTPL spectroscopy results, respectively, of Compound 8 of the present disclosure.
Figure 8B:
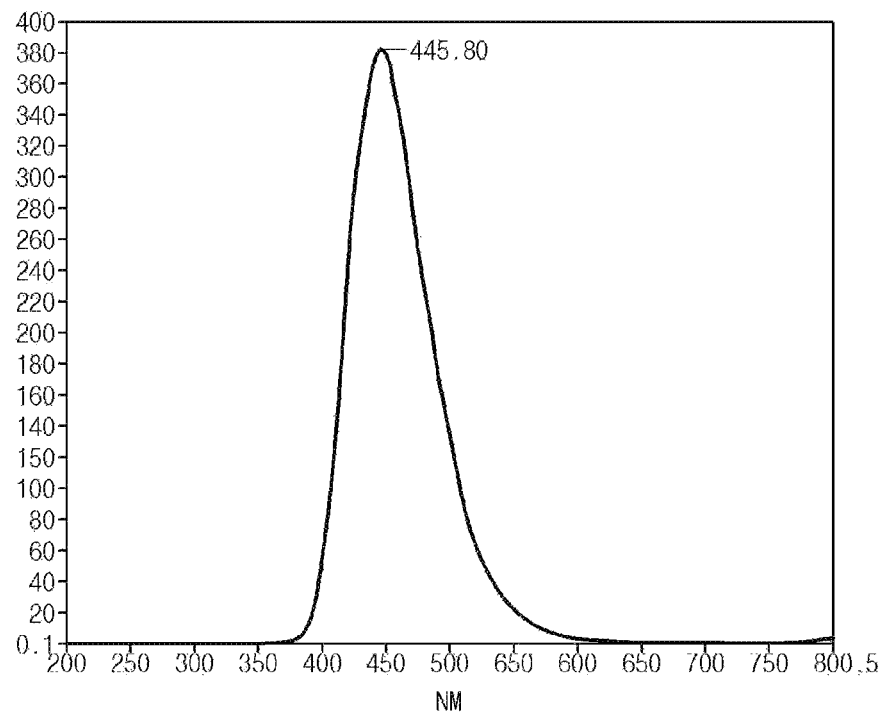
Figure 8C:
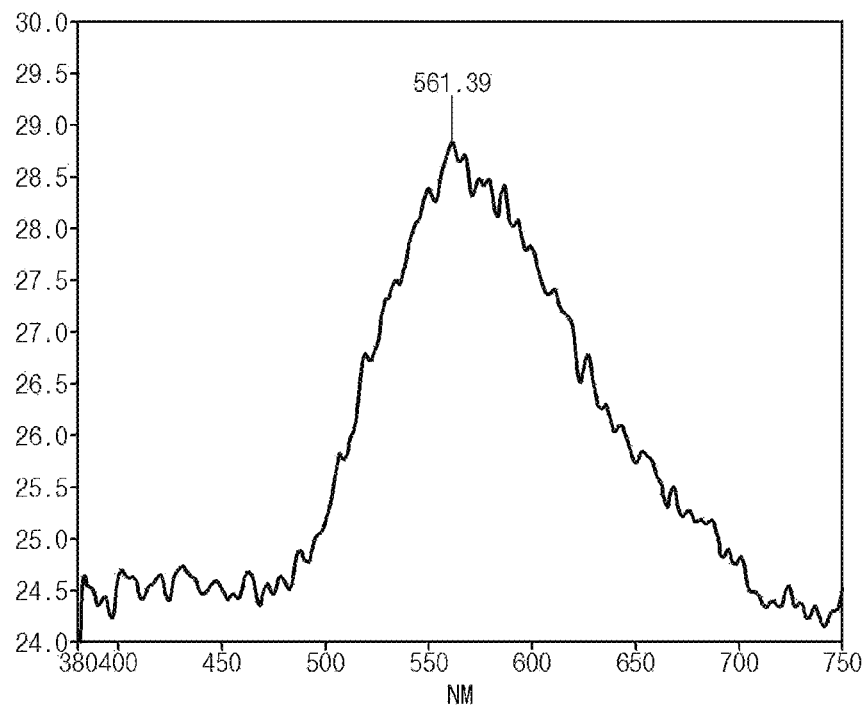
Figure 9A:
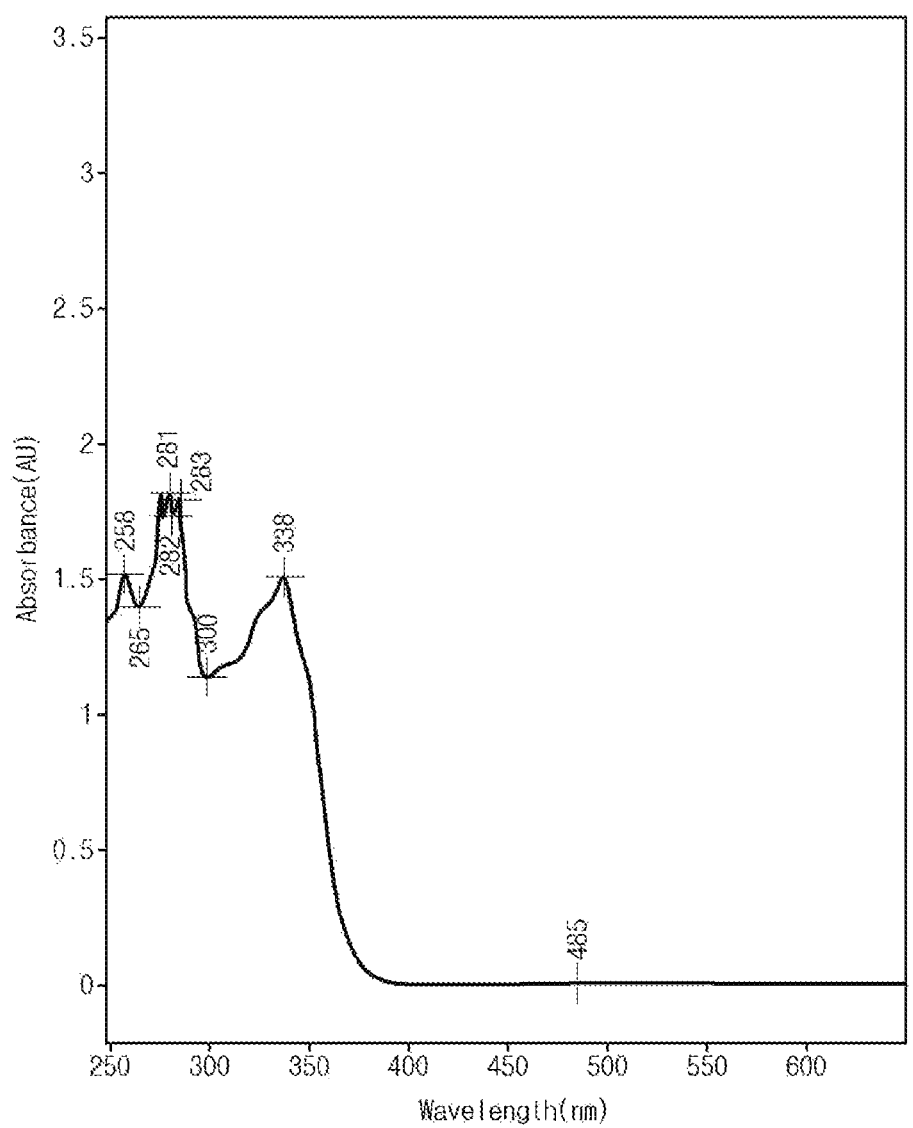
FIGS. 9A, 9B, and 9C illustrate the UV-Vis spectrum, the PL spectroscopy results, and the LTPL spectroscopy results, respectively, of Compound 9 of the present disclosure.
Figure 9B:
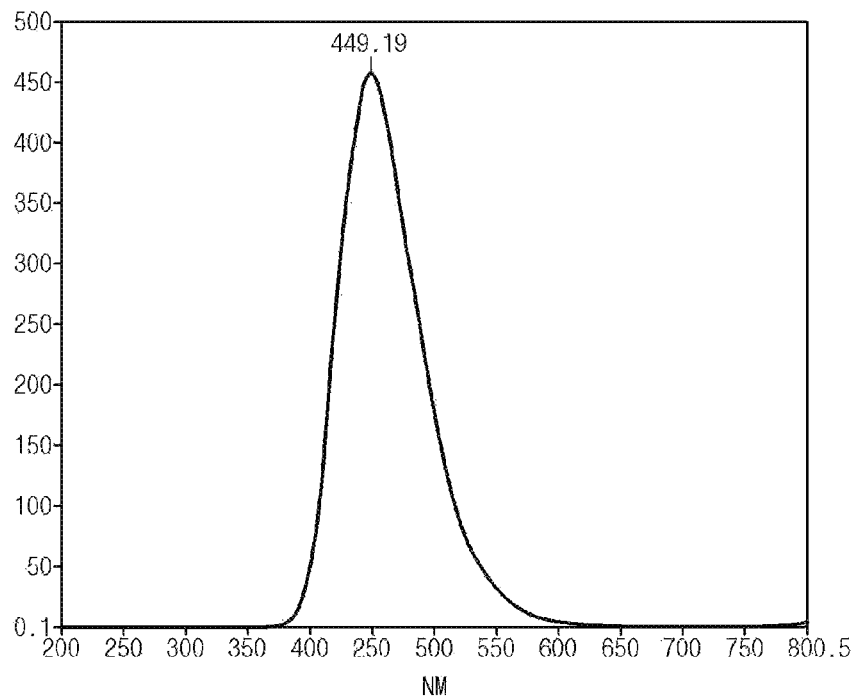
Figure 9C:
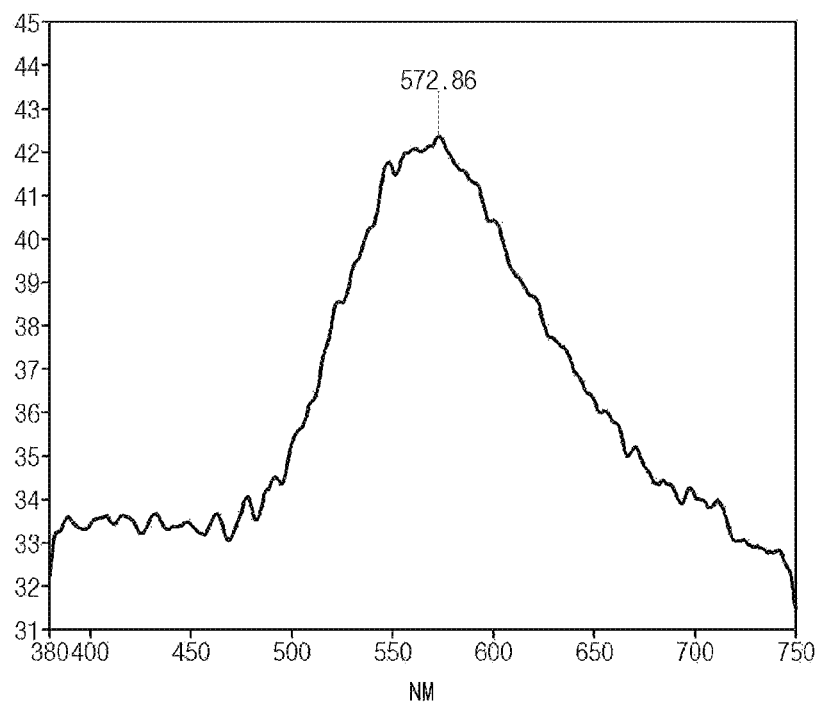
Figure 10A:
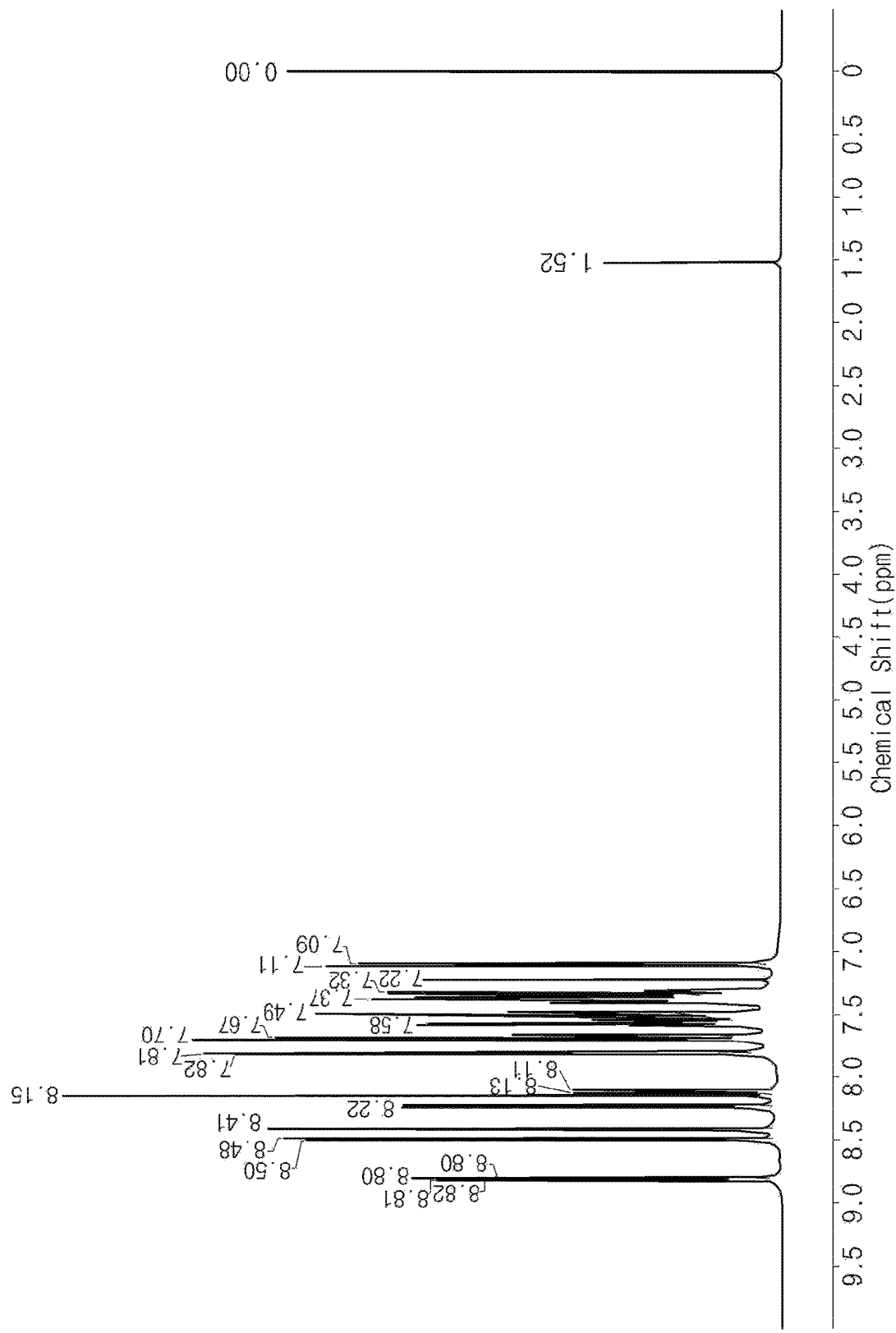
FIGS. 10A and 10B illustrate the $^1$H NMR and $^{13}$C NMR graphs, respectively, of Compound 1 of the present disclosure.
Figure 10B:
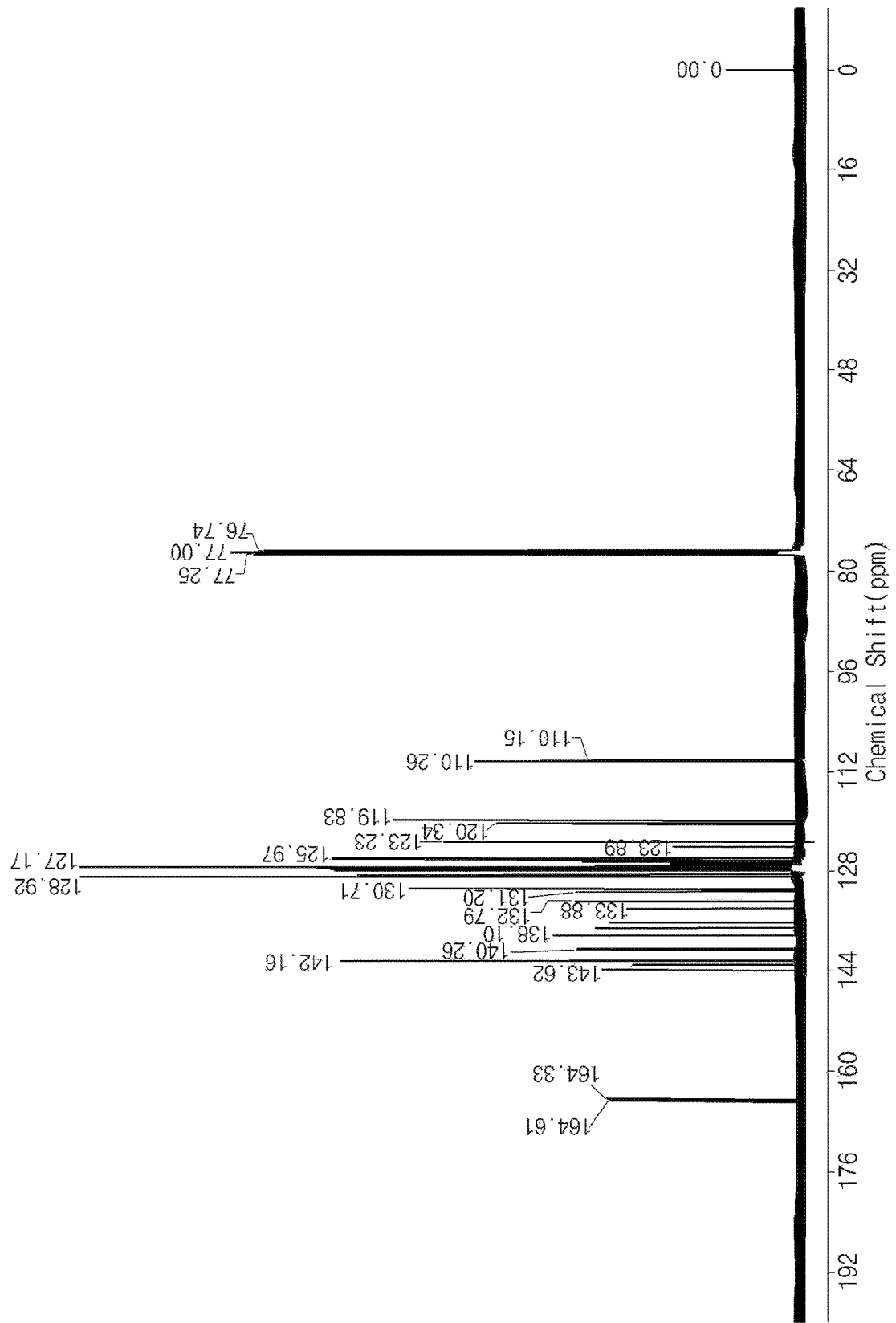
Figure 11A:
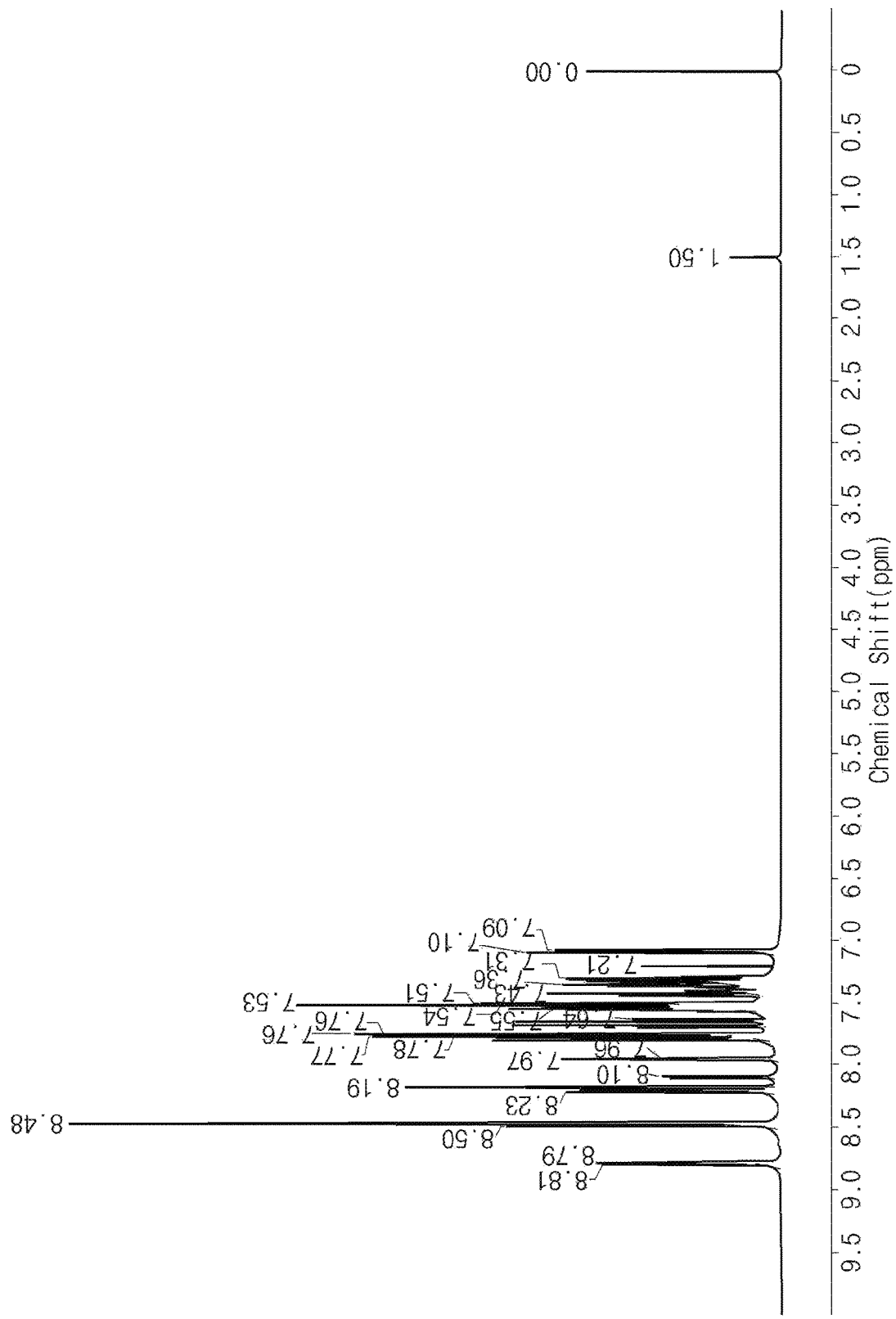
FIGS. 11A and 11B illustrate the $^1$H NMR and $^{13}$C NMR graphs, respectively, of Compound 2 of the present disclosure.
Figure 11B:
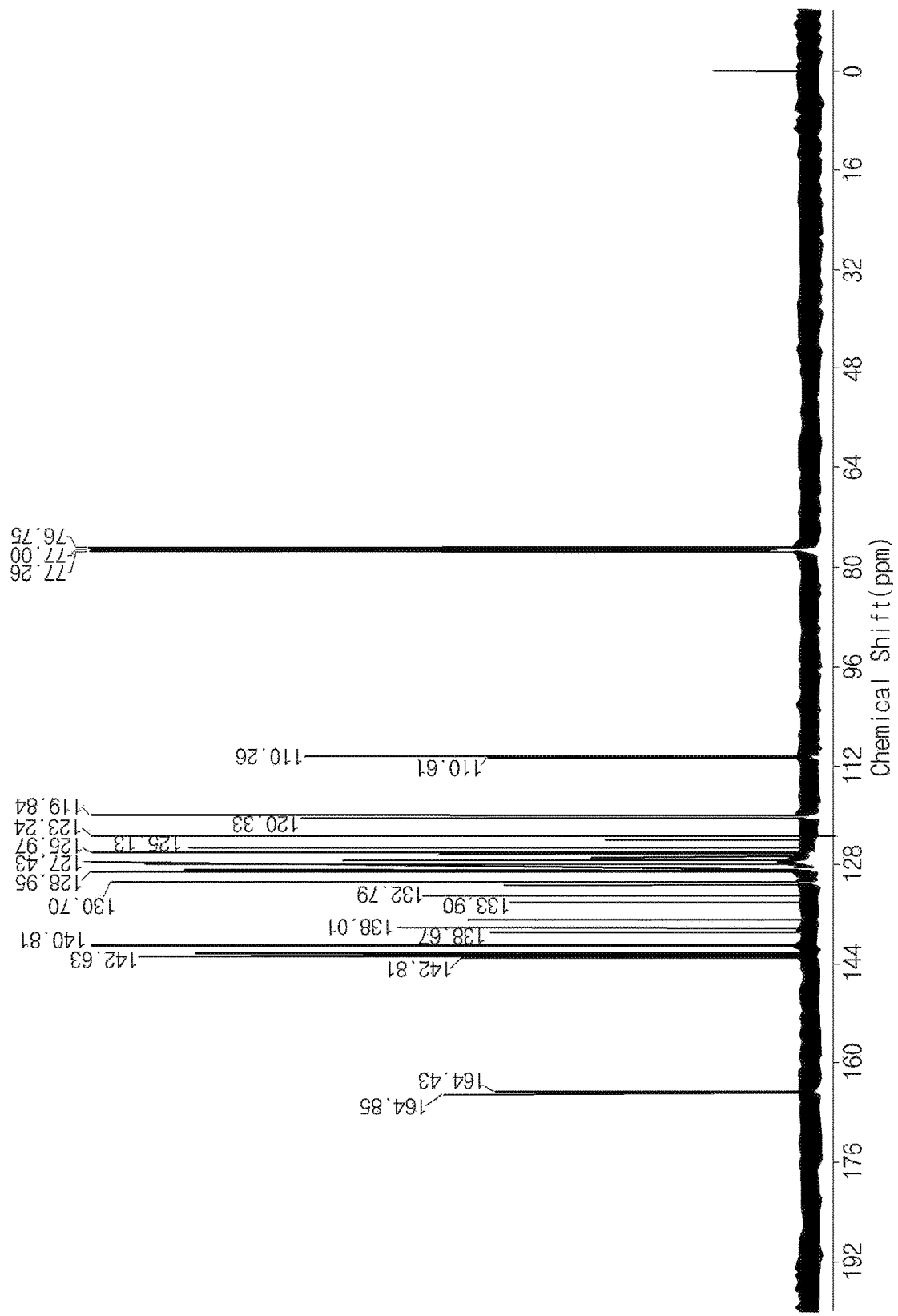
Figure 12A:
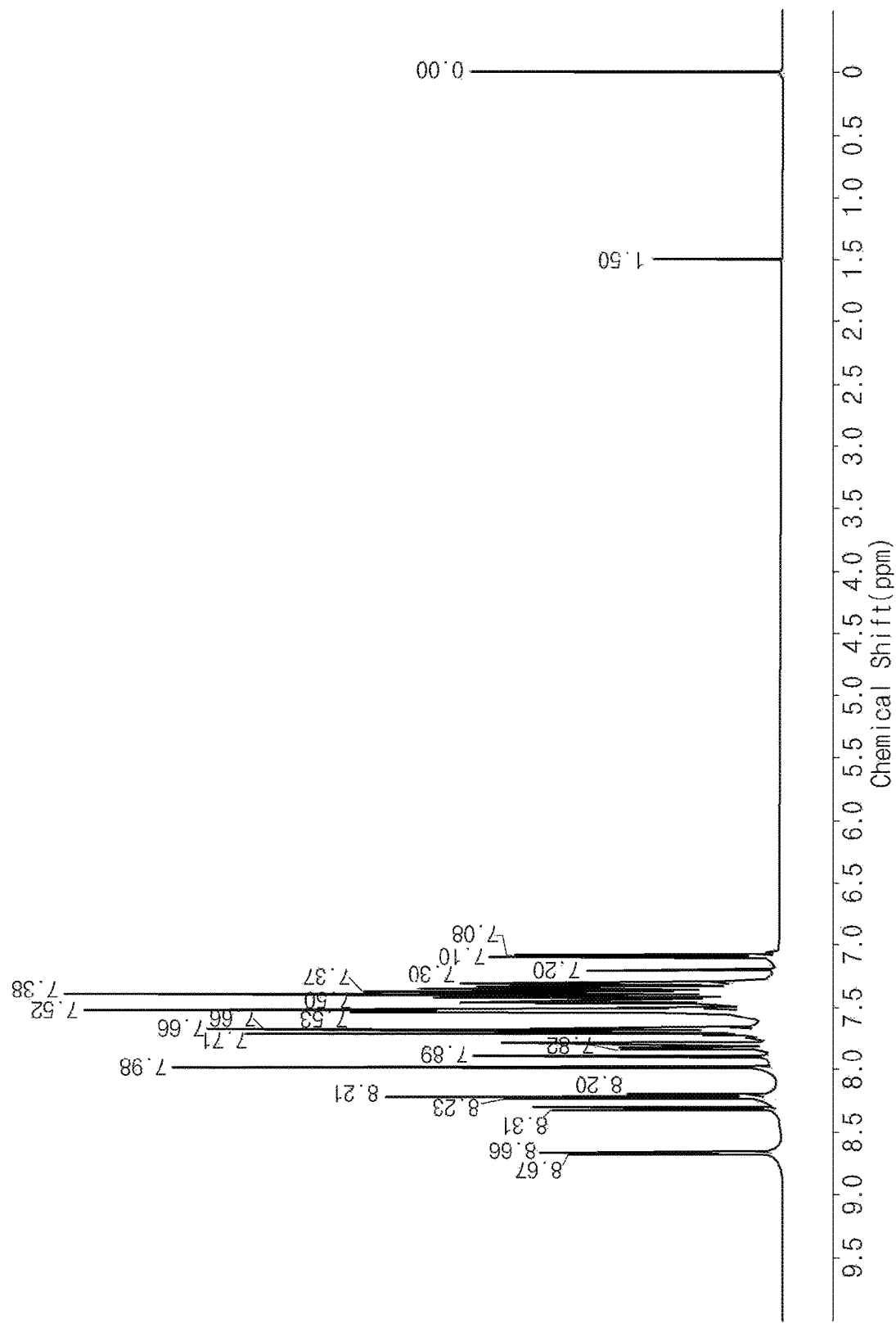
FIGS. 12A and 12B illustrate the $^1$H NMR and $^{13}$C NMR graphs, respectively, of Compound 3 of the present disclosure.
Figure 12B:
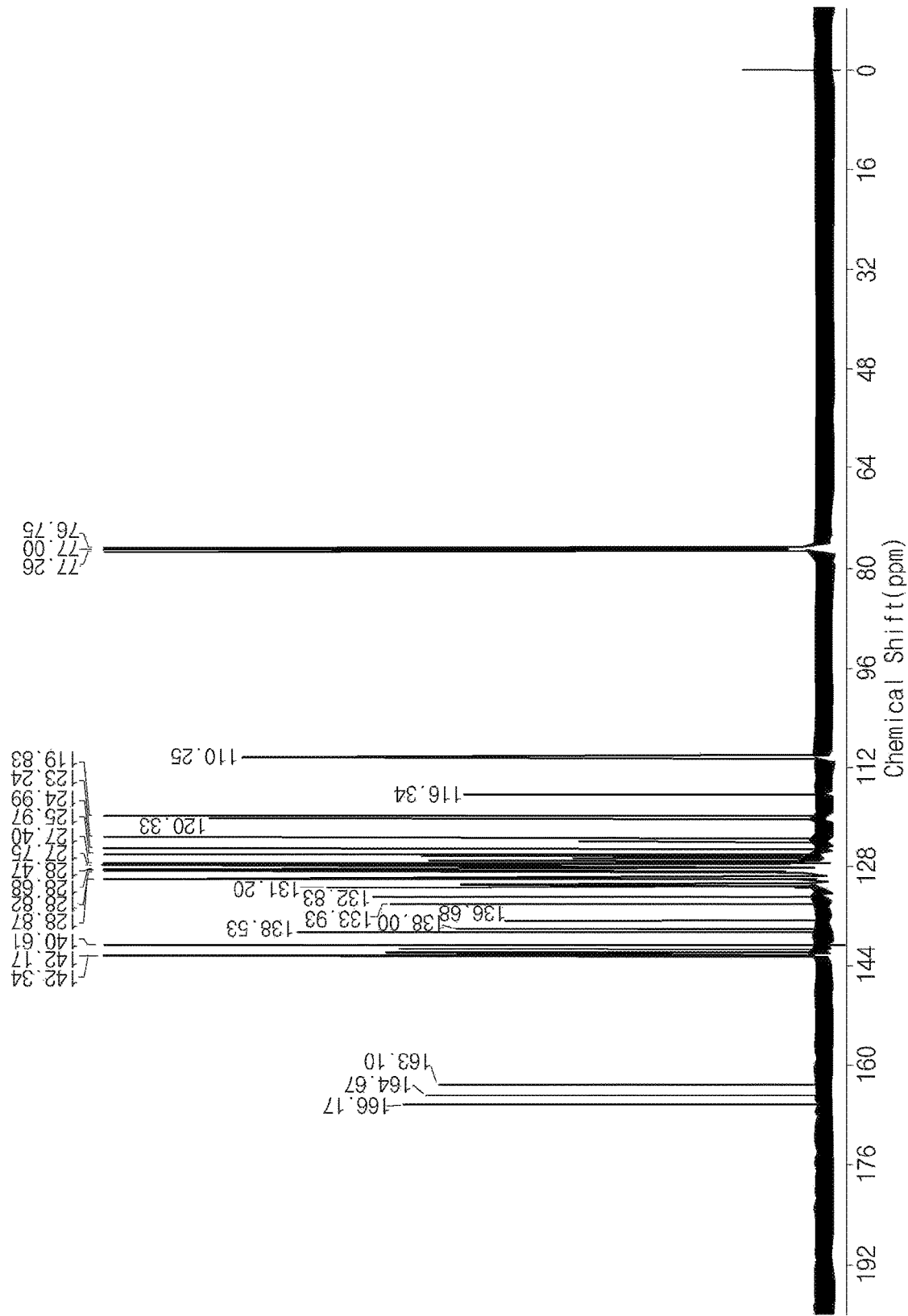
Figure 13A:
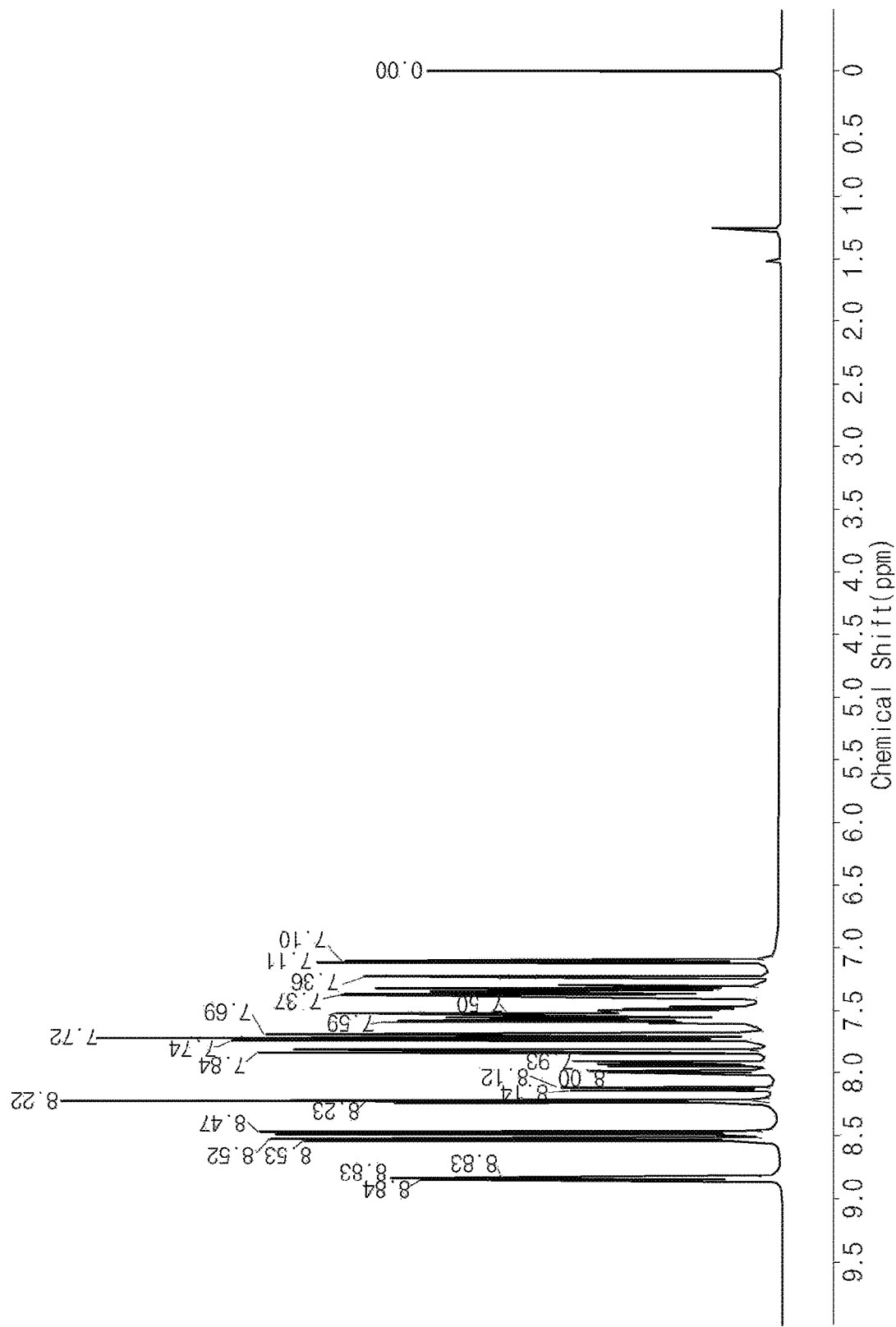
FIGS. 13A and 13B illustrate the $^1$H NMR and $^{13}$C NMR graphs, respectively, of Compound 5 of the present disclosure.
Figure 13B:
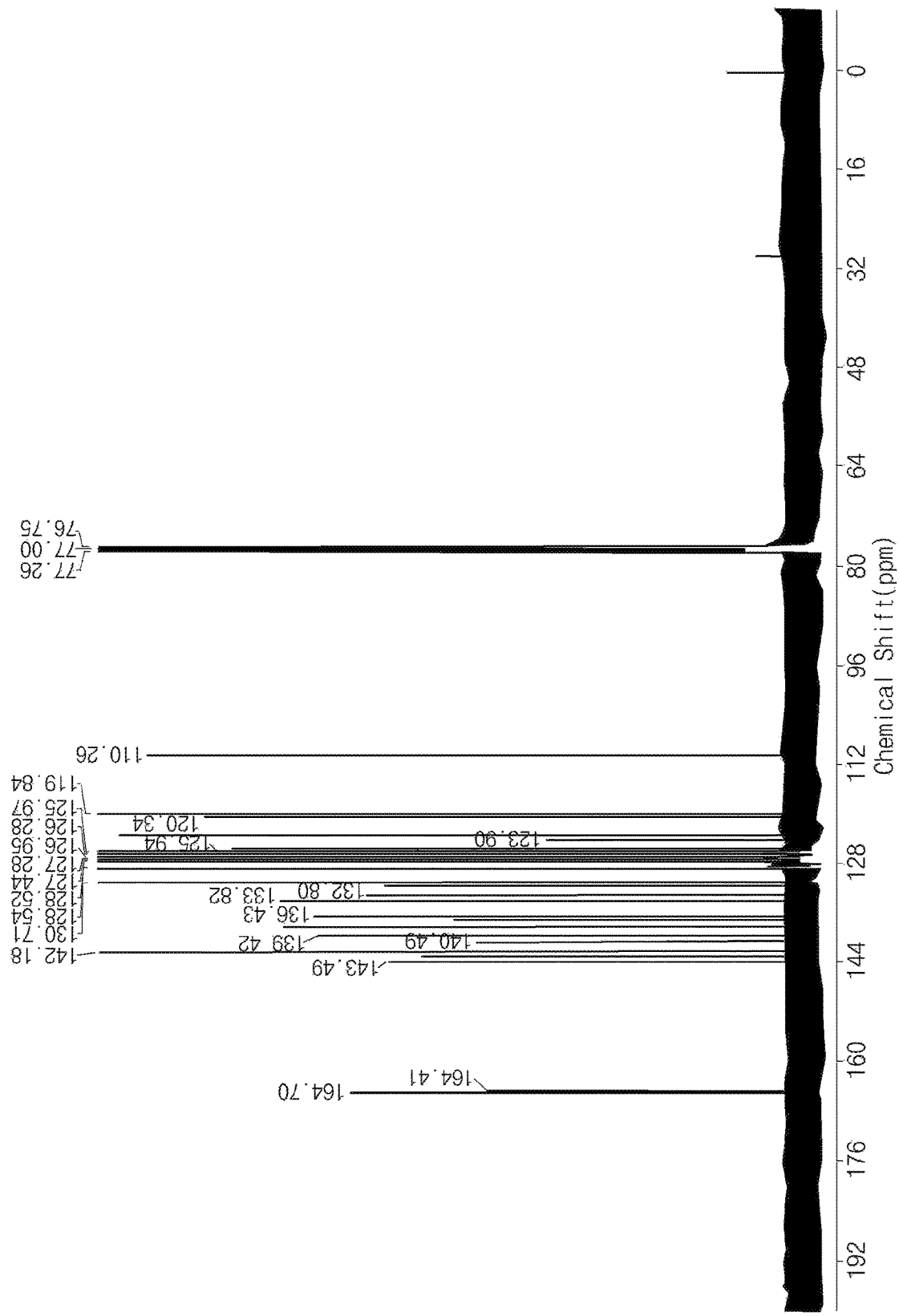
Figure 14A:
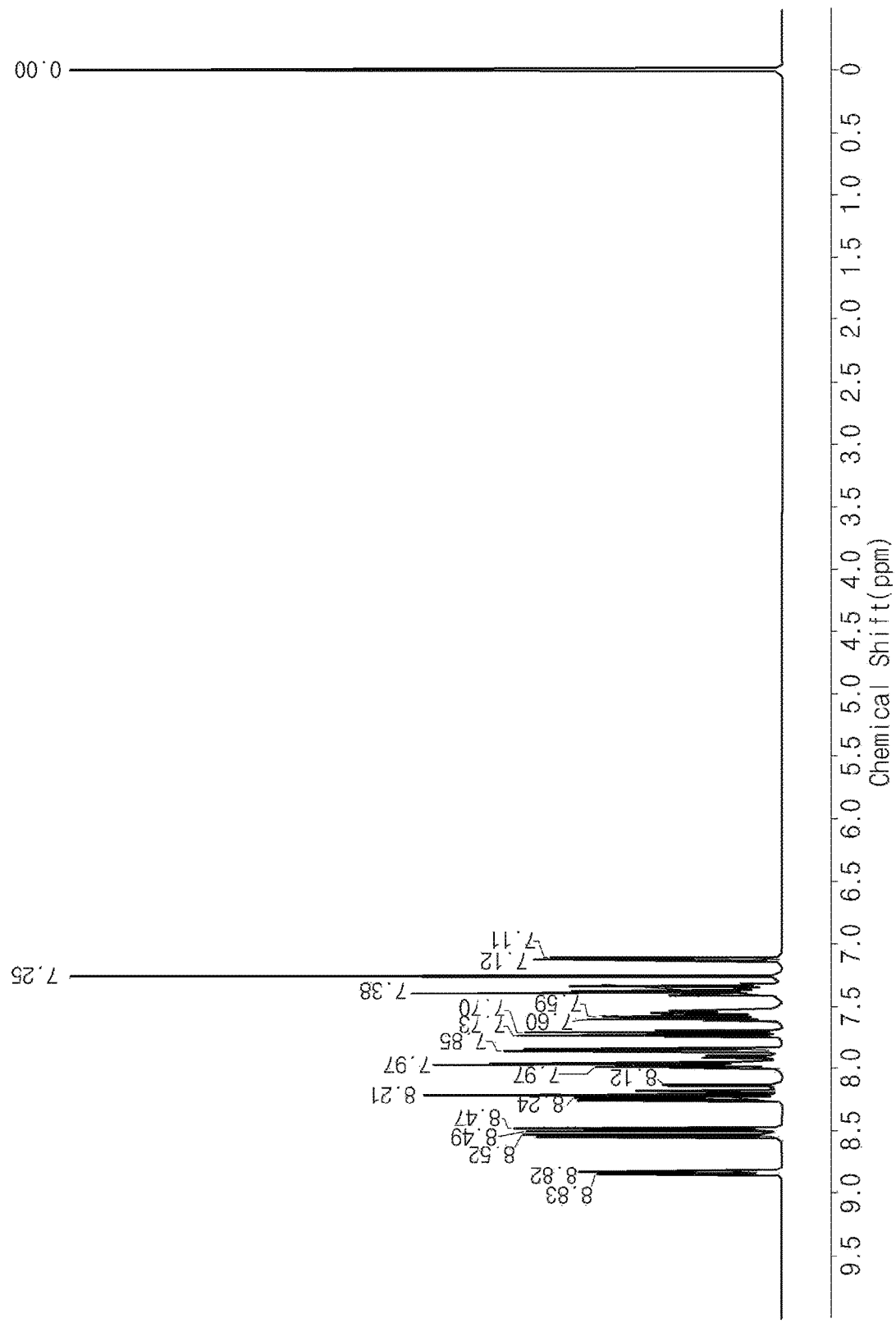
FIGS. 14A and 14B illustrate the $^1$H NMR and $^{13}$C NMR graphs, respectively, of Compound 6 of the present disclosure.
Figure 14B:
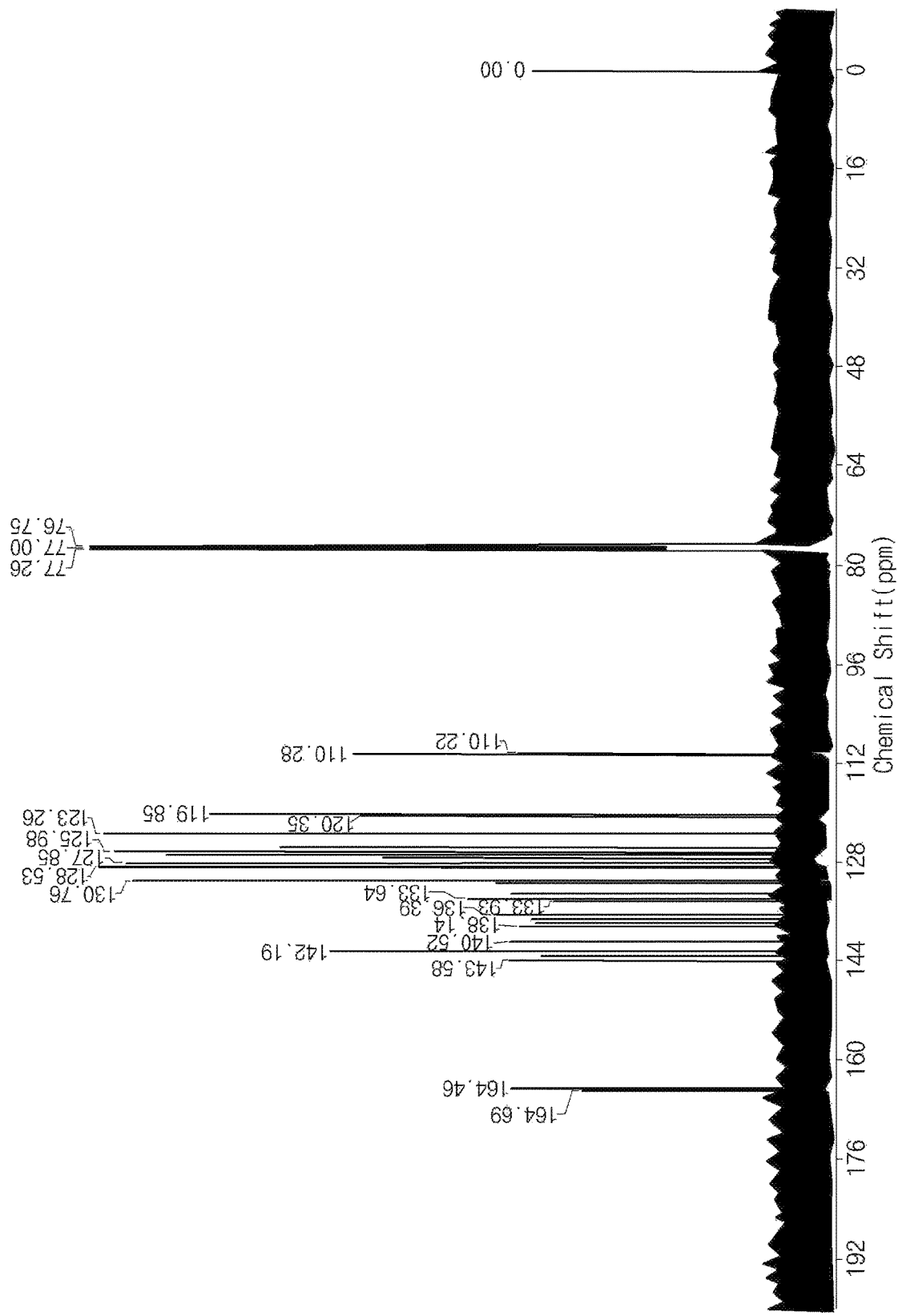
Figure 15A:
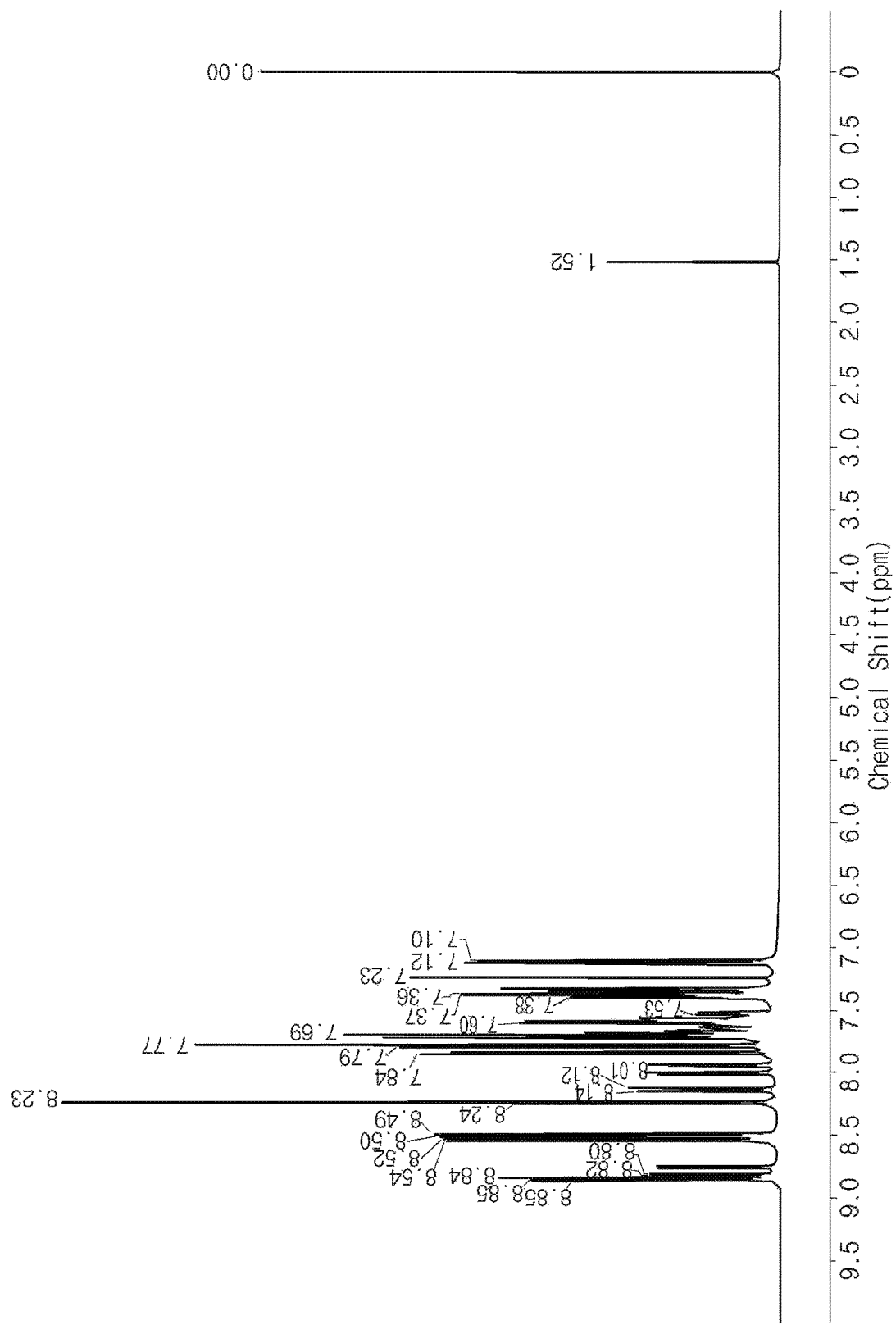
FIGS. 15A and 15B illustrate the $^1$H NMR and $^{13}$C NMR graphs, respectively, of Compound 7 of the present disclosure.
Figure 15B:
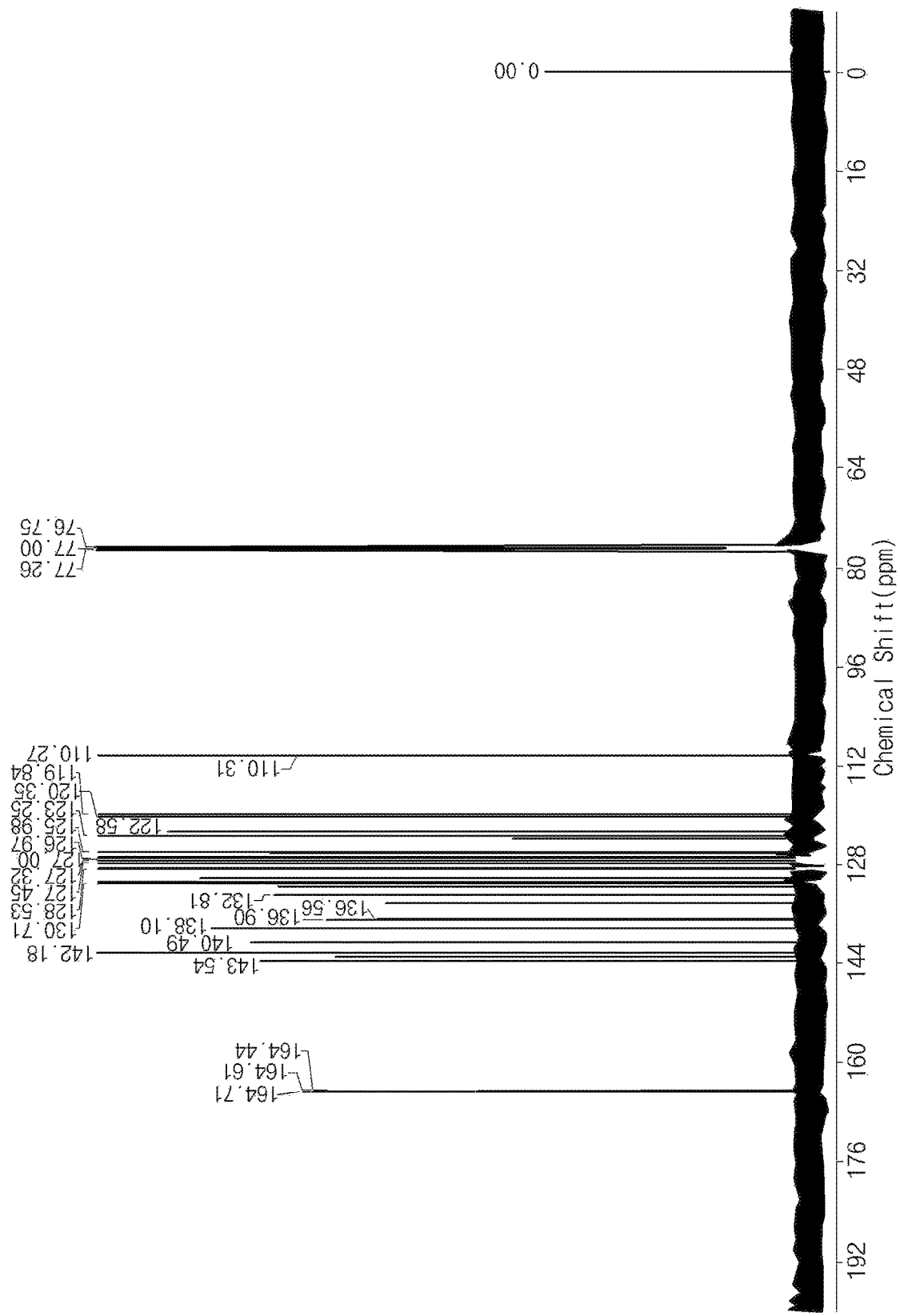
Figure 16A:
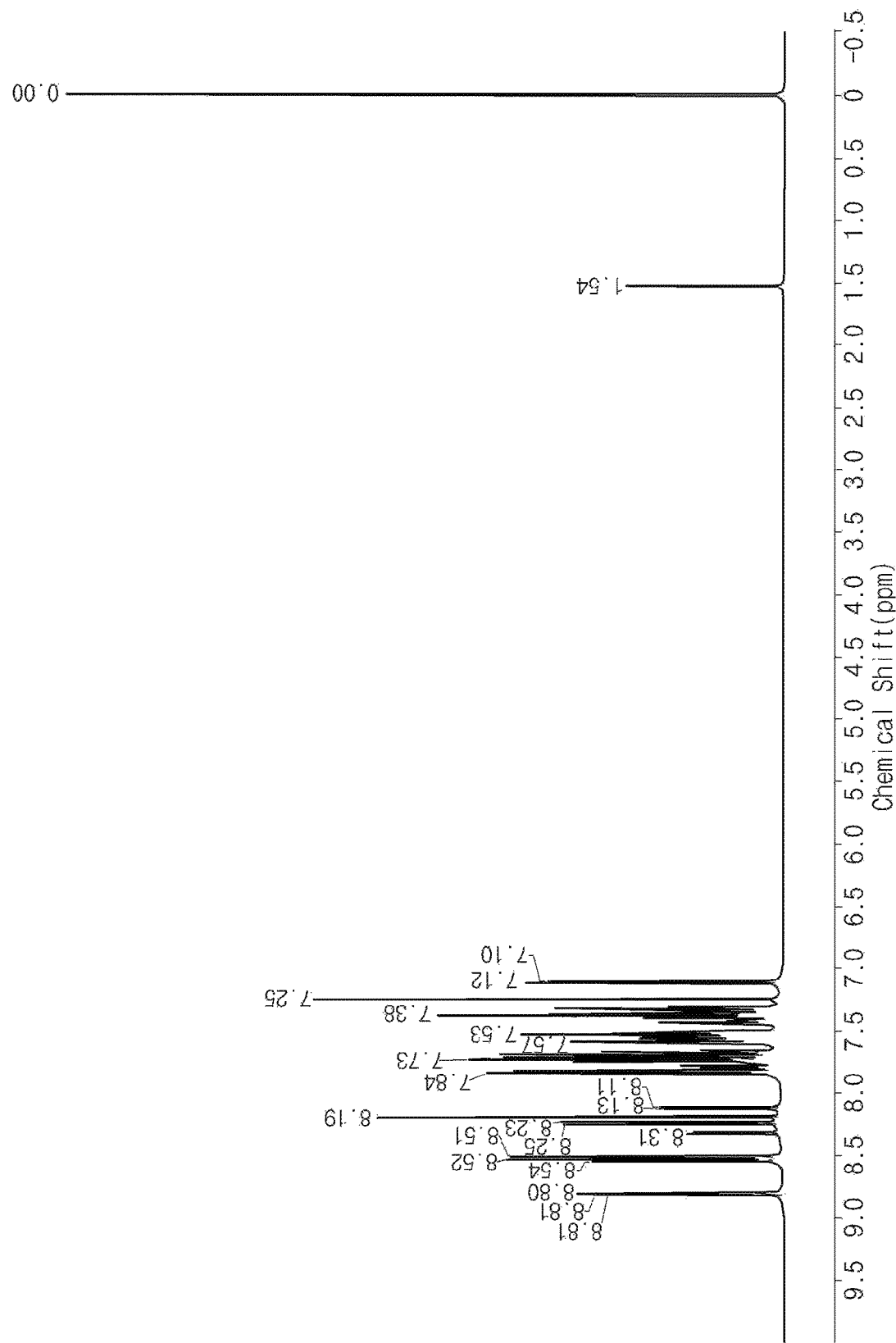
FIGS. 16A and 16B illustrate the $^1$H NMR and $^{13}$C NMR graphs, respectively, of Compound 8 of the present disclosure.
Figure 16B:
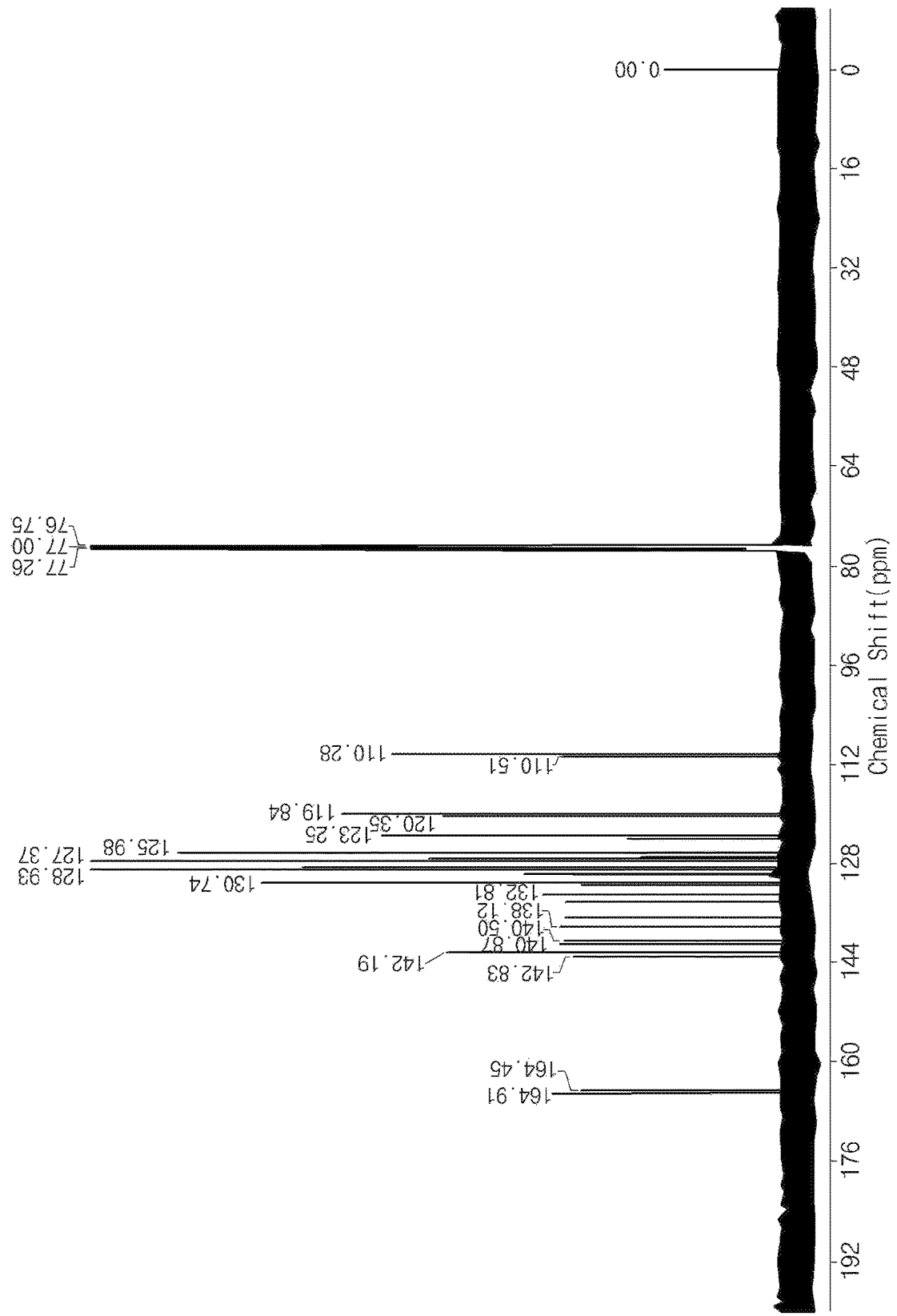
Figure 17A:
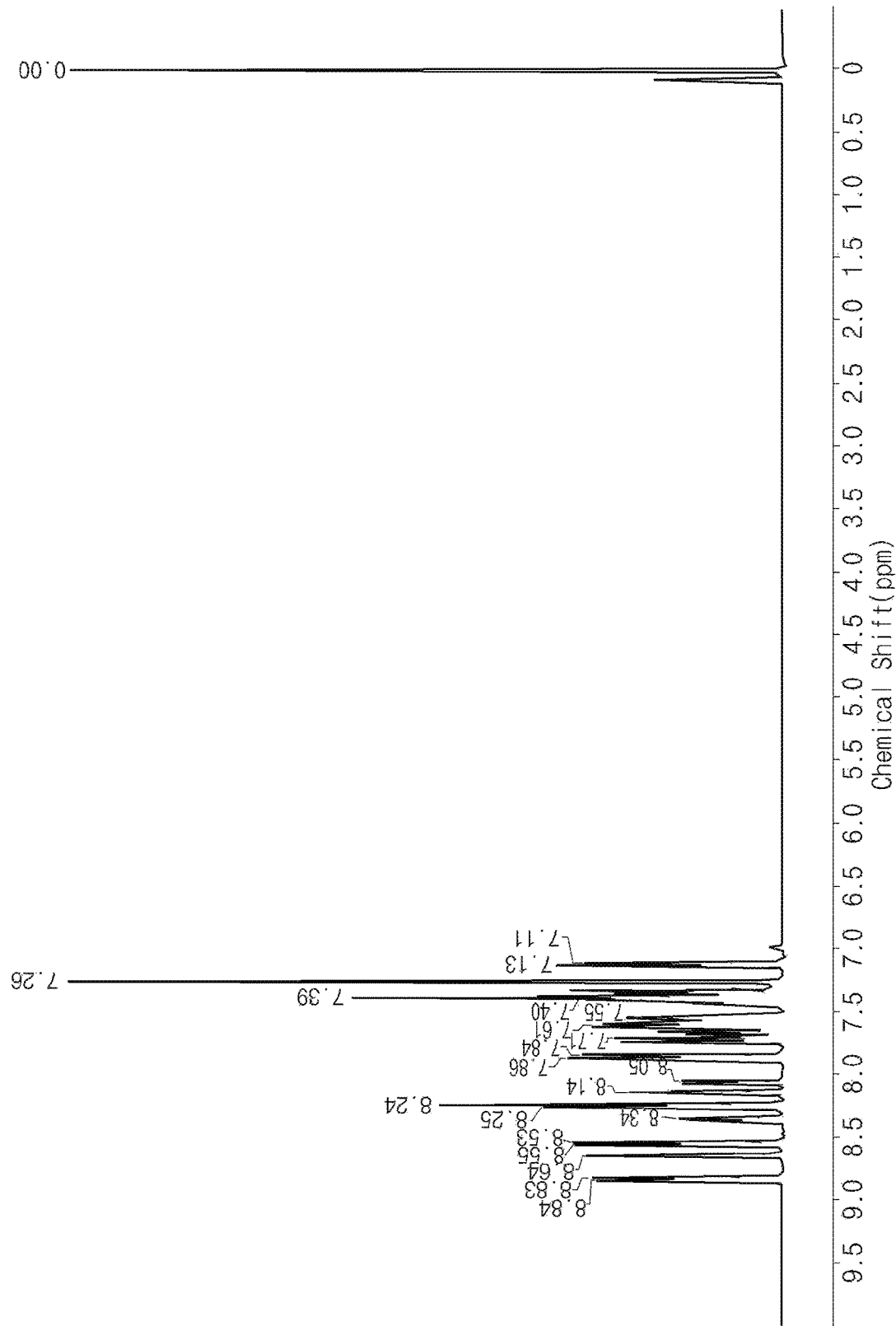
FIGS. 17A and 17B illustrate the $^1$H NMR and $^{13}$C NMR graphs, respectively, of Compound 9 of the present disclosure.
Figure 17B:
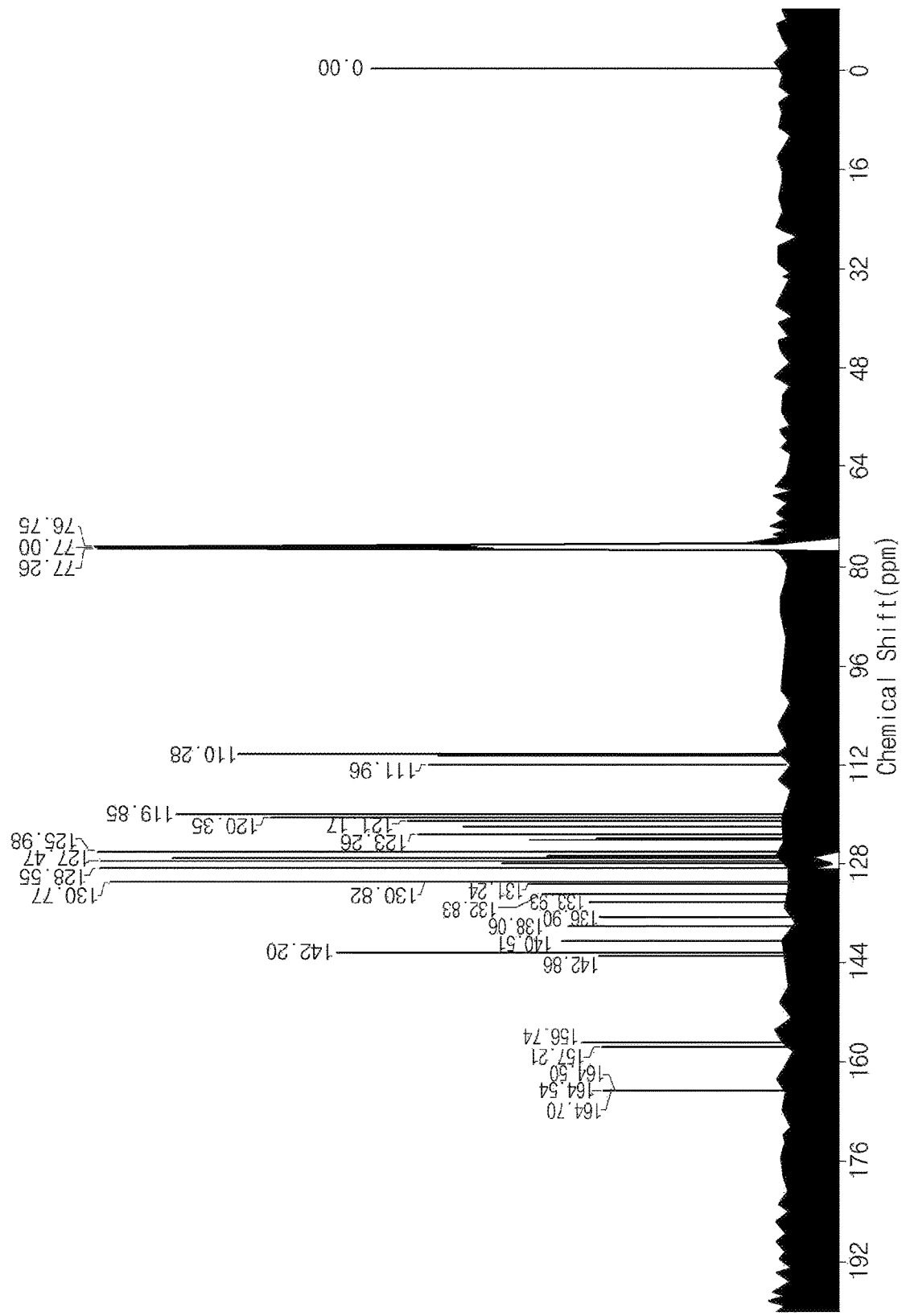
Figure 18:
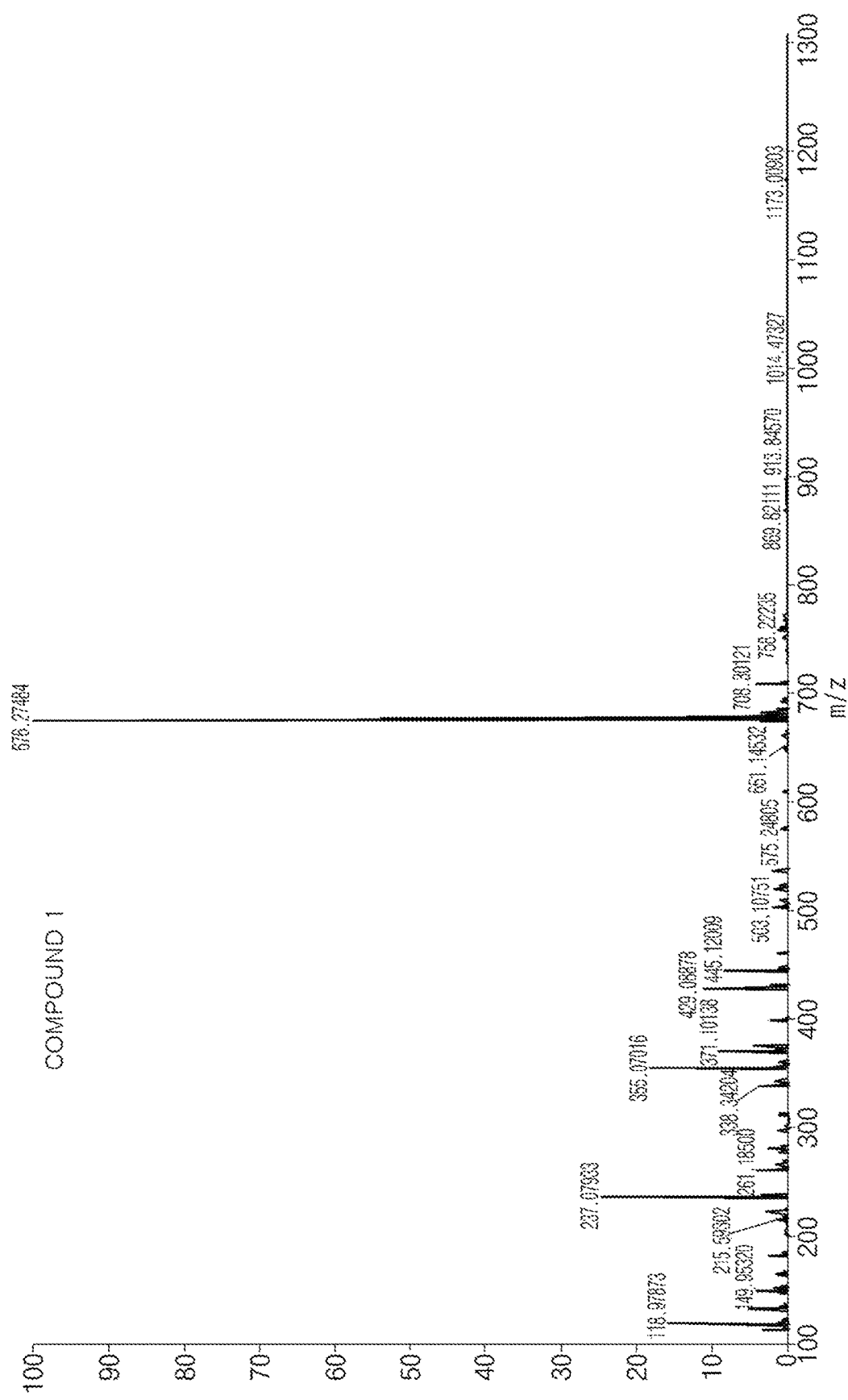
FIG. 18 illustrates the High Resolution Mass Spectrometry (HRMS) graph of Compound 1 of the present disclosure.
Figure 19:
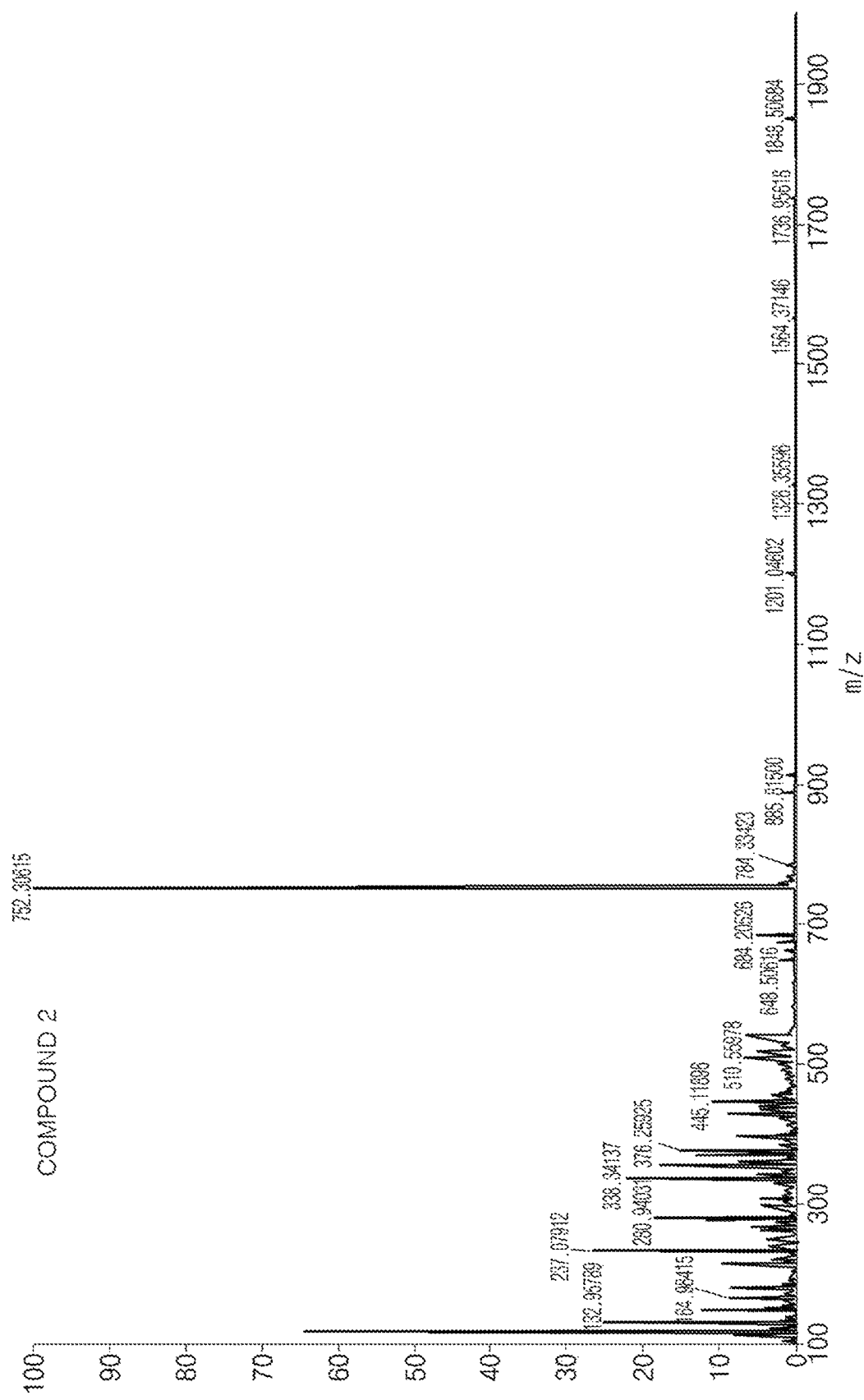
FIG. 19 illustrates the HRMS graph of Compound 2 of the present disclosure.
Figure 20:
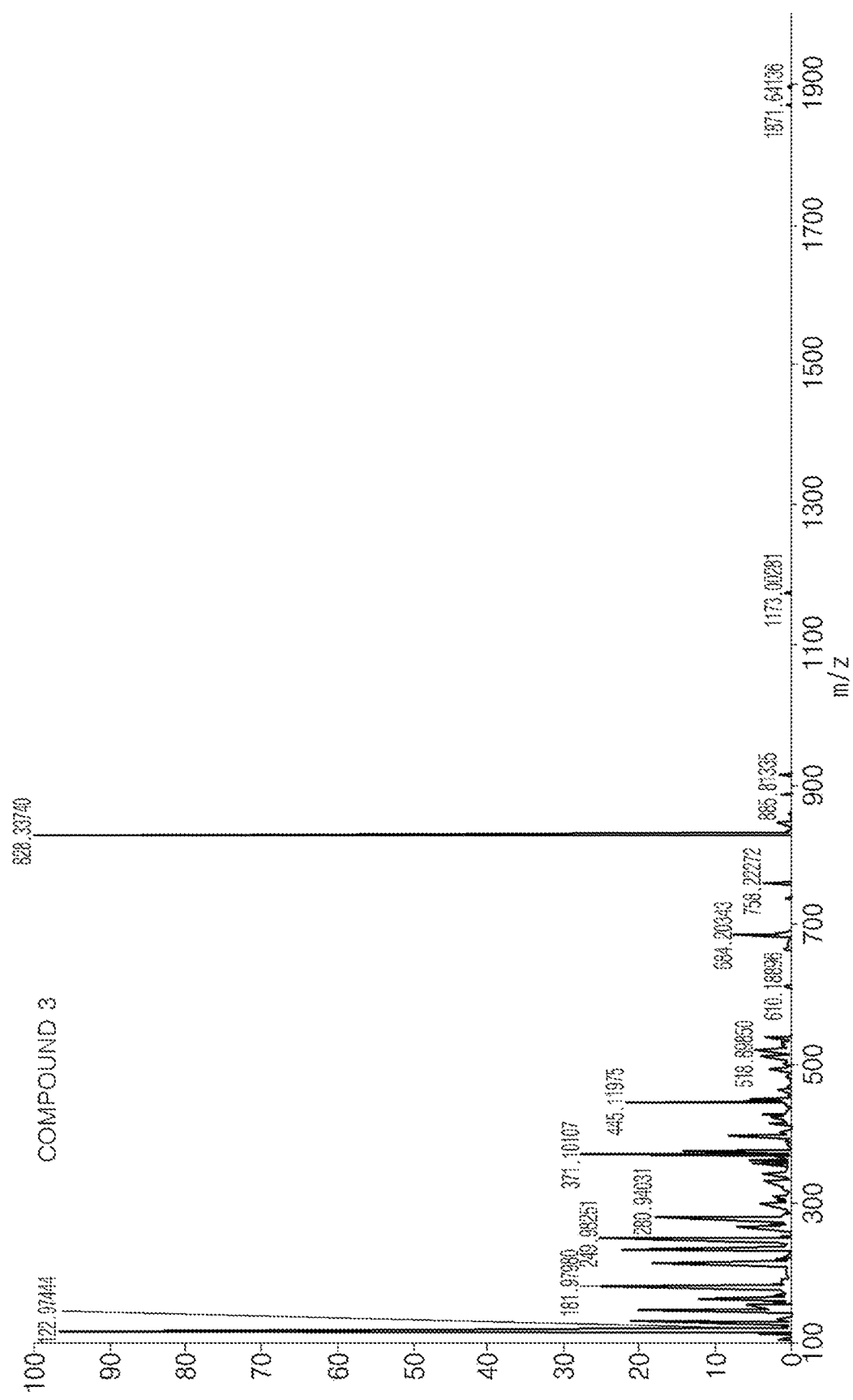
FIG. 20 illustrates the HRMS graph of Compound 3 of the present disclosure.
Figure 21:
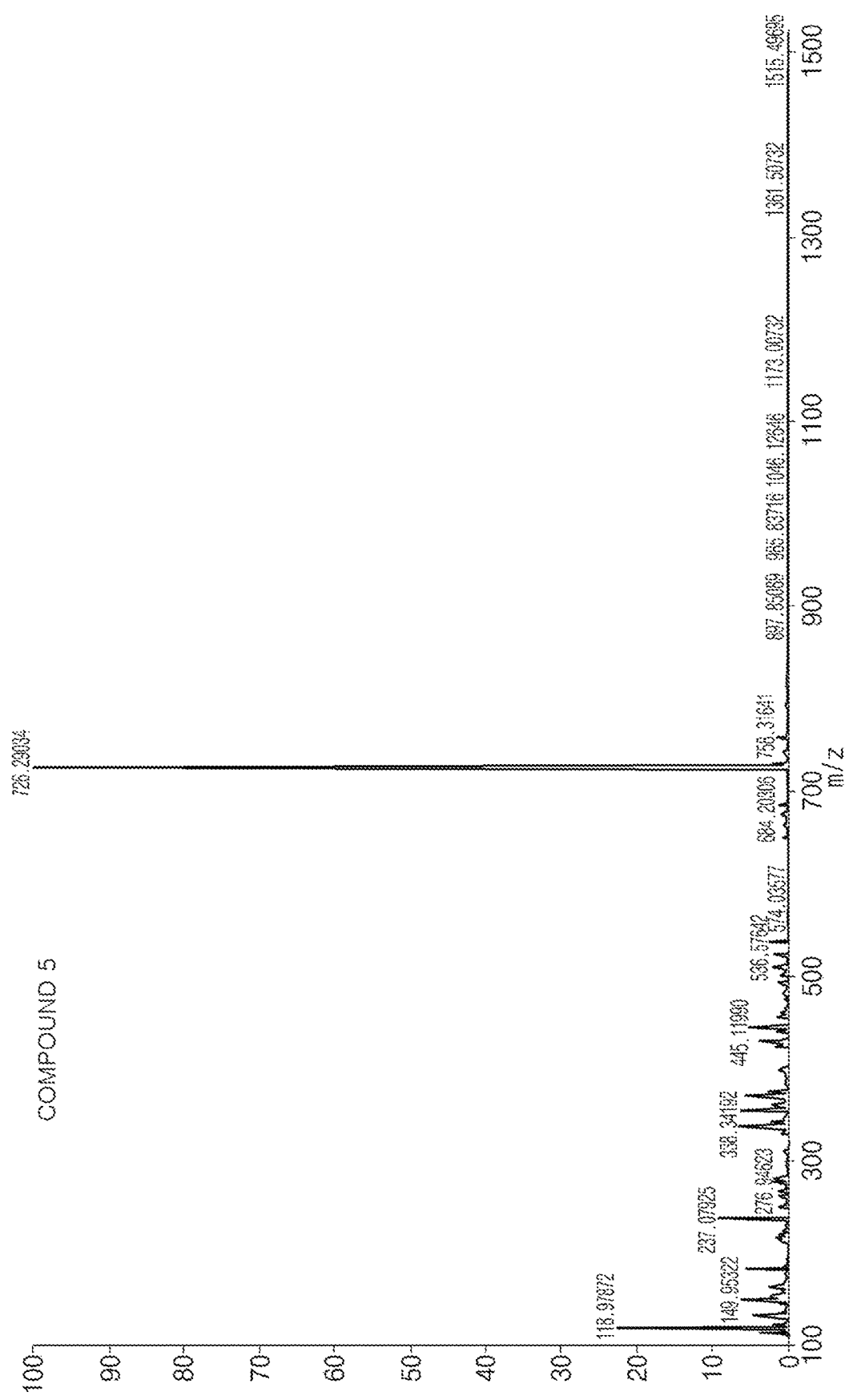
FIG. 21 illustrates the HRMS graph of Compound 5 of the present disclosure.
Figure 22:
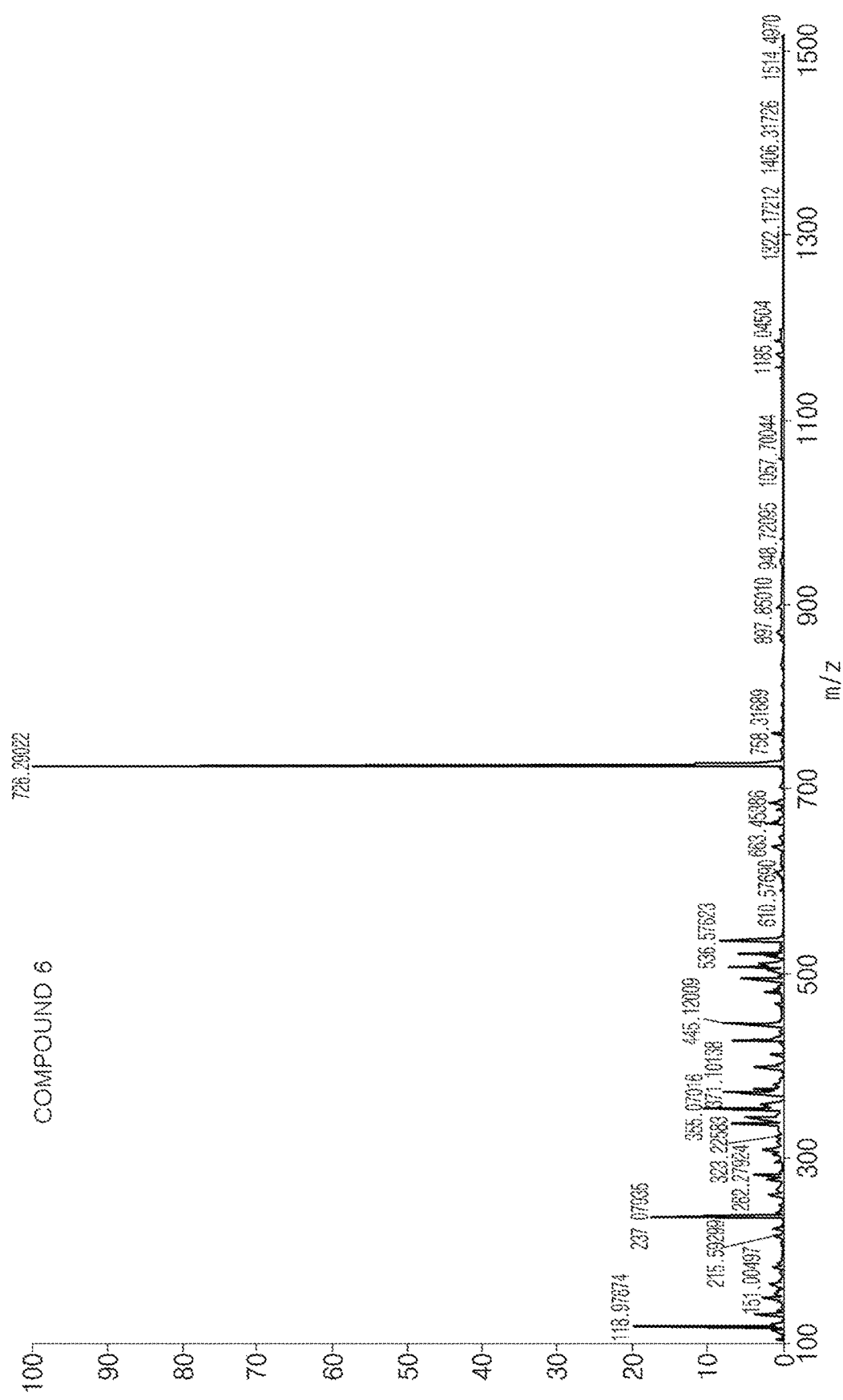
FIG. 22 illustrates the HRMS graph of Compound 6 of the present disclosure.
Figure 23:
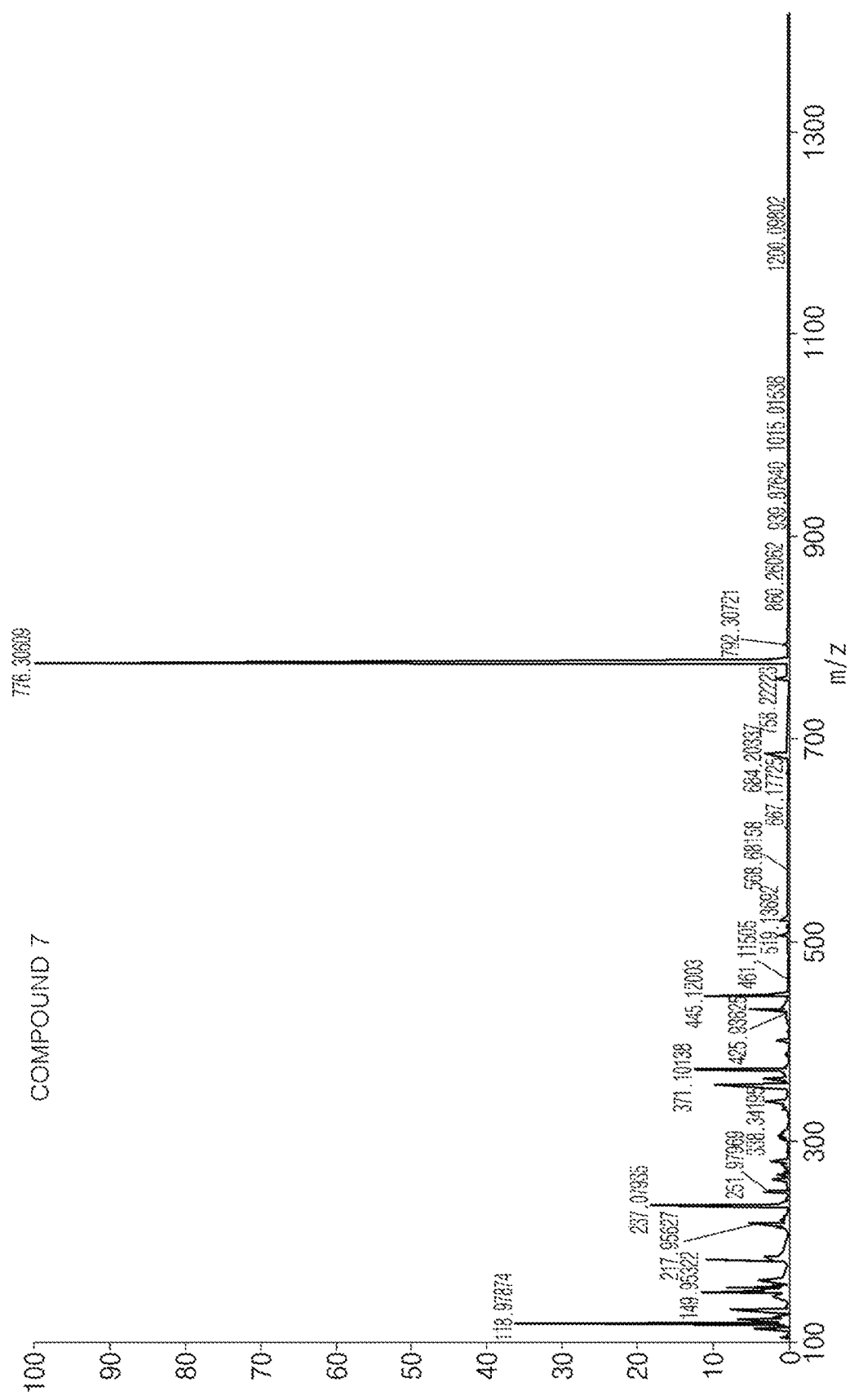
FIG. 23 illustrates the HRMS graph of Compound 7 of the present disclosure.
Figure 24:
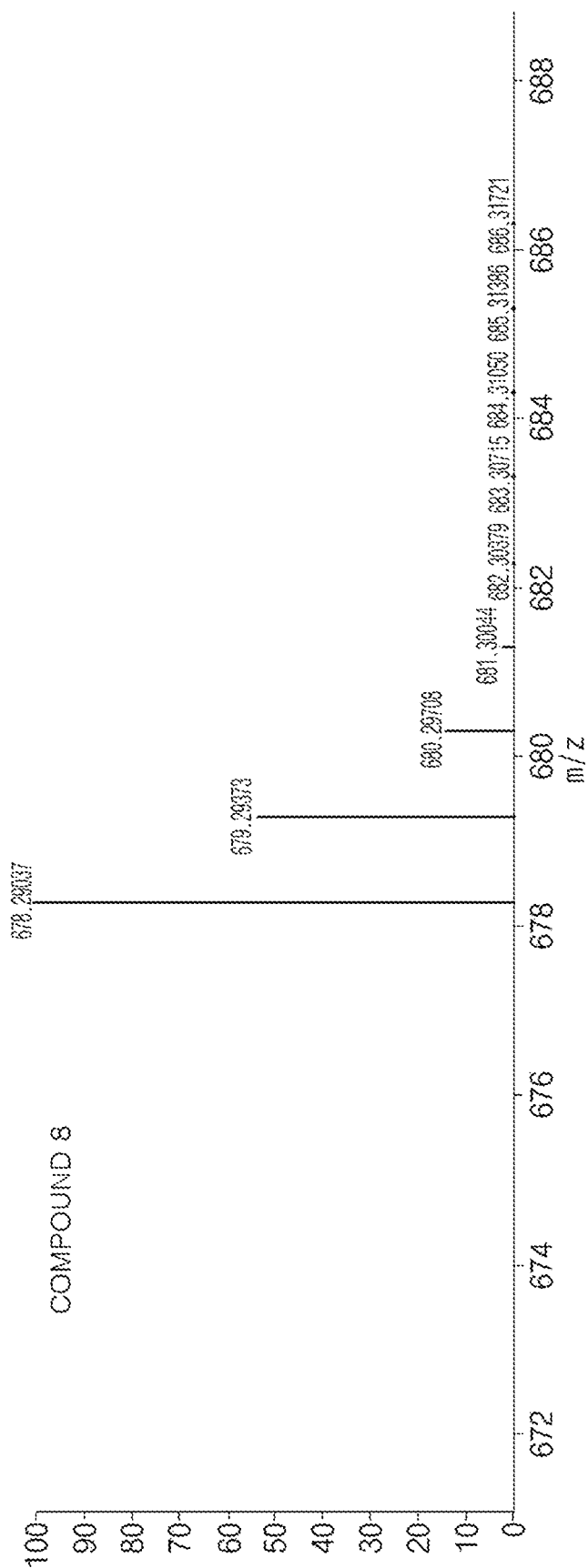
FIG. 24 illustrates the HRMS graph of Compound 8 of the present disclosure.
Figure 25:
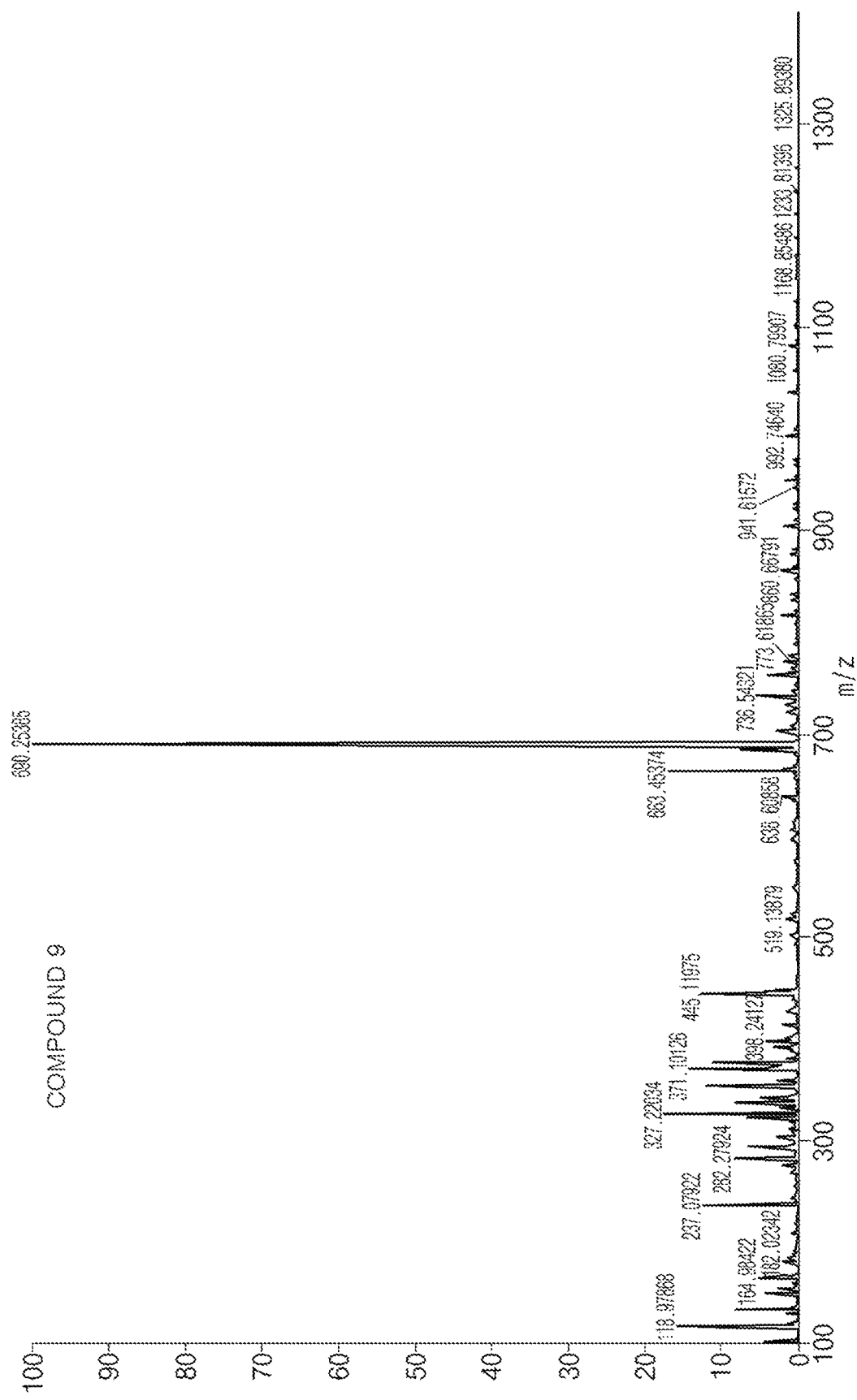
FIG. 25 illustrates the HRMS graph of Compound 9 of the present disclosure.

Hereinafter, the present disclosure is described in detail.

Compound

In one aspect, the present disclosure provides a compound comprising one or more selected from the group consisting of Chemical Formulas 1 to 9 as follows:

[Chemical Formula 1]

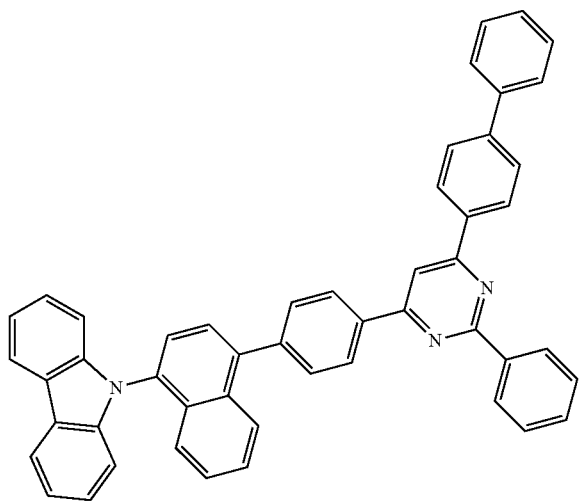

[Chemical Formula 2]

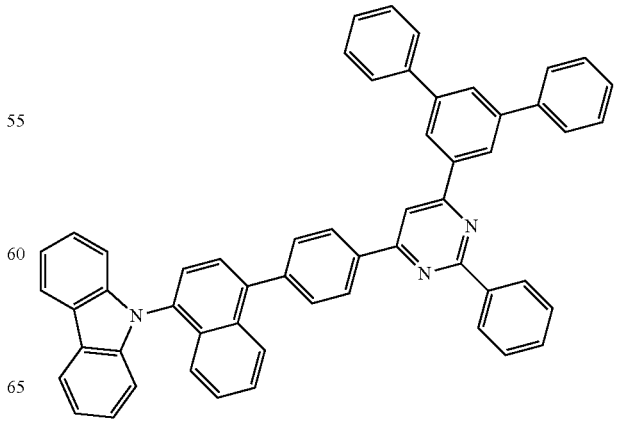

[Chemical Formula 3]
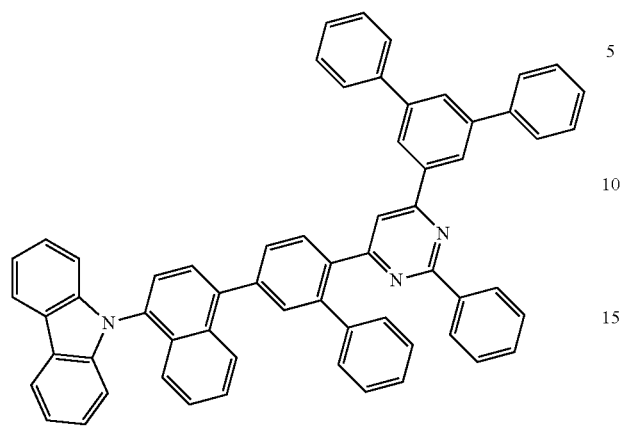
[Chemical Formula 4]
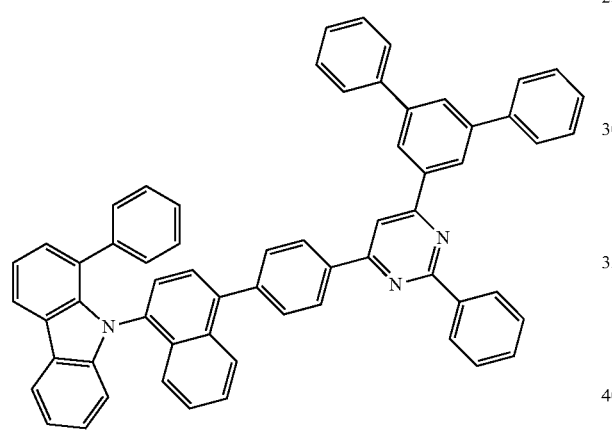
[Chemical Formula 5]
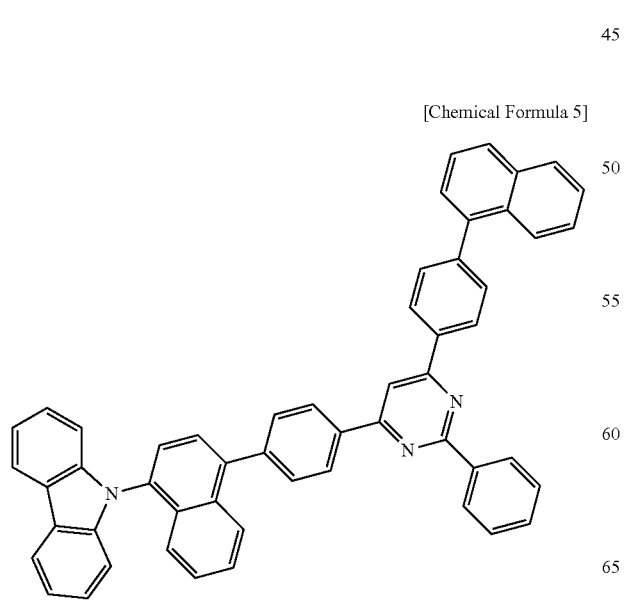
[Chemical Formula 6]
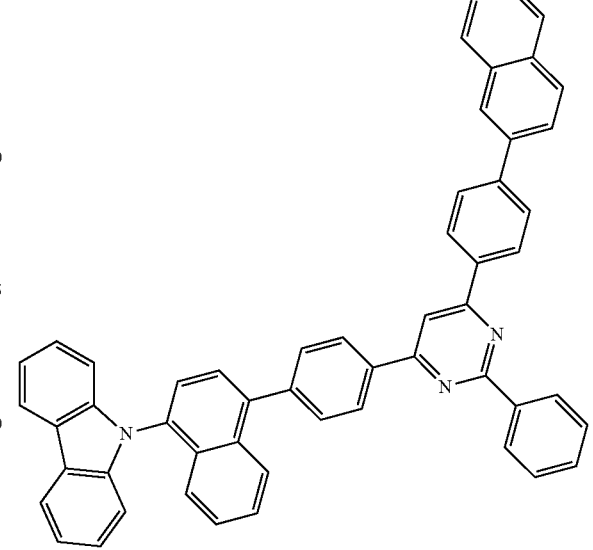
[Chemical Formula 7]
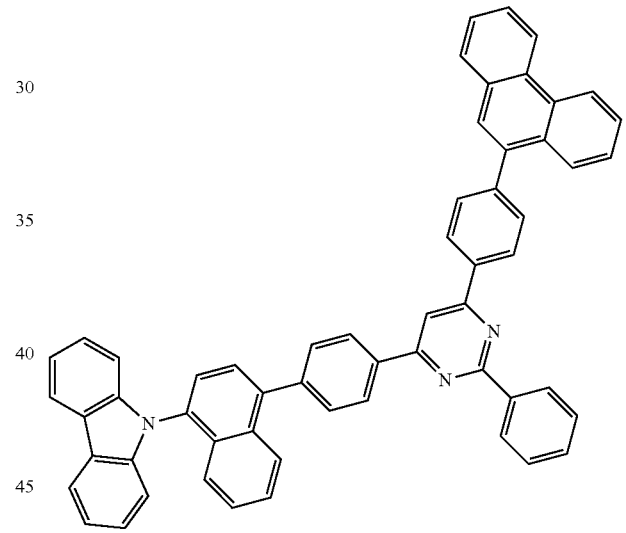
[Chemical Formula 8]
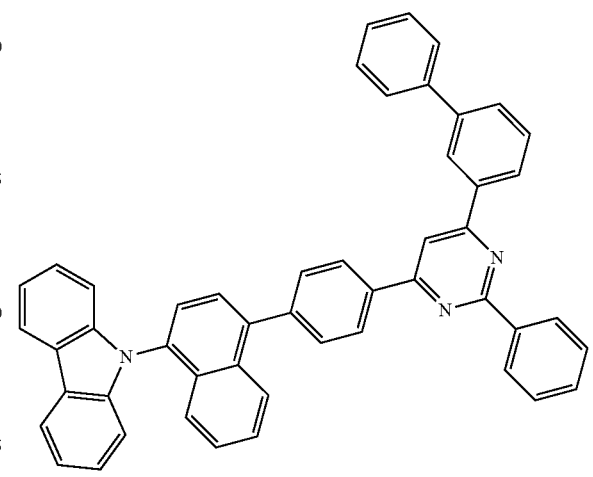

-continued

[Chemical Formula 9]

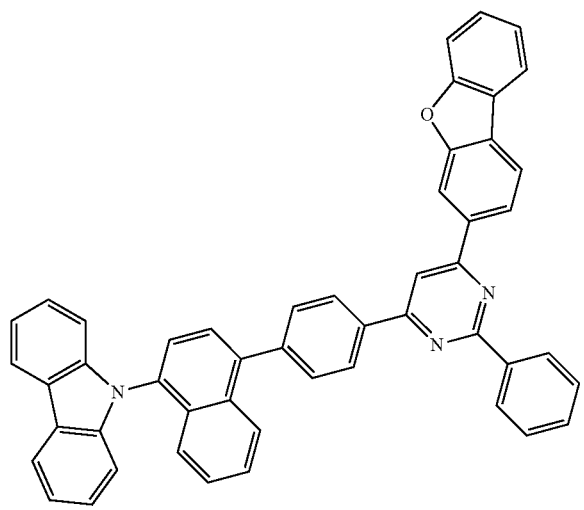

The compound of the present disclosure is a bipolar compound in which three characteristic substituents, that is, a carbazole group, a naphthalene group, and a polycyclic aromatic hydrocarbon group, are bonded to a hetero ring, thus enabling proper control of the HOMO or LUMO energy level, and enabling the balance between holes and electrons to be controlled from within one molecule to adjust the efficiency and lifetime characteristics. Specifically, the compound of the present disclosure comprises the carbazole group to achieve excellent device lifetime characteristics, the naphthalene group to achieve improvement of the lifetime through stabilization of the radical cations generated from carbazole when under an electric field, and the polycyclic aromatic hydrocarbon group to aid in molecular packing through introduction of rigid and bulky substituents, thereby achieving excellent improvements in the driving voltage and material thermal stability.

In addition, the material comprising the compound of the present disclosure has excellent hole blocking and exciton blocking abilities, thereby exhibiting outstanding power consumption characteristics.

The substituents of the compound may be bonded using methods known in the art, and the type, position or number of substituents may be modified according to techniques known in the art.

The conjugation length and energy bandgap of a compound are closely related. Specifically, the longer the conjugation length of the compound, the smaller the energy bandgap. Thus, by introducing various substituents to the compound of the present disclosure, it is possible to synthesize a compound having various energy bandgaps. In addition, in the present disclosure, the HOMO and LUMO energy levels of the compound may be controlled by introducing various substituents into the core structure described above.

In addition, through the introduction of various substituents into the above-described core structure, it is possible to synthesize a compound having the inherent characteristics of the substituents introduced. For example, through introduction of a substituent which is mainly used in a hole injection material, a hole transport material, a light emitting layer material and/or an electron transport material used in the manufacture of an organic light emitting device, it is possible to synthesize a material satisfying the conditions required for each organic material layer.

Further, by introducing various substituents into the structures of Chemical Formulas 1 to 9, it is possible to finely control the energy bandgap while improving the interface properties between organic materials, thereby enabling various uses of the materials.

Meanwhile, the compound of the present disclosure has a high glass transition temperature (Tg) to provide excellent thermal stability. This increase in the thermal stability is an important factor in providing drive stability to the device.

The compound according to the present disclosure may be prepared by a multistep chemical reaction. Some intermediate compounds may be prepared first, and the compound of the present disclosure may be prepared from the intermediate compounds. Specifically, a method for preparing a compound according to the present disclosure may be performed as in the following Examples.

Material for Organic Light Emitting Device

The material for an organic light emitting device according to the present disclosure comprises the above-described compound.

Specifically, the material may be used as at least one selected from the group consisting of a hole blocking material, an electron injecting material, an electron transport material, and a host material of a light emitting layer.

The compound has excellent electron transport performance, hole or exciton blocking performance, and electron injection performance, making it very suitable for use as a material for an organic light emitting device. Specifically, the material for an organic light emitting device comprising the compound has excellent electron injection characteristics and electron mobility, and the balance of bipolar characteristics of the compound, that is, the balance of the n-type portion and the p-type portion, may be properly maintained to appropriately control the HOMO or LUMO energy level. Thus, the material for an organic light emitting device has excellent lifetime characteristics, and excellent hole blocking and exciton blocking abilities, thereby achieving outstanding power consumption characteristics.

Organic Light Emitting Device

The organic light emitting device according to the present disclosure comprises the above-described compound. When the compound of the present disclosure is used in the organic light emitting device, the organic light emitting device has improved efficiency, low driving voltage, and excellent lifetime characteristics.

Throughout the present specification, unless explicitly described to the contrary, a case wherein a portion "comprises" or "includes" some elements shall not be interpreted to imply the exclusion of all other elements, but rather shall be understood to allow the possibility of inclusion of any further elements.

Throughout the present specification, a case where any one component is located on another component includes not only the case wherein one component is in contact with the other, but also the case wherein another component is present between the two components.

Specifically, the organic light emitting device may comprise a first electrode, a second electrode, and one or more organic material layers provided between the first and second electrode, and the organic material layers may include the compound of the present disclosure. Specifically, the organic material layer may comprise at least one layer from among a hole transport layer, a light emitting layer, and an electron transport layer. More specifically, the organic material layer may comprise an electron transport layer, and the electron transport layer may include the compound.

Except for the inclusion of the above-described compound, the organic light emitting device may be manufactured by any conventional method and material for manufacturing an organic light emitting device.

Specifically, the compound of the present disclosure may be formed as an organic material layer not only by using the vacuum deposition method at the time of manufacture of the organic light emitting device, but also by a solution coating method. Here, the solution coating method refers to spin coating, dip coating, inkjet printing, screen printing, spraying, roll coating, and the like, but is not limited thereto. For example, the solution coating method may be applied for the formation of the organic material layer even when the compound of the present disclosure is used as a material for the light emitting layer, the hole blocking layer, the electron transport layer, or the electron injection layer.

As an example, when an organic material layer is formed from the compound of the present disclosure, the lower organic material layer may be formed by the solution coating method, and the organic material layer comprising the compound of the present disclosure may be formed by the vacuum deposition method. Specifically, in the case where the compound of the present disclosure is employed as the material for the hole transport layer, the electron transport layer, or the electron injection layer, when the light emitting layer is formed on the first electrode, or when the hole transport layer and/or electron transport layer and the light emitting layer are formed on the first electrode, the solution coating method may be used, and then the vacuum deposition method may be used to form the organic material layer comprising the compound of the present disclosure thereon. In this case, even though the organic material layer comprising the compound of the present disclosure is prepared by the vacuum deposition method, it is well matched with the lower organic material layer formed by the solution coating method.

FIG. 1 illustrates a cross section of the organic light emitting device according to an embodiment of the present disclosure, and a stacking order of the electrodes and the organic material layers. However, the scope of the present disclosure is not limited by the above-described drawing, and the structure of any organic light emitting devices known in the art can also be applied to the present disclosure.

In addition, referring to FIG. 1, in the organic light emitting device of the present disclosure, the first electrode, the hole injection layer, the light emitting layer, and the second electrode may be sequentially stacked on a substrate, but the stacking order is not limited thereto. Specifically, in the structure of FIG. 1, the compound of the present disclosure may be included in the light emitting layer or the hole injection layer.

More specifically, the organic light emitting device may have structures such as the following: substrate/first electrode/light emitting layer/second electrode; substrate/first electrode/hole injection layer/light emitting layer/second electrode; substrate/first electrode/hole transport layer/light emitting layer/second electrode; substrate/first electrode/ light emitting layer/electron transport layer/second electrode; substrate/first electrode/hole injection layer/hole transport layer/light emitting layer/second electrode; substrate/first electrode/light emitting layer/electron transport layer/second electrode; substrate/first electrode/light emitting layer/electron injection layer/second electrode; substrate/first electrode/light emitting layer/hole blocking layer/ second electrode; substrate/first electrode/light emitting layer/hole transport layer/electron injection layer/second electrode; substrate/first electrode/light emitting layer/hole blocking layer/electron transport layer/second electrode; substrate/first electrode/light emitting layer/hole blocking layer/electron transport layer/electron injection layer/second electrode; substrate/first electrode/hole injection layer/hole transport layer/light emitting layer/electron transport layer/ electron injection layer/second electrode; substrate/first electrode/hole injection layer/hole transport layer/electron blocking layer/light emitting layer/electron transport layer/ electron injection layer/second electrode; substrate/first electrode/hole injection layer/hole transport layer/electron blocking layer/light emitting layer/hole blocking layer/electron transport layer/electron injection layer/second electrode, and the like. Here, one or more of the organic material layers between the first electrode and the second electrode, such as the hole injection layer, the hole transport layer, the light emitting layer, the hole blocking layer, the electron transport layer or the electron injection layer, may include the compound of the present disclosure.

Specifically, the compound of the present disclosure may be used as a material for the light emitting layer, the hole blocking layer, the electron transport layer, or the electron injection layer in a device having the structure described above. More specifically, the compound of the present disclosure may be used as a material of the electron transport layer in a device having the structure described above.

In another embodiment, the organic light emitting device may comprise a charge generation layer including the compound of the present disclosure. For example, the organic light emitting device may comprise two or more light emitting units comprising light emitting layers, and the charge generation layer may be provided between two adjacent light emitting units. As another example, the organic light emitting device may comprise one or more light emitting units, and the charge generation layer may be provided between the light emitting unit and the first electrode, or between the light emitting unit and the second electrode.

Here, since the charge generation layer including the compound of the present disclosure may serve as an n-type charge generation layer, the charge generation layer including the compound of the present disclosure may be arranged to be in contact with a p-type organic compound layer.

The light emitting unit may be comprised of only a light emitting layer, or may further include one or more organic material layers such as a hole injection layer, a hole transport layer, an electron blocking layer, a hole blocking layer, an electron transport layer, an electron injection layer, and the like, as necessary.

For example, the organic light emitting device may have structures such as the following: substrate/first electrode/ light emitting unit/charge generation layer (n type)/charge generation layer (p type)/light emitting unit/second electrode; substrate/first electrode/charge generation layer (n type)/charge generation layer (p type)/light emitting unit/ second electrode; substrate/first electrode/light emitting unit/charge generation layer (n type)/charge generation layer (p type)/second electrode, and the like. Here, the number of light emitting units employed may be two, three, or more, as necessary. The light emitting unit may comprise a light emitting layer, and may further comprise one or more layers from among a hole injection layer, a hole transport layer, an electron blocking layer, a hole blocking layer, an electron transport layer, and an electron injection layer, as necessary.

Specifically, the compound of the present disclosure may be used as a material for the light emitting layer, the hole blocking layer, the electron transport layer, or the electron injection layer in the organic light emitting device.

When the compound of the present disclosure is used as a material for the light emitting layer, the compound of the present disclosure may serve as a light emitting host, wherein the light emitting layer may further include a dopant. For example, the compound of the present disclosure may be used as an n-type phosphorescent host.

Further, as a dopant capable of being used together with the represented compound of the present disclosure, any of those known in the art may be applied. For example, when the compound of the present disclosure is used as a phosphorescent host, the phosphorescent dopant used together may be a complex of transition metals. Specifically, the phosphorescent dopant may be a complex of iridium (Ir), platinum (Pt), osmium (Os), gold (Au), titanium (Ti), zirconium (Zr), hafnium (Hf), europium (Eu), terbium (Tb) or thulium (Tm), and more specifically, may be at least one selected from the group of $Ir(ppy)_3$, $Ir(ppy)_2(acac)$, $Ir(mppy)_3$, $Ir(mpp)_2(acac)$, $F_2Irpic$, $(F_2ppy)_2Ir(tmd)$, $Ir(ppy)_2tmd$, $Ir(pmi)_3$, $Ir(pmb)_3$, FCNIr, FCNIrpic, $FIr_6$, $FIrN_4$, FIrpic, PtOEP, $Ir(chpy)_3$, P0-01 ($C_{31}H_{23}IrN_2O_2S_2$), $Ir(ppz)_3$, and $Ir(dfppz)_3$, but is not limited thereto.

Except for the inclusion of the compound of the present disclosure in one or more layers, the organic light emitting device may be manufactured using the materials and methods known in the art. Further, the compound of the present disclosure may independently constitute one or more layers of the organic material layer of the organic light emitting device; however, as necessary, it may be mixed with other materials to constitute the organic material layer.

In the organic light emitting device, the materials used other than the compound of the present disclosure are exemplified below; however, these materials are provided by way of example and are not intended to limit the scope of the present disclosure, and the materials may be replaced with other materials known in the art.

Specifically, the first electrode may be an anode and the second electrode may be a cathode.

As the anode material, materials having a relatively large work function may be used, and a transparent conductive oxide, a metal, a conductive polymer, or the like, may be used. Specific examples of the anode material may include metals such as vanadium, chromium, copper, zinc and gold, or alloys thereof; metal oxides such as zinc oxide, indium oxide, indium tin oxide (ITO), and indium zinc oxide (IZO); combinations of oxides with metals such as ZnO:Al or $SnO_2$:Sb; conductive polymers such as poly(3-methylthiophene), poly[3,4-(ethylene-1,2-dioxy)thiophene] (PEDOT), polypyrrole, polyaniline, and the like, but the anode material is not limited thereto.

As the cathode material, materials having a relatively low work function may be used, and a metal, a metal oxide, a conductive polymer, or the like, may be used. Specific examples of the cathode material include metals such as magnesium, calcium, sodium, potassium, titanium, indium, yttrium, lithium, ytterbium, gadolinium, aluminum, silver, tin and lead, or alloys thereof; multilayer structured materials such as LiF/Al, $LiO_2$/Al, LiF/Mg:Ag, LiF/Mg:Ag/Ag, and the like, but the cathode material is not limited thereto.

As the hole injection material, any hole injection material known in the art may be used. For example, phthalocyanine compounds such as copper phthalocyanine disclosed in U.S. Pat. No. 4,356,429; starburst type amine derivatives described in the document entitled [Advanced Material, 6, p.677 (1994)] such as tris(4-carbazoyl-9-ylphenyl)amine (TCTA), 4,4',4"-tri[phenyl(m-tolyl)amino]triphenylamine (m-MTDATA), and 1,3,5-tris[4-(3-methylphenylphenylamino)phenyl]benzene (m-MTDAPB); or soluble conductive polymers such as polyaniline/dodecylbenzenesulfonic acid, poly(3,4-ethylenedioxythiophene)/poly(4-styrenesulfonate)), polyaniline/camphor sulfonic acid, polyaniline/poly(4-styrene-sulfonate), or the like, may be used. However, the hole injection material is not limited thereto.

As the hole transport material, a pyrazoline derivative, an arylamine derivative, a stilbene derivative, a triphenyldiamine derivative, or the like, may be used, and materials of low or high molecular weight may be used. However, the hole transport material is not limited thereto.

As the electron transport material, a metal complex of an oxadiazole derivative, anthraquinodimethane or a derivative thereof, benzoquinone or a derivative thereof, naphthoquinone or a derivative thereof, anthraquinone or a derivative thereof, tetracyanoanthraquinodimethane or a derivative thereof, a fluorenone derivative, diphenyldicyanoethylene or a derivative thereof, a diphenoquinone derivative, 8-hydroxyquinoline or a derivative thereof, and the like, may be used, and not only materials of low molecular weight but also high molecular weight may be used, but the electron transport material is not limited thereto.

As the electron injection material, for example, LiF is generally used in the art, but the electron injection material is not limited thereto.

As the light emitting material, red, green or blue light emitting material may be used, and if necessary, two or more light emitting materials may be mixed for use. Further, the light emitting material may be a fluorescent material, but may also be a phosphorescent material. As the light emitting material, a material that emits light by coupling the holes and electrons injected from the anode and cathode, respectively, may be used alone, but materials in which both a host material and a dopant material are involved in light emission may also be used.

The organic light emitting device may be a front emission type, a back emission type, or a double-sided emission type, depending on the material to be used.

The compound according to the present disclosure may also be applied in other organic electronic devices including organic solar cells, organic photoconductors, organic transistors, and the like, on a principle similar to a case where the compound is applied to the organic light emitting device.

Electronic Equipment

Further, the electronic equipment according to the present disclosure comprises the organic light emitting device described above.

For example, the electronic equipment may be a display. Specifically, the electronic equipment may be a display having one or more structures selected from the group consisting of an RGB OLED, a white OLED, a soluble OLED, and a quantum dot light emitting diode (QLED), but is not limited thereto.

The RGB OLED is an organic light emitting display device with a light emitting layer comprising sub pixels emitting red light (R), sub pixels emitting green light (G), and sub pixels emitting blue light (B), and which may also comprise an electron injection layer, an electron transport layer, a light emitting layer, a hole injection layer, a hole transport layer, and the like. For example, the RGB OLED may comprise a form in which the electron injection layer, the electron transport layer, the light emitting layer, the hole transport layer, and the hole injection layer are sequentially stacked. As another example, the RGB OLED may comprise a form in which the hole injection layer, the hole transport layer, the electron blocking layer, the light emitting layer, the electron transport layer, and the electron injection layer are sequentially stacked.

Meanwhile, the white OLED (WOLED) is a white organic light emitting display device, which is a full color display device employing a thin light source, a liquid crystal display backlight, or a color filter. For example, the white OLED generally has a tandem (stacked) structure, and the light emitting layer comprising each stack may be formed of a plurality of layers having different colors. Here, an electron transport layer may be applied to each light emitting layer unit. In the case of two stacks, two electron transport layers may be applied thereto, and in the case of three stacks, three electron transport layers may be applied thereto. In addition, the role of the common layer is of significant importance in determining the difference in charge injection characteristics of the charge generation layer (CGL) formed for each stack. In particular, the electron transport layer has a bonding surface with n-CGL, having a great influence on the electron injection characteristics, and thereby greatly affecting the characteristics of the device.

Further, the soluble OLED, along with the WOLED, has been developed as a representative next-generation model of a large area OLED panel, of which a hybrid type soluble OLED is representative. A hybrid type soluble OLED may be manufactured through the solution process by applying a soluble material from an anode to a light emitting layer, and by applying a deposition material from an electron transport layer to a cathode. In particular, the interfacial property between the light emitting material of the solution process and the electron transport material of the deposition type is one of important technical issues determining the device characteristics. Therefore, it is important to develop an electron transport material suitable for the solution process.

Next, the QLED is a display device that implements full color by forming the light emitting layer using quantum dots. Further, materials for the common layer, excluding the light emitting layer, are composed to have a concept similar to that of the OLED element, and also have a driving principle similar thereto.

In addition, the electronic equipment of the present disclosure may be of various sizes, such as mobile devices, TVs, and the like.

BEST MODE FOR CARRYING OUT THE INVENTION

Hereinafter, the present specification is described in more detail with reference to Examples; however, these Examples are merely provided to illustrate the present application and are not intended to limit the scope of the present disclosure.

PREPARATION EXAMPLES

Preparation Example 1

1) Preparation of Compound 1-1

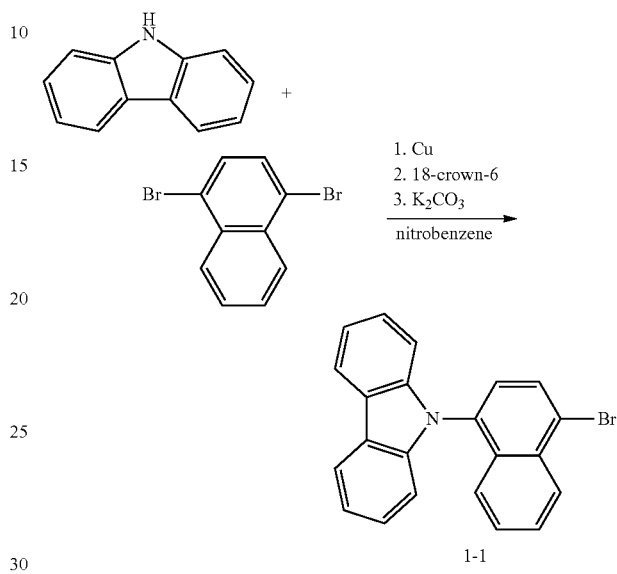

A 2 L round-bottom flask was charged with 39 g (233.24 mmol, 1 eq) of 9H-carbazole, 100 g (349.85 mmol, 1.5 eq) of 1,4-dibromonaphthalene, 3 g (46.65 mmol, 0.2 eq) of copper(Cu), 31 g (116.62 mmol, 0.5 eq) of 18-crown-6, and 64.5 g (446.48 mmol, 2 eq) of potassium carbonate ($K_2CO_3$), then 1,000 ml of nitrobenzene was added thereto, and the mixture was stirred under reflux.

After completion of the reaction, the nitrobenzene was distilled off under reduced pressure, the reaction mixture was extracted with dichloromethane($CH_2Cl_2$)/water($H_2O$), and the $CH_2Cl_2$ layer was then dried over magnesium sulfate($MgSO_4$). Purification was performed using a silica-gel column to obtain 71.2 g of Compound 1-1 at a yield of 82%.

2) Preparation of Compound 1-2

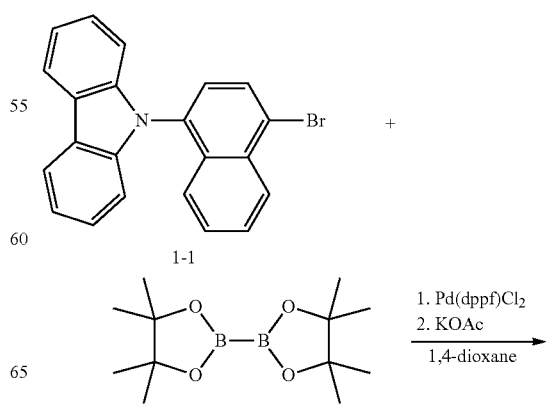

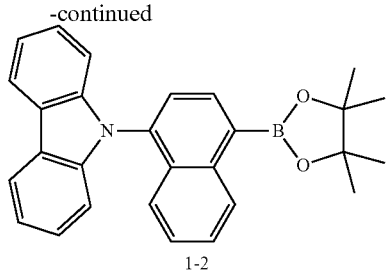

1-2

A 500 mL round-bottom flask was charged with 15 g (40.29 mmol, 1 eq) of Compound 1-1, 15 g (60.44 mmol, 1.5 eq) of bis(pinacolato)diboron, 1.5 g (2.01 mmol, 0.05 eq) of Pd(dppf)Cl2([1,1'-Bis(diphenylphosphino)ferrocene]dichloropalladium(II)), and 16 g (161.17 mmol, 4 eq) of KOAc, then 300 ml of 1,4-dioxane was added, and the mixture was stirred under reflux.

After completion of the reaction, the reaction mixture was extracted with CH$_2$Cl$_2$/H$_2$O, and the CH$_2$Cl$_2$ layer was dried over MgSO$_4$. Purification was performed using a silica-gel column to obtain 15.1 g of Compound 1-2 at a yield of 89%.

3) Preparation of Compound 1-3

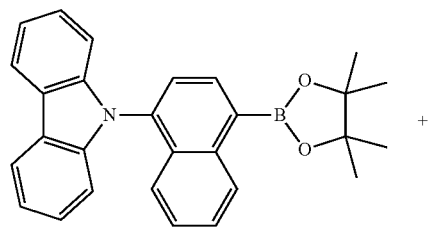

A 1 L round-bottom flask was charged with 14 g (33.39 mmol, 1 eq) of Compound 1-2, 19 g (66.77 mmol, 2 eq) of 4-bromo-iodobenzene, 1.9 g (1.67 mmol, 0.05 eq) of Pd(PPh$_3$)$_4$(Tetrakis(triphenylphosphine)palladium), and 14 g (100.16 mmol, 3 eq) of K$_2$CO$_3$, then 350 ml of tetrahydrofuran (THF) and 70 ml of H$_2$O were added, and the mixture was stirred under reflux.

After completion of the reaction, the reaction mixture was extracted with CH$_2$Cl$_2$/H$_2$O, and the CH$_2$Cl$_2$ layer was dried over MgSO$_4$. Purification was performed using a silica-gel column to obtain 12.6 g of Compound 1-3 at a yield of 84%.

4) Preparation of Compound 1-4

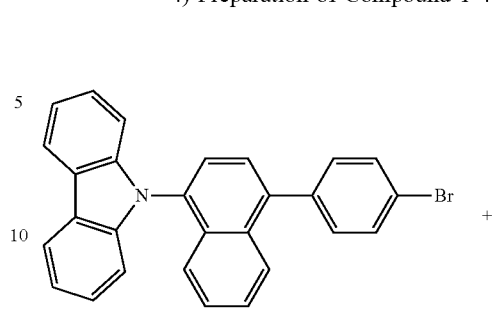

1-4

A 500 mL round-bottom flask was charged with 12 g (26.76 mmol, 1 eq) of Compound 1-3, 10.2 g (40.15 mmol, 1.5 eq) of bis(pinacolato)diboron, 1 g (1.34 mmol, 0.05 eq) of Pd(dppf)Cl$_2$, and 10.5 g (107.06 mmol, 4 eq) of KOAc, then 150 ml of 1,4-dioxane was added, and the mixture was stirred under reflux.

After completion of the reaction, the reaction mixture was extracted with CH$_2$Cl$_2$/H$_2$O, and the CH$_2$Cl$_2$ layer was dried over MgSO$_4$. Purification was performed using a silica-gel column to obtain 11.9 g of Compound 1-4 at a yield of 90%.

5) Preparation of Compound 1

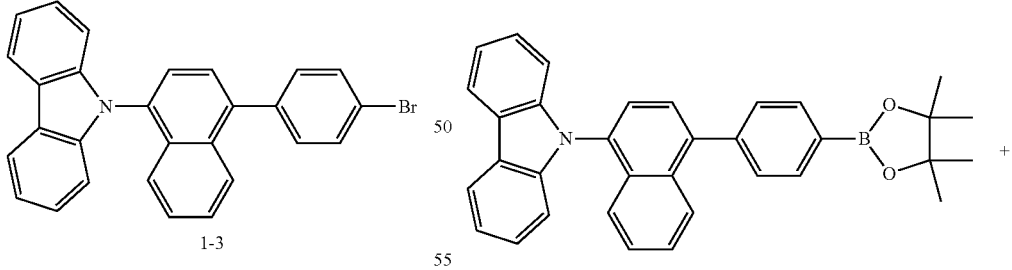

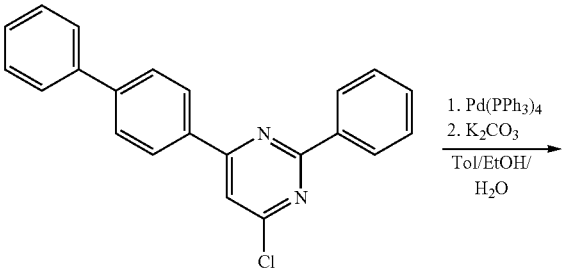

-continued

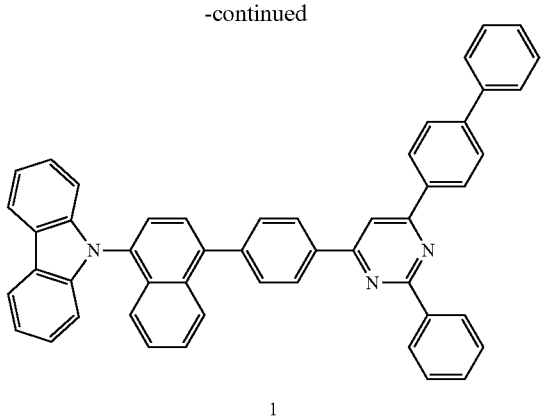

1

A 500 mL round-bottom flask was charged with 10 g (20.18 mmol, 1 eq) of Compound 1-4, 7 g (20.18 mmol, 1 eq) of 4-([1,1'-Biphenyl]-4-yl)-6-chloro-2-phenylpyrimidine, 1.2 g (1.01 mmol, 0.05 eq) of Pd(PPh$_3$)$_4$, and 8.4 g (60.55 mmol, 3 eq) of K$_2$CO$_3$, then 100 ml of toluene (Tol), 20 ml of ethanol (EtOH) and 20 ml of H$_2$O were added, and the mixture was stirred under reflux.

After completion of the reaction, the reaction mixture was extracted with CH$_2$Cl$_2$/H$_2$O, and the CH$_2$Cl$_2$ layer was dried over MgSO$_4$. Purification was performed using a silica-gel column to obtain 10.8 g of Compound 1 at a yield of 79%.

6) Preparation of Compound C-1

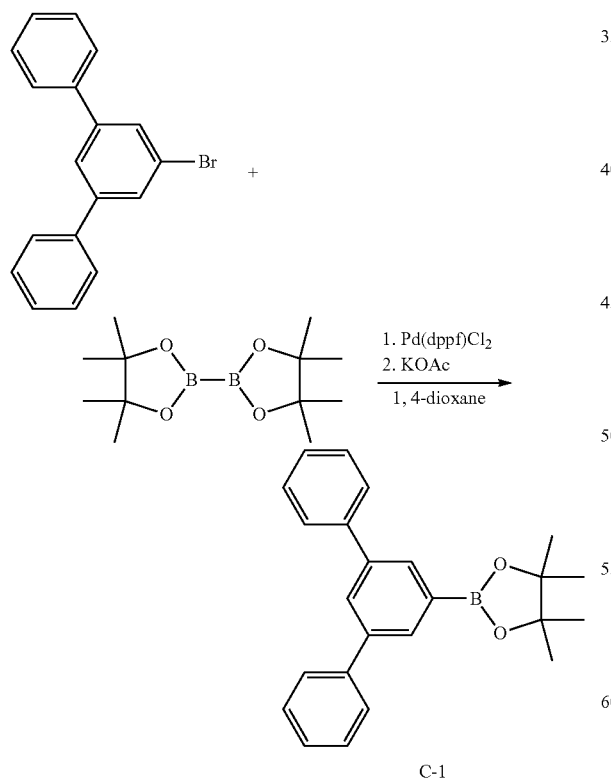

A 500 mL round-bottom flask was charged with 150 g (485.11 mmol, 1 eq) of 5'-Bromo-m-terphenyl, 184.78 g (727.66 mmol, 1.5 eq) of bis(pinacolato)diboron, 17.7 g (24.26 mmol, 0.05 eq) of Pd(dppf)Cl$_2$, and 190.4 g (1940.43 mmol, 4 eq) of KOAc, then 2 L of 1,4-dioxane was added, and the mixture was stirred under reflux.

After completion of the reaction, the reaction mixture was extracted with CH$_2$Cl$_2$/H$_2$O, and the CH$_2$Cl$_2$ layer was dried over MgSO$_4$. Purification was performed using a silica-gel column to obtain 138 g of Compound C-1 at a yield of 80%.

7) Preparation of Compound C-2

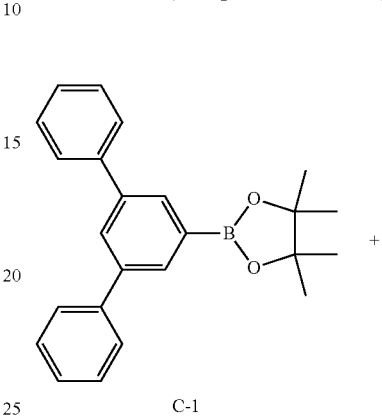

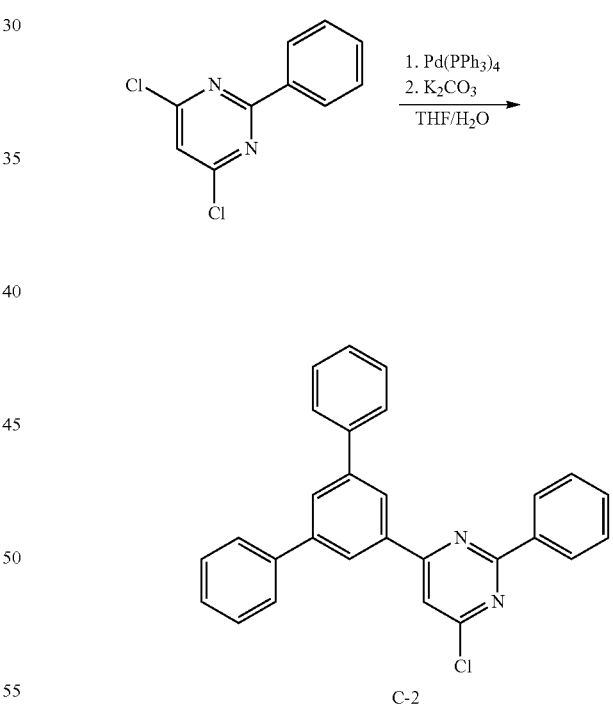

A 1 L round-bottom flask was charged with 50 g (140.34 mmol, 1 eq) of Compound C-1, 47.4 g (210.51 mmol, 1.5 eq) of 4,6-Dichloro-2-phenylpyrimidine, 8.1 g (7.02 mmol, 0.05 eq) of Pd(PPh$_3$)$_4$, and 58.2 g (421.03 mmol, 3 eq) of K$_2$CO$_3$, then 1500 ml of THF and 300 ml of H$_2$O were added, and the mixture was stirred under reflux.

After completion of the reaction, the reaction mixture was extracted with CH$_2$Cl$_2$/H$_2$O, and the CH$_2$Cl$_2$ layer was dried over MgSO$_4$. Purification was performed using a silica-gel column to obtain 36.2 g of Compound C-2 at a yield of 62%.

8) Preparation of Compound 2

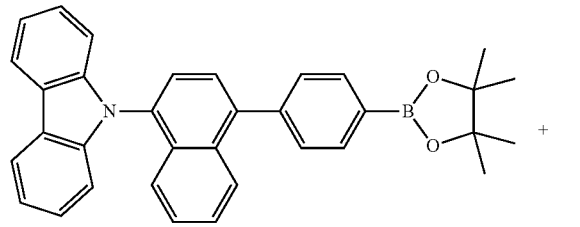

1-4

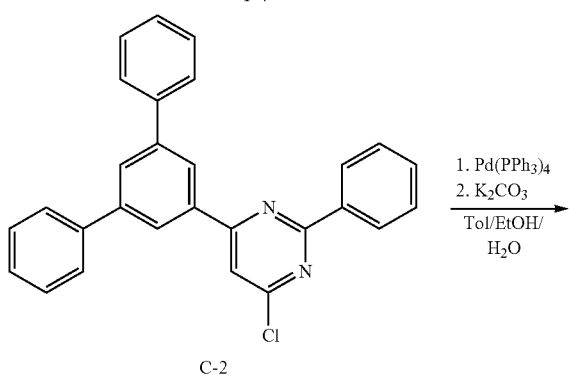

C-2

1. Pd(PPh₃)₄
2. K₂CO₃

Tol/EtOH/H₂O

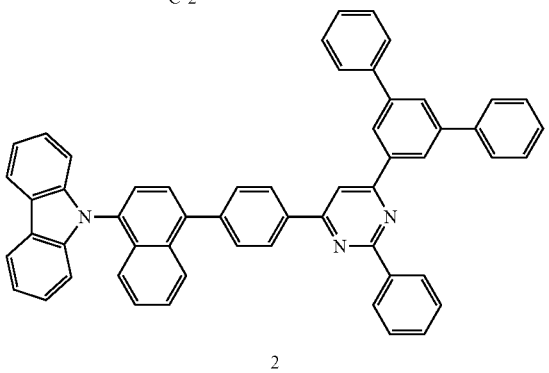

2

A 1 L round-bottom flask was charged with 10 g (20.19 mmol, 1 eq) of Compound 1-4, 8.5 g (20.19 mmol, 1 eq) of Compound C-2, 1.2 g (1.01 mmol, 0.05 eq) of Pd(PPh₃)₄, and 8.4 g (60.55 mmol, 3 eq) of K₂CO₃, then 150 ml of Toluene, 30 mL of EtOH and 30 ml of H₂O were added, and the mixture was stirred under reflux.

After completion of the reaction, the reaction mixture was extracted with CH₂Cl₂/H₂O, and the CH₂Cl₂ layer was dried over MgSO₄. Purification was performed using a silica-gel column to obtain 12.8 g of Compound 2 at a yield of 84%.

9) Preparation of Compound 3-1

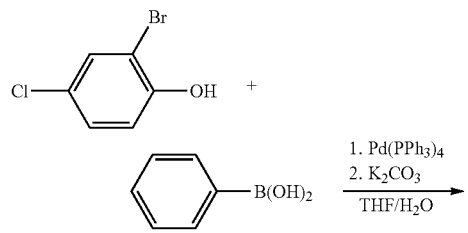

1. Pd(PPh₃)₄
2. K₂CO₃

THF/H₂O

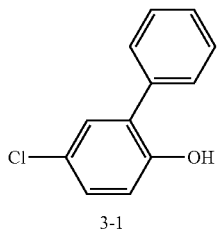

3-1

A 3 L round-bottom flask was charged with 120 g (578.45 mmol, 1 eq) of 2-Bromo-4-chlorophenol, 78 g (636.29 mmol, 1.1 eq) of Phenylboronic acid, 34 g (28.92 mmol, 0.05 eq) of Pd(PPh₃)₄, and 240 g (1735.36 mmol, 3 eq) of K₂CO₃, then 2000 ml of THF and 400 ml of H₂O were added, and the mixture was stirred under reflux.

After completion of the reaction, the reaction mixture was extracted with CH₂Cl₂/H₂O, and the CH₂Cl₂ layer was dried over MgSO₄. Purification was performed using a silica-gel column to obtain 81.3 g of Compound 3-1 at a yield of 69%.

10) Preparation of Compound 3-2

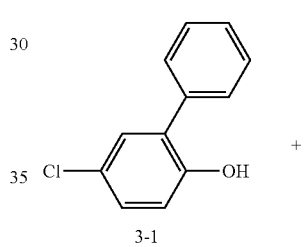

3-1

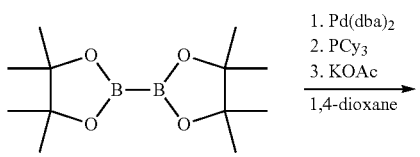

1. Pd(dba)₂
2. PCy₃
3. KOAc 1,4-dioxane

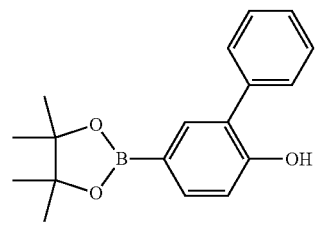

3-2

A 3 L round-bottom flask was charged with 85 g (415.34 mmol, 1 eq) of Compound 3-1, 158.2 g (623.02 mmol, 1.5 eq) of bis(pinacolato)diboron, 11.9 g (20.77 mmol, 0.05 eq) of Pd(dba)₂(Tris(dibenzylideneacetone)dipalladium(0)), 11.7 g (41.53 mmol, 0.1 eq) of Tricyclohexylphosphine, and 163 g (1661.37 mmol, 4 eq) of KOAc, then 2 L of 1,4-dioxane was added, and the mixture was stirred under reflux.

After completion of the reaction, the reaction mixture was extracted with CH₂Cl₂/H₂O, and the CH₂Cl₂ layer was dried over MgSO₄. Purification was performed using a silica-gel column to obtain 98.1 g of Compound 3-2 at a yield of 80%.

11) Preparation of Compound 3-3

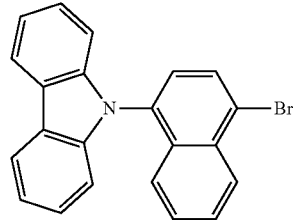

1-1

+

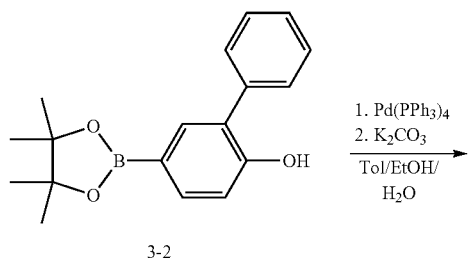

3-2

→ 1. Pd(PPh₃)₄ 2. K₂CO₃ Tol/EtOH/H₂O

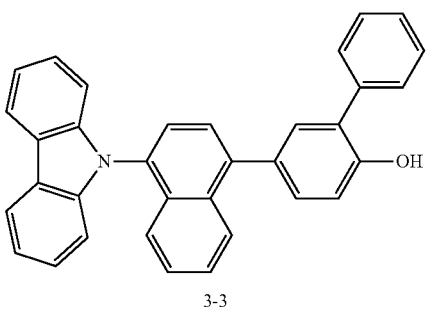

3-3

A 1 L round-bottom flask was charged with 10 g (26.86 mmol, 1 eq) of Compound 1-1, 8 g (26.86 mmol, 1 eq) of Compound 3-2, 1.6 g (1.34 mmol, 0.05 eq) of Pd(PPh₃)₄, and 11.1 g (80.59 mmol, 3 eq) of K₂CO₃, then 150 ml of Toluene, 30 mL of EtOH and 30 ml of H₂O were added, and the mixture was stirred under reflux.

After completion of the reaction, the reaction mixture was extracted with CH₂Cl₂/H₂O, and the CH₂Cl₂ layer was dried over MgSO₄. Purification was performed using a silica-gel column to obtain 8.1 g of Compound 3-3 at a yield of 65%.

12) Preparation of Compound 3-4

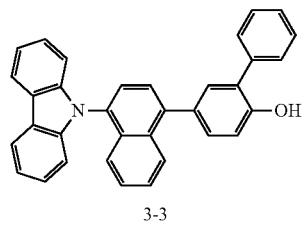

3-3

→ 1. Trifluoromethanesulfonic anhydride 2. Triethylamine CH₂Cl₂

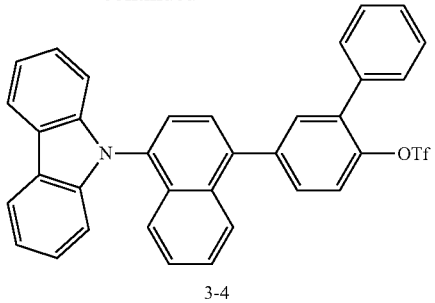

3-4

A 250 ml round-bottom flask was charged with 4.6 g (10.0 mmol, 1 eq) of Compound 3-3 and 50 ml of CH₂Cl₂, and the mixture was cooled to a temperature of 0° C. Next, 2 g (19.93 mmol, 2 eq) of Triethylamine and 4.2 g (14.95 mmol, 1.5 eq) of Trifluoromethanesulfonic anhydride were added, and the mixture was raised to room temperature and then stirred.

After completion of the reaction, the reaction mixture was extracted with CH₂Cl₂/H₂O, and the CH₂Cl₂ layer was dried over MgSO₄. Purification was performed using a silica-gel column to obtain 5.1 g of Compound 3-4 at a yield of 86%.

13) Preparation of Compound 3-5

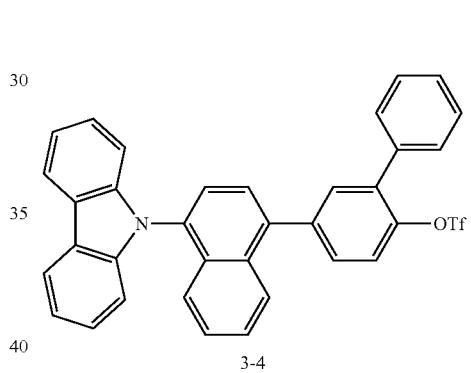

3-4

→ 1. Pd(dba)₂ 2. PCy₃ 3. KOAc 1,4-dioxane

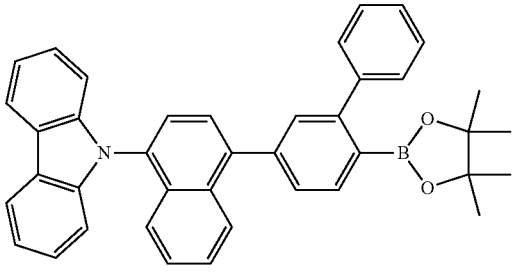

3-5

A 250 mL round-bottom flask was charged with 5 g (8.42 mmol, 1 eq) of Compound 3-4, 3.2 g (12.63 mmol, 1.5 eq) of bis(pinacolato)diboron, 0.2 g (0.42 mmol, 0.05 eq) of Pd(dba)₂, 0.2 g (0.84 mmol, 0.1 eq) of PCy₃, and 3.3 g (33.69 mmol, 4 eq) of KOAc, then 100 ml of 1,4-dioxane was added, and the mixture was stirred under reflux.

After completion of the reaction, the reaction mixture was extracted with CH₂Cl₂/H₂O, and the CH₂Cl₂ layer was dried over MgSO₄. Purification was performed using a silica-gel column to obtain 4.1 g of Compound 3-5 at a yield of 85%.

14) Preparation of Compound 3

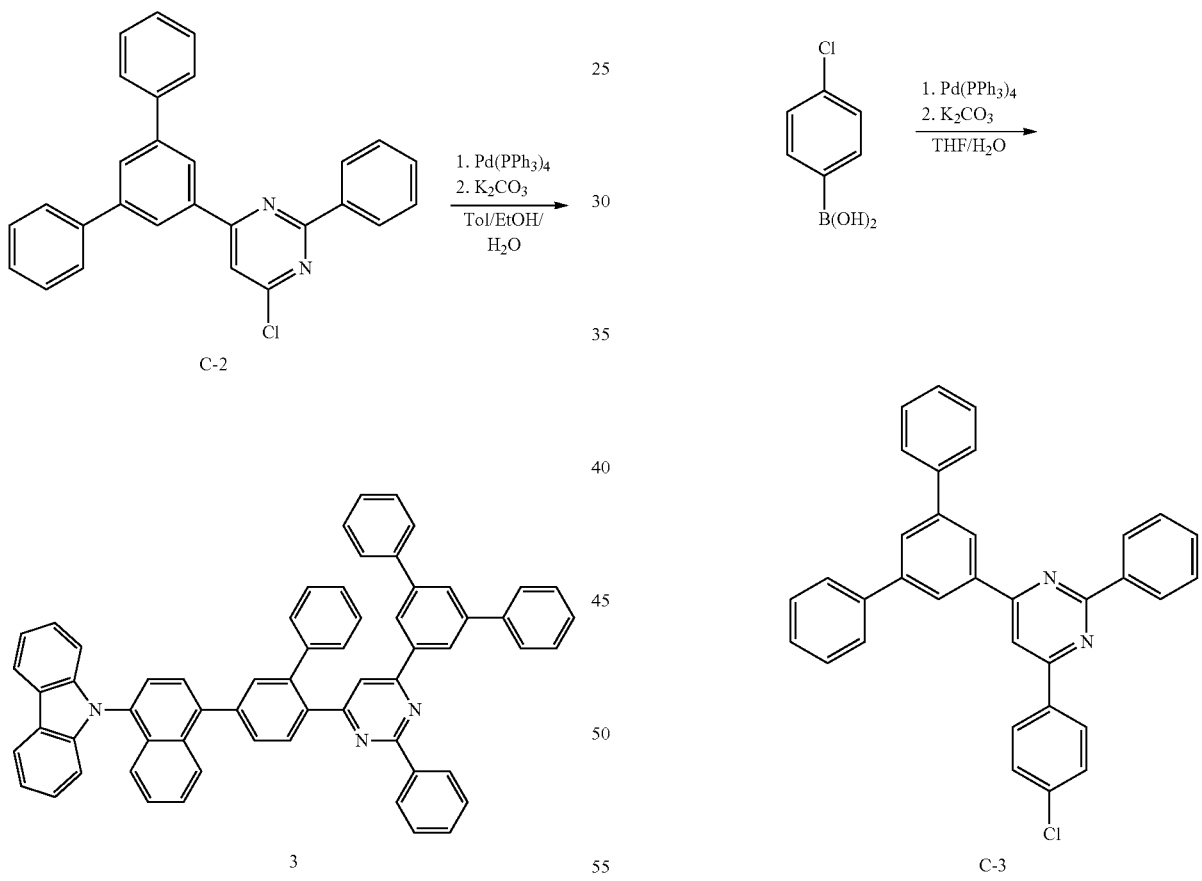

A 1 L round-bottom flask was charged with 3.4 g (5.95 mmol, 1 eq) of Compound 3-5, 2.5 g (5.95 mmol, 1 eq) of Compound C-2, 0.3 g (0.30 mmol, 0.05 eq) of Pd(PPh₃)₄, and 2.5 g (17.85 mmol, 3 eq) of K₂CO₃, then 100 ml of Toluene, 20 mL of EtOH and 30 ml of H₂O were added, and the mixture was stirred under reflux.

After completion of the reaction, the reaction mixture was extracted with CH₂Cl₂/H₂O, and the CH₂Cl₂ layer was dried over MgSO₄. Purification was performed using a silica-gel column to obtain 4.1 g of Compound 3 at a yield of 84%.

15) Preparation of Compound C-3

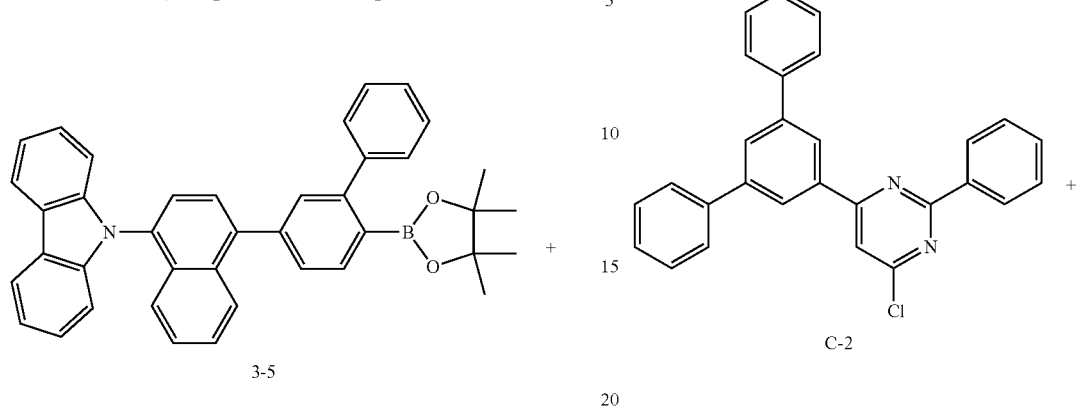

A 1 L round-bottom flask was charged with 12.4 g (29.60 mmol, 1 eq) of Compound C-2, 4.8 g (31.08 mmol, 1.05 eq) of 4-chlorophenylboronic acid, 1.7 g (1.48 mmol, 0.05 eq) of Pd(PPh₃)₄, and 12.3 g (88.80 mmol, 3 eq) of K₂CO₃, then 300 ml of THF and 60 ml of H₂O were added, and the mixture was stirred under reflux.

After completion of the reaction, the reaction mixture was extracted with CH₂Cl₂/H₂O, and the CH₂Cl₂ layer was dried over MgSO₄. Purification was performed using a silica-gel column to obtain 11.9 g of Compound C-3 at a yield of 81%.

16) Preparation of Compound C-4

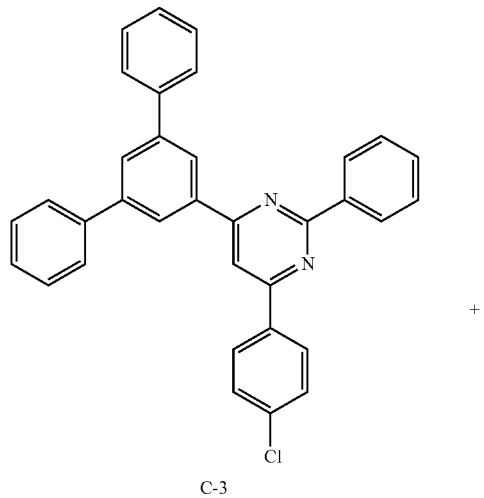

C-3

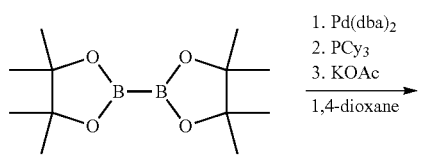

1. Pd(dba)₂
2. PCy₃
3. KOAc 1,4-dioxane

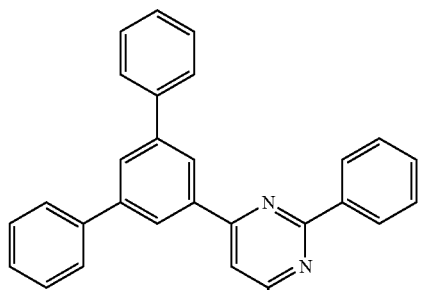

C-4

A 250 ml round-bottom flask was charged with 11 g (22.22 mmol, 1 eq) of Compound C-3, 8.5 g (33.33 mmol, 1.5 eq) of bis(pinacolato)diboron, 0.6 g (1.11 mmol, 0.05 eq) of Pd(dba)₂, 0.6 g (2.22 mmol, 0.1 eq) of PCy₃, and 8.7 g (88.88 mmol, 4 eq) of KOAc, then 110 ml of 4-dioxane was added, and the mixture was stirred under reflux.

After completion of the reaction, the reaction mixture was extracted with CH₂Cl₂/H₂O, and the CH₂Cl₂ layer was dried over MgSO₄. Purification was performed using a silica-gel column to obtain 11.8 g of Compound C-4 at a yield of 91%.

17) Preparation of Compound 4-1

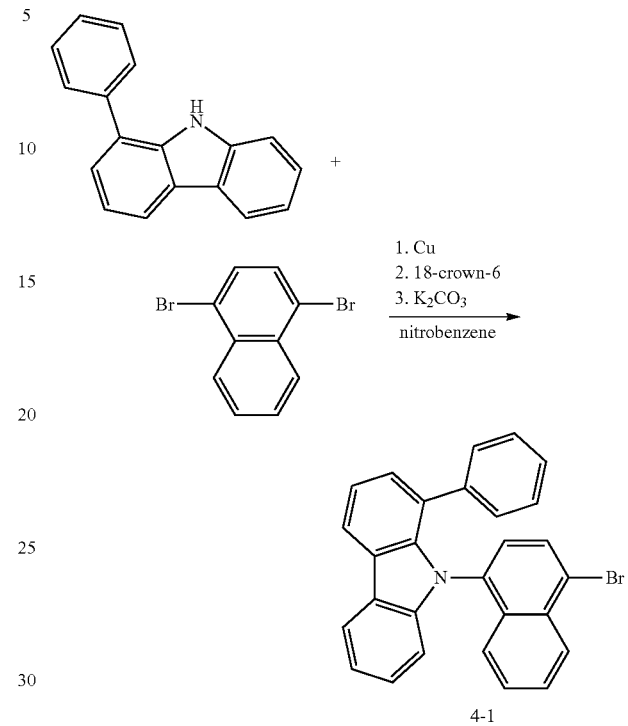

4-1

A 1 L round-bottom flask was charged with 14 g (57.61 mmol, 1 eq) of 1-Phenyl-9H-carbazole, 33 g (115.22 mmol, 2 eq) of 1,4-dibromonaphthalene, 14.5 g (230.45 mmol, 4 eq) of Cu, 9.1 g (34.56 mmol, 0.6 eq) of 18-crown-6, and 15.9 g (115.08 mmol, 2 eq) of K₂CO₃, then 600 ml of nitrobenzene was added, and the mixture was stirred under reflux.

After completion of the reaction, the nitrobenzene was distilled off under reduced pressure, then the reaction mixture was extracted with CH₂Cl₂/H₂O, and the CH₂Cl₂ layer was dried over MgSO₄. Purification was performed using a silica-gel column to obtain 11.3 g of Compound 4-1 at a yield of 44%.

18) Preparation of Compound 4

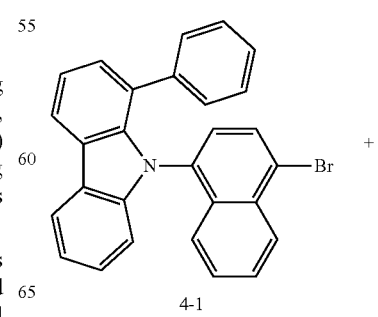

4-1

-continued

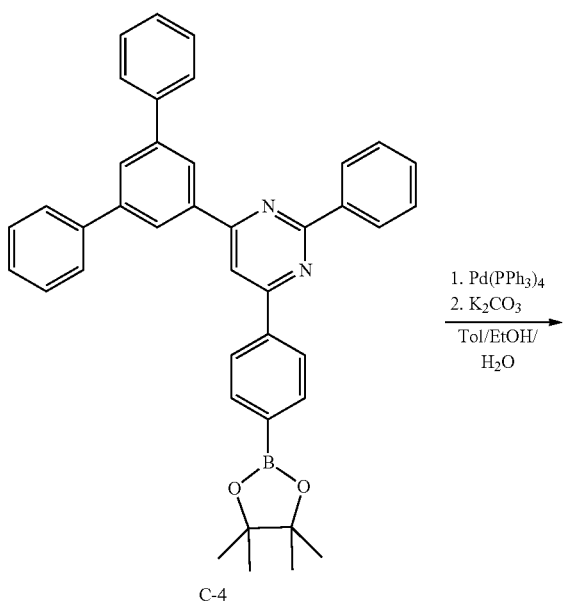

C-4

1. Pd(PPh₃)₄
2. K₂CO₃
Tol/EtOH/H₂O
→

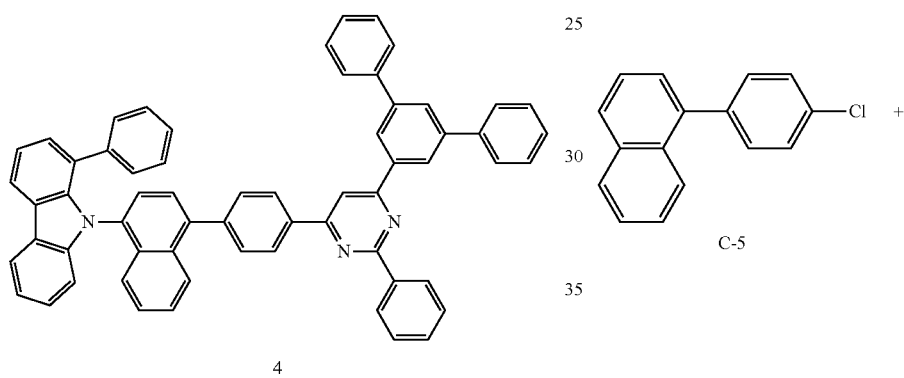

4

A 1 L round-bottom flask was charged with 5.1 g (10.91 mmol, 1 eq) of Compound 4-1, 6.4 g (10.91 mmol, 1 eq) of Compound C-4, 0.63 g (0.54 mmol, 0.05 eq) of Pd(PPh₃)₄, and 4.5 g (32.76 mmol, 3 eq) of K₂CO₃, then 100 ml of Toluene, 20 mL of EtOH and 20 ml of H₂O were added, and the mixture was stirred under reflux.

After completion of the reaction, the reaction mixture was extracted with CH₂Cl₂/H₂O, and the CH₂Cl₂ layer was dried over MgSO₄. Purification was performed using a silica-gel column to obtain 7.8 g of Compound 4 at a yield of 83%.

19) Preparation of Compound C-5

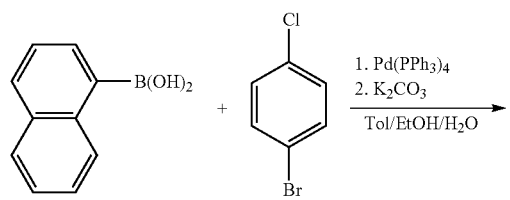

1. Pd(PPh₃)₄
2. K₂CO₃
Tol/EtOH/H₂O
→

-continued

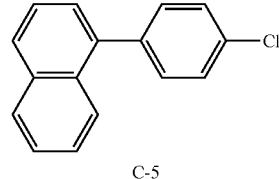

C-5

A 1 L round-bottom flask was charged with 10 g (58.14 mmol, 1 eq) of Naphthalene-1-boronic acid, 13 g (69.77 mmol, 1.2 eq) of 1-Bromo-4-chlorobenzene, 3.4 g (2.91 mmol, 0.05 eq) of Pd(PPh₃)₄, and 24 g (174.43 mmol, 3 eq) of K₂CO₃, then 300 ml of Toluene, 60 mL of EtOH and 60 ml of H₂O were added, and the mixture was stirred under reflux.

After completion of the reaction, the reaction mixture was extracted with CH₂Cl₂/H₂O, and the CH₂Cl₂ layer was dried over MgSO₄. Purification was performed using a silica-gel column to obtain 13 g of Compound C-5 at a yield of 94%.

20) Preparation of Compound C-6

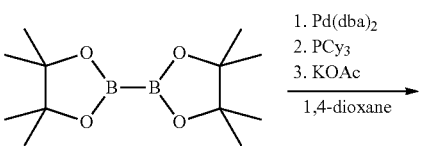

C-5

1. Pd(dba)₂
2. PCy₃
3. KOAc
1,4-dioxane
→

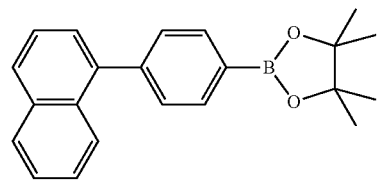

C-6

A 1 L round-bottom flask was charged with 13 g (54.46 mmol, 1 eq) of Compound C-5, 21 g (81.69 mmol, 1.5 eq) of bis(pinacolato)diboron, 1.5 g (2.72 mmol, 0.05 eq) of Pd(dba)₂, 1.5 g (5.44 mmol, 0.1 eq) of PCy₃, and 21 g (217.83 mmol, 4 eq) of KOAc, then 300 ml of 1,4-dioxane was added, and the mixture was stirred under reflux.

After completion of the reaction, the reaction mixture was extracted with CH₂Cl₂/H₂O, and the CH₂Cl₂ layer was dried over MgSO₄. Purification was performed using a silica-gel column to obtain 14 g of Compound C-6 at a yield of 78%.

21) Preparation of Compound C-7

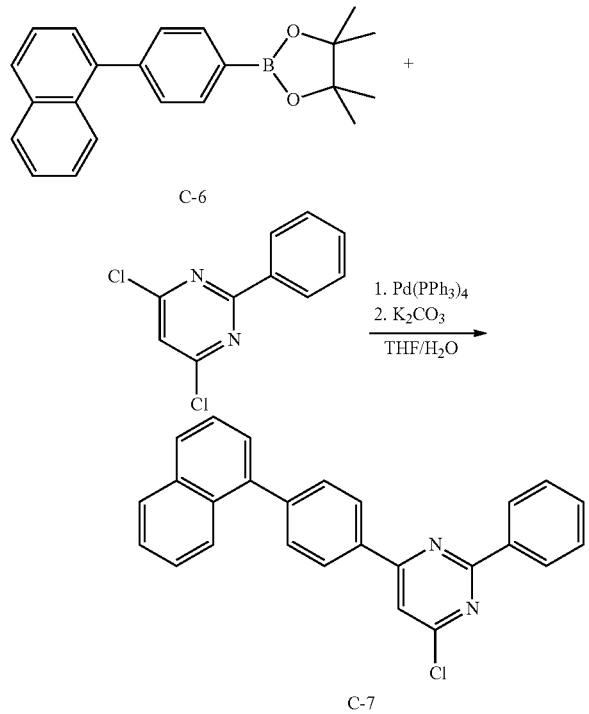

A 1 L round-bottom flask was charged with 14 g (42.39 mmol, 1 eq) of Compound C-6, 19 g (84.78 mmol, 2 eq) of 4,6-Dichloro-2-phenylpyrimidine, 2.5 g (2.12 mmol, 0.05 eq) of Pd(PPh₃)₄, and 18 g (127.18 mmol, 3 eq) of K₂CO₃, then 400 ml of THF and 80 ml of H₂O were added, and the mixture was stirred under reflux.

After completion of the reaction, the reaction mixture was extracted with CH₂Cl₂/H₂O, and the CH₂Cl₂ layer was dried over MgSO₄. Purification was performed using a silica-gel column to obtain 10.1 g of Compound C-7 at a yield of 61%.

22) Preparation of Compound 5

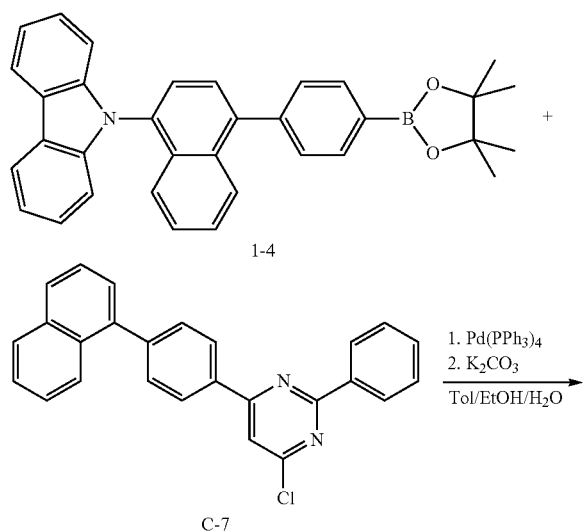

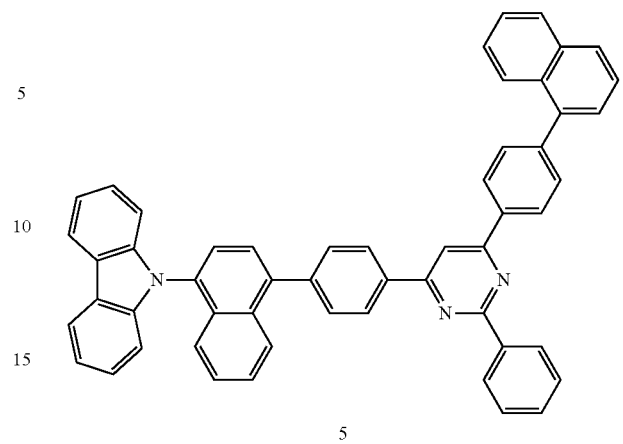

A 500 mL round-bottom flask was charged with 10 g (20.19 mmol, 1 eq) of Compound 1-4, 7.9 g (20.19 mmol, 1 eq) of Compound C-7, 1.2 g (1.01 mmol, 0.05 eq) of Pd(PPh₃)₄, and 8.4 g (60.55 mmol, 3 eq) of K₂CO₃, then 100 ml of Toluene, 20 mL of EtOH and 20 ml of H₂O were added, and the mixture was stirred under reflux.

After completion of the reaction, the reaction mixture was extracted with CH₂Cl₂/H₂O, and the CH₂Cl₂ layer was dried over MgSO₄. Purification was performed using a silica-gel column to obtain 10.3 g of Compound 5 at a yield of 70%.

23) Preparation of Compound C-8

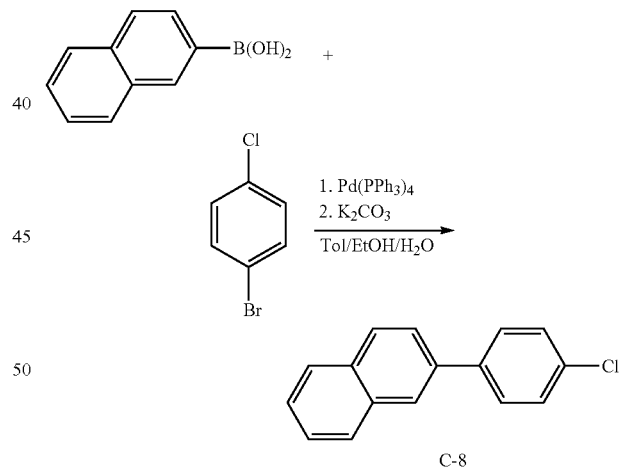

A 1 L round-bottom flask was charged with 10 g (58.14 mmol, 1 eq) of Naphthalene-2-boronic acid, 13 g (69.77 mmol, 1.2 eq) of 1-Bromo-4-chlorobenzene, 3.4 g (2.91 mmol, 0.05 eq) of Pd(PPh₃)₄, and 24 g (174.43 mmol, 3 eq) of K₂CO₃, then 300 ml of Toluene, 60 mL of EtOH and 60 ml of H₂O were added, and the mixture was stirred under reflux.

After completion of the reaction, the reaction mixture was extracted with CH₂Cl₂/H₂O, and the CH₂Cl₂ layer was dried over MgSO₄. Purification was performed using a silica-gel column to obtain 13.3 g of Compound C-8 at a yield of 96%.

24) Preparation of Compound C-9

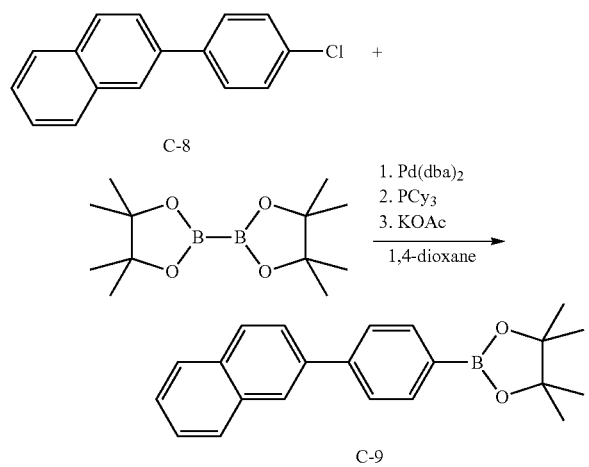

A 1 L round-bottom flask was charged with 13 g (54.46 mmol, 1 eq) of Compound C-8, 21 g (81.69 mmol, 1.5 eq) of bis(pinacolato)diboron, 1.5 g (2.72 mmol, 0.05 eq) of Pd(dba)$_2$, 1.5 g (5.44 mmol, 0.1 eq) of PCy$_3$, and 21 g (217.83 mmol, 4 eq) of KOAc, then 300 ml of 1,4-dioxane was added, and the mixture was stirred under reflux.

After completion of the reaction, the reaction mixture was extracted with CH$_2$Cl$_2$/H$_2$O, and the CH$_2$Cl$_2$ layer was dried over MgSO$_4$. Purification was performed using a silica-gel column to obtain 15.1 g of Compound C-9 at a yield of 84%.

25) Preparation of Compound C-10

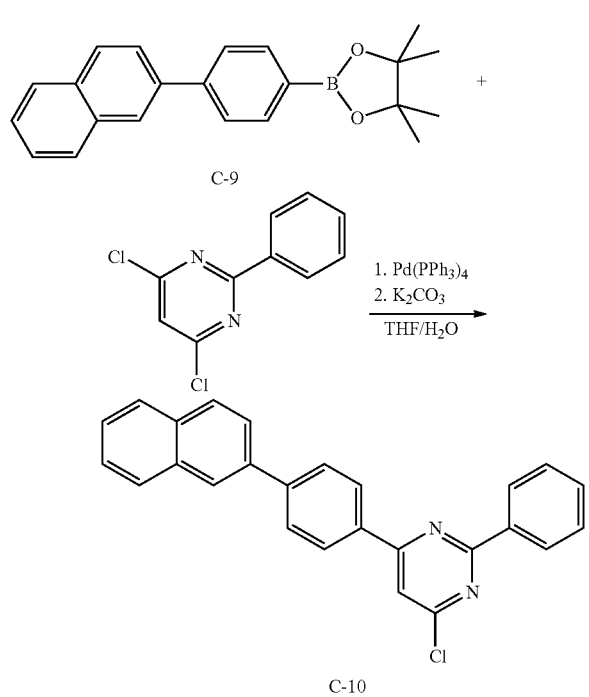

A 1 L round-bottom flask was charged with 14 g (42.39 mmol, 1 eq) of Compound C-9, 19 g (84.78 mmol, 2 eq) of 4,6-Dichloro-2-phenylpyrimidine, 2.5 g (2.12 mmol, 0.05 eq) of Pd(PPh$_3$)$_4$, and 18 g (127.18 mmol, 3 eq) of K$_2$CO$_3$, then 400 ml of THF and 80 ml of H$_2$O were added, and the mixture was stirred under reflux.

After completion of the reaction, the reaction mixture was extracted with CH$_2$Cl$_2$/H$_2$O, and the CH$_2$Cl$_2$ layer was dried over MgSO$_4$. Purification was performed using a silica-gel column to obtain 12.8 g of Compound C-10 at a yield of 77%.

26) Preparation of Compound 6

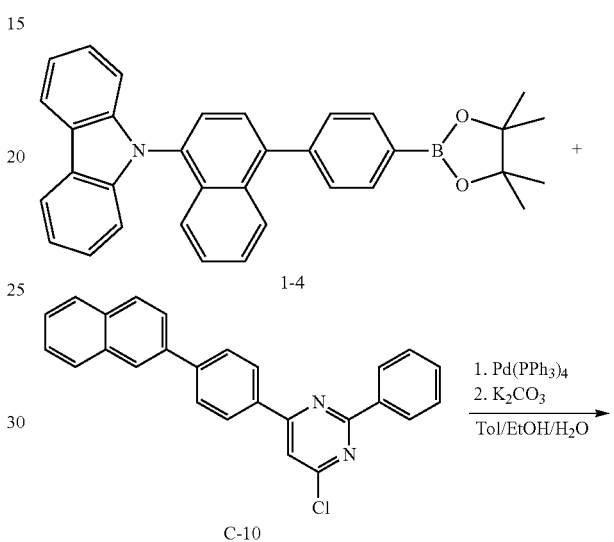

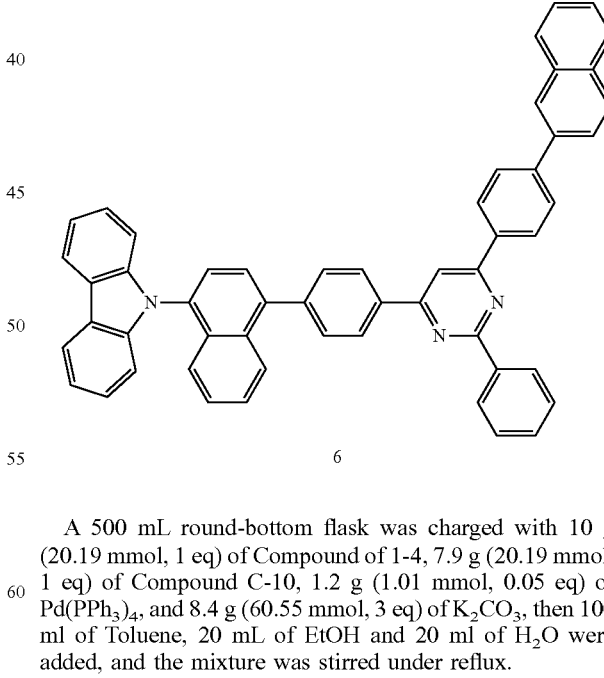

A 500 mL round-bottom flask was charged with 10 g (20.19 mmol, 1 eq) of Compound of 1-4, 7.9 g (20.19 mmol, 1 eq) of Compound C-10, 1.2 g (1.01 mmol, 0.05 eq) of Pd(PPh$_3$)$_4$, and 8.4 g (60.55 mmol, 3 eq) of K$_2$CO$_3$, then 100 ml of Toluene, 20 mL of EtOH and 20 ml of H$_2$O were added, and the mixture was stirred under reflux.

After completion of the reaction, the reaction mixture was extracted with CH$_2$Cl$_2$/H$_2$O, and the CH$_2$Cl$_2$ layer was dried over MgSO$_4$. Purification was performed using a silica-gel column to obtain 11.1 g of Compound 6 at a yield of 76%.

27) Preparation of Compound C-11

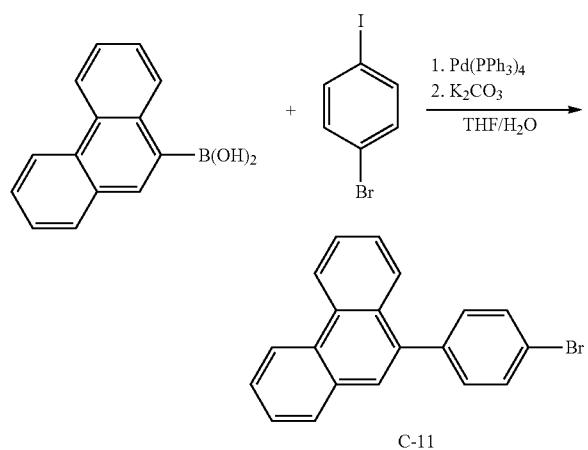

A 3 L round-bottom flask was charged with 50 g (225.17 mmol, 1 eq) of 9-Phenanthracenylboronic acid, 127.4 g (450.35 mmol, 2 eq) of 1-Bromo-4-iodobenzene, 13 g (11.26 mmol, 0.05 eq) of Pd(PPh$_3$)$_4$, and 93.4 g (675.52 mmol, 3 eq) of K$_2$CO$_3$, then 2000 ml of THF and 400 ml of H$_2$O were added, and the mixture was stirred under reflux.

After completion of the reaction, the reaction mixture was extracted with CH$_2$Cl$_2$/H$_2$O, and the CH$_2$Cl$_2$ layer was dried over MgSO$_4$. Purification was performed using a silica-gel column to obtain 39.5 g of Compound C-11 at a yield of 53%.

28) Preparation of Compound C-12

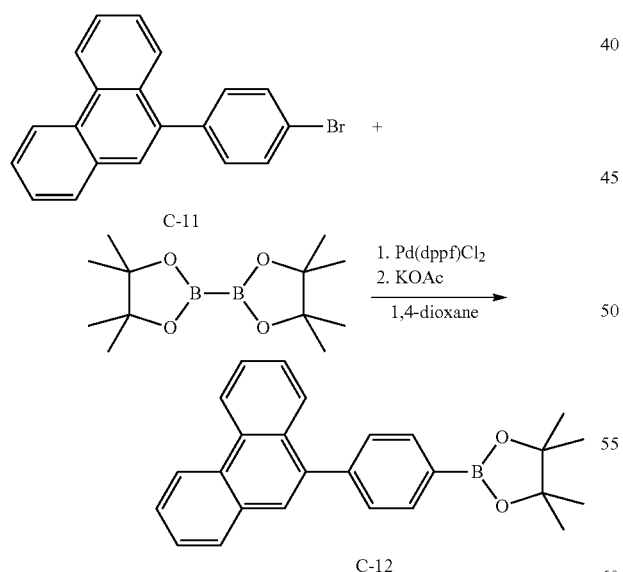

A 3 L round-bottom flask was charged with 39.5 g (118.54 mmol, 1 eq) of Compound C-11, 45.15 g (177.81 mmol, 1.5 eq) of bis(pinacolato)diboron, 4.33 g (5.93 mmol, 0.05 eq) of Pd(dppf)Cl$_2$, and 34.9 g (355.62 mmol, 3 eq) of KOAc, then 2 L of 1,4-dioxane was added, and the mixture was stirred under reflux.

After completion of the reaction, the reaction mixture was extracted with CH$_2$Cl$_2$/H$_2$O, and the CH$_2$Cl$_2$ layer was dried over MgSO$_4$. Purification was performed using a silica-gel column to obtain 41.7 g of Compound C-12 at a yield of 93%.

29) Preparation of Compound C-13

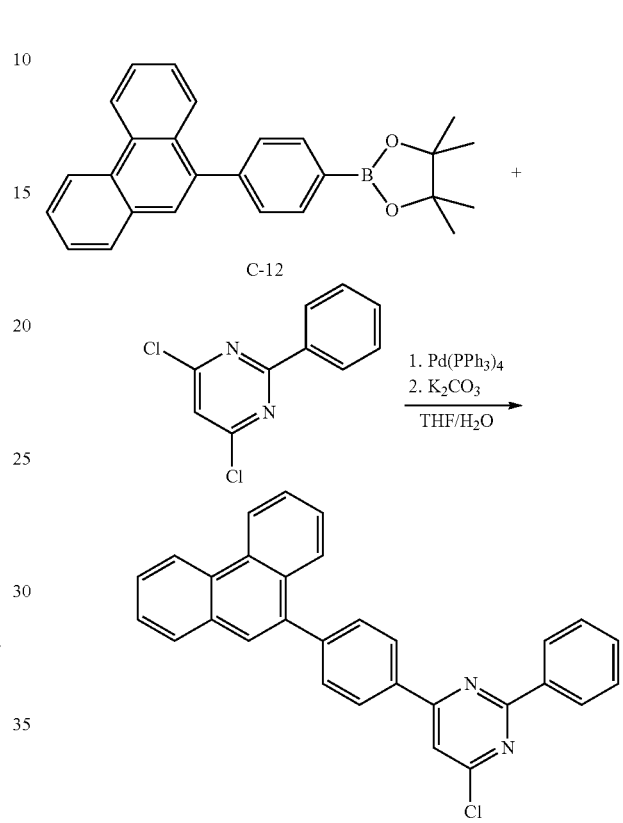

A 1 L round-bottom flask was charged with 30 g (78.89 mmol, 1 eq) of Compound C-12, 26.8 g (118.33 mmol, 1.5 eq) of 4,6-Dichloro-2-phenylpyrimidine, 4.6 g (3.94 mmol, 0.05 eq) of Pd(PPh$_3$)$_4$, and 32.7 g (236.67 mmol, 3 eq) of K$_2$CO$_3$, then 780 ml of THF and 160 ml of H$_2$O were added, and the mixture was stirred under reflux.

After completion of the reaction, the reaction mixture was extracted with CH$_2$Cl$_2$/H$_2$O, and the CH$_2$Cl$_2$ layer was dried over MgSO$_4$. Purification was performed using a silica-gel column to obtain 21.5 g of Compound C-13 at a yield of 62%.

30) Preparation of Compound 7

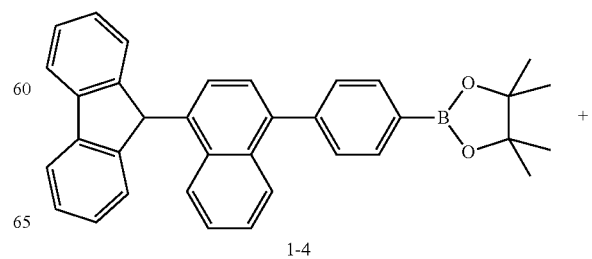

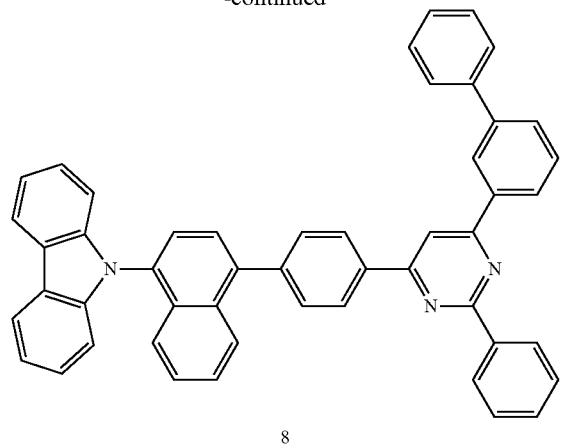

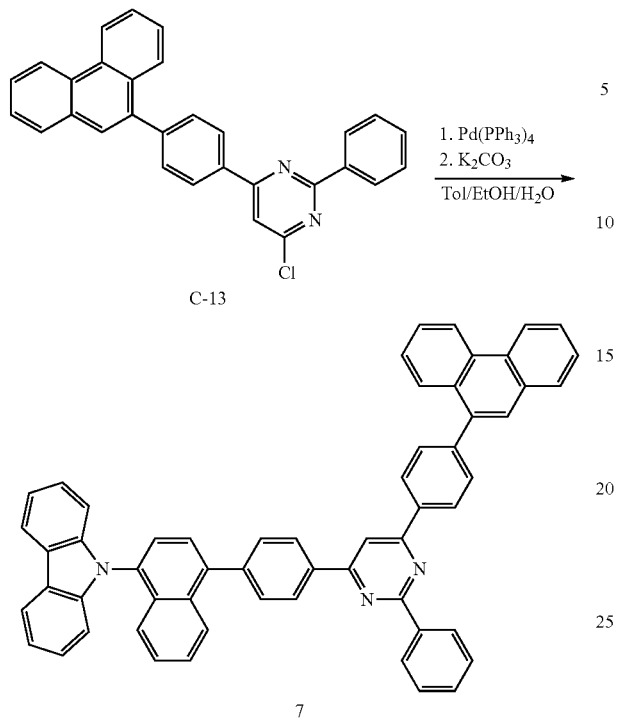

A 500 ml round-bottom flask was charged with 10 g (20.19 mmol, 1 eq) of Compound 1-4, 8.9 g (20.19 mmol, 1 eq) of Compound C-13, 1.2 g (1.01 mmol, 0.05 eq) of Pd(PPh₃)₄, and 8.4 g (60.55 mmol, 3 eq) of K₂CO₃, then 100 ml of Toluene, 20 mL of EtOH and 20 ml of H₂O were added, and the mixture was stirred under reflux.

After completion of the reaction, the reaction mixture was extracted with CH₂Cl₂/H₂O, and the CH₂Cl₂ layer was dried over MgSO₄. Purification was performed using a silica-gel column to obtain 12.4 g of Compound 7 at a yield of 79%.

31) Preparation of Compound 8

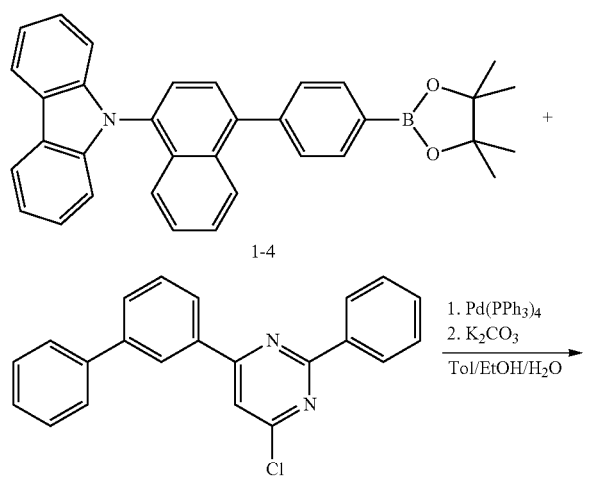

A 500 ml round-bottom flask was charged with 10 g (20.18 mmol, 1 eq) of Compound 1-4, 7 g (20.18 mmol, 1 eq) of 4-([1,1'-Biphenyl]-3-yl)-6-chloro-2-phenylpyrimidine, 1.2 g (1.01 mmol, 0.05 eq) of Pd(PPh₃)₄, and 8.4 g (60.55 mmol, 3 eq) of K₂CO₃, then 100 ml of Toluene, 20 mL of EtOH and 20 ml of H₂O were added, and the mixture was stirred under reflux.

After completion of the reaction, the reaction mixture was extracted with CH₂Cl₂/H₂O, and the CH₂Cl₂ layer was dried over MgSO₄. Purification was performed using a silica-gel column to obtain 11.6 g of Compound 8 at a yield of 85%.

32) Preparation of Compound C-14

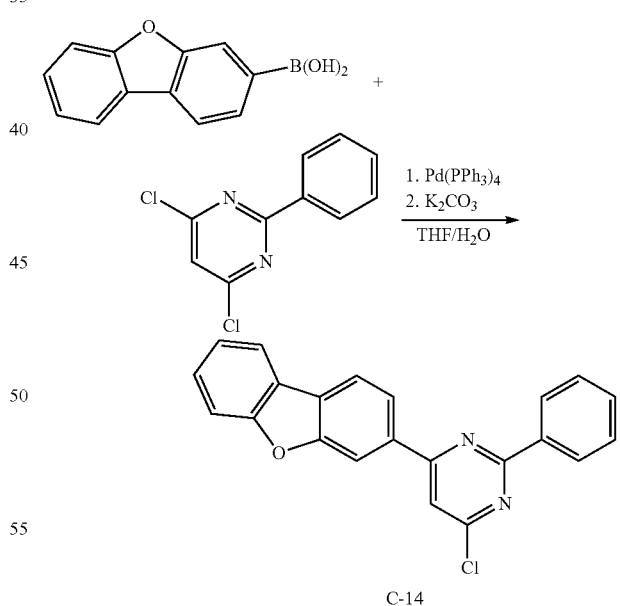

A 2 L round-bottom flask was charged with 20 g (94.34 mmol, 1 eq) of 3-Dibenzofuranboronic acid, 31.9 g (141.50 mmol, 1.5 eq) of 4,6-Dichloro-2-phenylpyrimidine, 5.5 g (4.72 mmol, 0.05 eq) of Pd(PPh₃)₄, and 39.1 g (283.01 mmol, 3 eq) of K₂CO₃, then 1000 ml of THF and 200 ml of H₂O were added, and the mixture was stirred under reflux.

After completion of the reaction, the reaction mixture was extracted with CH₂Cl₂/H₂O, and the CH₂Cl₂ layer was dried over MgSO₄. Purification was performed using a silica-gel column to obtain 17.8 g of Compound C-14 at a yield of 53%.

33) Preparation of Compound 9

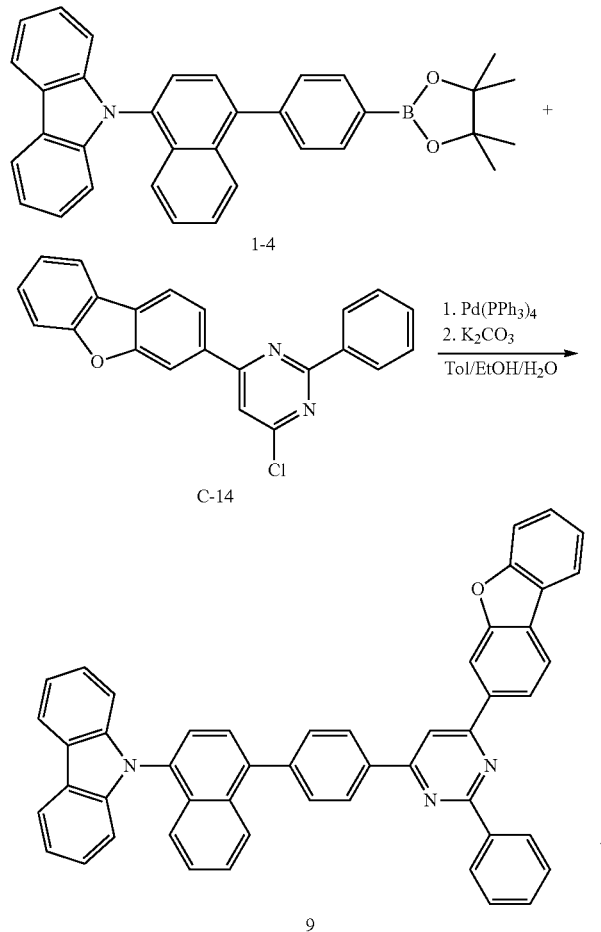

A 500 mL round-bottom flask was charged with 10 g (20.19 mmol, 1 eq) of Compound 1-4, 7.2 g (20.19 mmol, 1 eq) of Compound C-14, 1.2 g (1.01 mmol, 0.05 eq) of Pd(PPh₃)₄, and 8.4 g (60.55 mmol, 3 eq) of K₂CO₃, then 100 ml of Toluene, 20 mL of EtOH and 20 ml of H₂O were added, and the mixture was stirred under reflux.

After completion of the reaction, the reaction mixture was extracted with CH₂Cl₂/H₂O, and the CH₂Cl₂ layer was dried over MgSO₄. Purification was performed using a silica-gel column to obtain 10.3 g of Compound 9 at a yield of 74%.

The Compounds were prepared in the same manner as in the above Preparation Examples, and the results of confirmation of synthesis are shown in Tables 1 to 3 below.

TABLE 1

| | ¹H NMR (CDCl₃), 500 MHz | ¹³C NMR (CDCl₃), 126 MHz |
|---|---|---|
| Compound 1 | 8.81 (dd, J = 8.18, 1.59 Hz, 2H), 8.49 (d, J = 8.30 Hz, 2H), 8.41 (d, J = 8.54 Hz, 2H), 8.23 (d, J = 7.08 Hz, 2H), 8.15 (s, 1H), 8.12 (d, J = 8.54 Hz, 1H), 7.81 (dd, J = 8.42, 3.54 Hz, 4H), 7.75-7.63 (m, 4H), 7.61-7.46 (m, 6H), 7.44-7.27 (m, 7H) 7.10 (d, J = 8.06 Hz, 2H) | 164.61, 164.41, 164.33, 143.62, 142.75, 142.15, 140.48, 140.26, 138.10, 136.88, 136.28, 133.88, 132.79, 131.20, 130.73, 130.71, 128.92, 128.51, 128.50, 127.87, 127.73, 127.61, 127.41, 127.17, 126.99, 126.98, 126.94, 126.61, 126.28, 125.97, 123.89, 123.23, 120.34, 119.83, 110.26, 110.15 |
| Compound 2 | 8.80 (dd, J = 8.06, 1.46 Hz, 2H), 8.51-8.46 (m, 4H), 8.22 (d, J = 7.81 Hz, 2H), 8.19 (s, 1H), 8.11 (d, J = 8.54 Hz, 1H), 7.97 (t, J = 1.59 Hz, 1H), 7.80 (d, J = 8.30 Hz, 2H), 7.77 (dd, J = 8.18, 1.10 Hz, 4H), 7.70 (d, J = 7.32 Hz, 1H), 7.65 (d, J = 7.32 Hz, 1H), 7.60-7.48 (m, 8H), 7.46-7.41 (m, 2H), 7.40-7.28 (m, 6H), 7.09 (d, J = 8.06 Hz, 2H) | 164.85, 164.68, 164.43, 142.81, 142.63, 142.17, 140.81, 140.47, 138.67, 138.01, 136.78, 133.90, 132.79, 131.20, 130.79, 130.70, 128.95, 128.59, 128.56, 128.52, 127.80, 127.46, 127.43, 126.99, 126.98, 126.94, 126.61, 126.28, 125.97, 125.13, 123.89, 123.24, 120.37, 119.84, 110.61, 110.26 |
| Compound 3 | 8.66 (dd, J = 7.81, 1.95 Hz, 2 H) 8.31 (d, J = 8.06 Hz, 1 H) 8.23-8.19 (m, 3 H) 7.98 (d, J = 1.71 Hz, 2 H) 7.89 (t, J = 1.71 Hz, 1 H) 7.82 (dd, J = 7.81, 1.95 Hz, 1 H) 7.79 (d, J = 1.71 Hz, 1 H) 7.71 (d, J = 1.71 Hz, 2 H) 7.69-7.66 (m, 4 H) 7.55-7.51 (m, 6 H) 7.50 (s, 1 H) 7.47-7.44 (m, 3 H) 7.43-7.40 (m, 2 H) 7.39-7.37 (m, 4 H) 7.36-7.28 (m, 6 H) 7.09 (d, J = 7.81 Hz, 2 H) | 166.17, 164.67, 163.10, 142.34, 142.17, 141.93, 141.78, 141.09, 140.61, 140.31, 138.53, 138.00, 136.68, 133.93, 132.83, 132.58, 131.20, 130.87, 130.68, 129.87, 129.68, 128.82, 128.68, 128.47, 128.45, 128.19, 127.75, 127.66, 127.40, 127.10, 127.05, 126.95, 126.65, 126.28, 125.97, 124.99, 123.89, 123.24, 120.33, 119.83, 116.34, 110.25 |
| Compound 4 | 8.95 (dd, 2 H) 8.35 (d, 2 H) 8.31-8.25 (m, 4 H) 8.23 (s, 1H), 8.17 (d, 2H), 8.10-8.04 (m, 4H), 7.94 (dd, 2 H) 7.75 (d, 2 H) 7.71 (d, 2 H) 7.56-7.46 (m, 4H) 7.41-7.37 (m, 6 H) 7.35-7.19 (m, 8 H) 7.16 (d, 2 H) | 165.98, 164.61, 164.15, 142.45, 142.33, 142.07, 141.85, 140.98, 140.89, 140.22, 138.66, 137.54, 135.55, 134.71, 134.04, 133.73, 133.50, 131.18, 130.88, 130.81, 129.29, 129.10, 128.98, 128.70, 128.51, 128.49, 128.05, 127.66, 127.58, 127.50, 127.17, 127.09, 126.75, 126.34, 126.26, 125.88, 124.79, 123.81, 122.85, 121.46, 120.37, 119.87, 119.46, 119.15, 109.54, 105.47, |
| Compound 5 | 8.83 (dd, J = 8.18, 1.34 Hz, 2 H), 8.53 (d, J = 8.30 Hz, 2 H), 8.47 (d, J = 8.54 Hz, 2 H), 8.23 (d, J = 7.08 Hz, 2 H), 8.22 (s, 1 H), 8.13 (d, J = 8.54 Hz, 1 H), 7.99 (d, J = 8.54 Hz, 1 H), 7.94 (d, J = 8.54 Hz, 1 H), 7.91 (d, J = 8.06 Hz, 1 H), 7.83 (d, J = 8.30 Hz, 2 H), 7.70-7.75 (m, 3 H), 7.68 (d, J = 7.57 Hz, 1 H), 7.55-7.61 (m, 4 H), 7.50-7.55 (m, 3 H), 7.46-7.50 (m, 1 H), 7.35-7.41 (m, 4 H), 7.29-7.34 (m, 2 H), 7.11 (d, J = 8.06 Hz, 2 H) | 164.70, 164.63, 164.41, 143.49, 142.82, 142.18, 140.49, 139.42, 138.10, 136.90, 136.43, 133.91, 133.82, 132.80, 131.42, 131.22, 130.78, 130.75, 130.74, 130.71, 128.54, 128.52, 128.39, 128.10, 127.44, 127.28, 127.01, 127.00, 126.95, 126.62, 126.29, 126.28, 125.97, 125.94, 125.82, 125.41, 123.90, 123.25, 120.34, 119.84, 110.30, 110.26 |
| Compound 6 | 8.82 (dd, J = 8.30, 1.46 Hz, 2 H), 8.53 (d, J = 8.30 Hz, 2 H), 8.48 (d, J = 8.54 Hz, 2 H), 8.24 (d, J = 7.57 Hz, 2 H), 8.21 (s, 1 H), 8.17 (d, J = 0.98 Hz, 1 H), 8.13 (d, J = 8.54 Hz, 1 H), 7.91 (d, J = 7.08 Hz, 1 H), 7.94- | 164.69, 164.46, 164.42, 143.58, 142.81, 142.19, 140.52, 138.14, 137.60, 136.95, 136.39, 133.93, 133.64, 132.89, 132.83, 131.23, 130.77, 130.76, 128.66, 128.54, 128.53, 128.32, 127.90, 127.85, |

TABLE 1-continued

| | $^1$H NMR (CDCl$_3$), 500 MHz | $^{13}$C NMR (CDCl$_3$), 126 MHz |
|---|---|---|
| | 8.00 (m, 4 H), 7.82-7.87 (m, 3 H), 7.72 (dd, J = 10.98, 5.37 Hz, 2 H), 7.50-7.62 (m, 6 H), 7.31-7.41 (m, 6 H), 7.12 (d, J = 8.06 Hz, 2 H) | 127.70, 127.46, 127.01, 127.00, 126.96, 126.64, 126.49, 126.31, 126.29, 126.08, 125.98, 125.33, 123.92, 123.26, 120.35, 119.85, 110.28, 110.22 |
| Compound 7 | 8.84 (dd, J = 8.30, 1.46 Hz, 2 H), 8.81 (d, J = 8.79 Hz, 1 H), 8.75 (d, J = 8.06 Hz, 1 H), 8.53 (d, J = 8.54 Hz, 2 H), 8.49 (d, J = 8.30 Hz, 2 H), 8.21-8.26 (m, 3 H), 8.13 (d, J = 8.54 Hz, 1 H), 8.00 (dd, J = 8.30, 0.98 Hz, 1 H), 7.93 (dd, J = 8.06, 1.22 Hz, 1 H), 7.83 (d, J = 8.54 Hz, 2 H), 7.76-7.79 (m, 3 H), 7.67-7.73 (m, 4 H), 7.62-7.66 (m, 1 H), 7.55-7.62 (m, 4 H), 7.52 (ddd, J = 8.48, 6.53, 1.59 Hz, 1 H), 7.30-7.41 (m, 6 H), 7.11 (d, J = 8.06 Hz, 2 H) | 164.71, 164.61, 164.44, 143.54, 142.82, 142.18, 140.49, 138.10, 137.99, 136.90, 136.56, 133.92, 132.81, 131.43, 131.22, 130.82, 130.79, 130.75, 130.71, 130.69, 130.68, 130.09, 128.76, 128.54, 128.53, 127.63, 127.45, 127.32, 127.01, 127.00, 126.97, 126.95, 126.85, 126.75, 126.66, 126.64, 126.30, 125.98, 123.90, 123.25, 123.02, 122.58, 120.35, 119.84, 110.31, 110.27 |
| Compound 8 | 8.80 (dd, J = 8.18, 1.59 Hz, 2 H), 8.54 (t, J = 1.59 Hz, 1 H), 8.51 (d, J = 8.30 Hz, 2 H), 8.32 (dt, J = 7.69, 1.40 Hz, 1 H), 8.24 (d, J = 7.57 Hz, 2 H), 8.19 (s, 1H), 8.12 (d, J = 8.54 Hz, 1 H), 7.83 (d, J = 8.30 Hz, 2 H), 7.79 (dt, J = 7.63, 1.43 Hz, 1 H), 7.76-7.71 (m, 3 H), 7.70-7.65 (m, 2 H), 7.61-7.50 (m, 6 H), 7.45-7.41 (m, 1 H), 7.40-7.30 (m, 6 H), 7.11 (d, J = 8.30 Hz, 2 H) | 164.91. 164.69, 164.45, 142.83, 142.19, 142.13, 140.87, 140.50, 138.12, 138.07, 136.87, 133.92, 132.81, 131.22, 130.78, 130.74, 129.68, 129.42, 128.93, 128.54, 128.53, 128.52, 127.68, 127.45, 127.37, 127.00, 126.95, 126.63, 126.30, 126.24, 126.20, 125.98, 123.90, 123.25, 120.35, 119.84, 110.51, 110.28 |
| Compound 9 | 8.83 (d, J = 6.83 Hz, 2 H), 8.64 (s, 1 H), 8.54 (d, J = 7.81 Hz, 2 H), 8.35 (d, J = 7.57 Hz, 1 H), 8.27-8.22 (m, 3 H), 8.14 (dd, J = 13.91, 5.86 Hz, 2 H), 8.05 (d, J = 7.08 Hz, 1 H), 7.85 (d, J = 7.81 Hz, 2 H), 7.72 (dd, J = 20.75, 7.08 Hz, 2 H), 7.66 (d, J = 8.06 Hz, 1 H), 7.36-7.44 (m, 5 H), 7.51-7.63 (m, 5 H), 7.31-7.35 (m, 2 H), 7.12 (d, J = 7.81 Hz, 2 H) | 164.70, 164.54, 164.50, 157.21, 156.74, 142.86, 142.20, 140.51, 138.06, 136.90, 136.71, 133.93, 132.83, 131.24, 130.82, 130.77, 128.548, 128.551, 128.04, 127.47, 127.02, 126.96, 126.71, 126.64, 126.31, 125.98, 123.92, 123.74, 123.264, 123.260, 123.08, 121.96, 121.17, 120.92, 120.35, 119.85, 111.96, 110.70, 110.46, 110.28 |

TABLE 2

| | HRMS | | HRMS |
|---|---|---|---|
| Compound 1 | C$_{50}$H$_{34}$N$_3$ M + H, cal: 676.2753 exp: 676.2748 | Compound 2 | C$_{56}$H$_{38}$N$_3$ M + H, cal: 752.3066 exp: 752.3061 |
| Compound 3 | C$_{62}$H$_{42}$N$_3$ M + H, cal: 828.3379 exp: 828.3374 | Compound 4 | C$_{62}$H$_{42}$N$_3$ M + H, cal: 828.3379 exp: 828.3372 |
| Compound 5 | C$_{54}$H$_{36}$N$_3$ M + H, cal: 726.2909 exp: 726.2903 | Compound 6 | C$_{54}$H$_{36}$N$_3$ M + H, cal: 726.2909 exp: 726.2902 |
| Compound 7 | C$_{58}$H$_{38}$N$_3$ M + H, cal: 776.3066 exp: 776.3061 | Compound 8 | C$_{50}$H$_{34}$N$_3$ M + H, cal: 676.2753 exp: 676.2740 |
| Compound 9 | C$_{50}$H$_{32}$N$_{30}$ M + H, cal: 690.2545 exp: 690.2539 | | |

TABLE 3

| | HOMO | LUMO | Band gap | T1 |
|---|---|---|---|---|
| Compound 1 | 5.66 | 2.52 | 3.14 | 2.17 |
| Compound 2 | 5.82 | 2.65 | 3.17 | 2.12 |
| Compound 3 | 5.75 | 2.61 | 3.14 | 2.10 |
| Compound 4 | 5.86 | 2.70 | 3.16 | 2.11 |
| Compound 5 | 5.69 | 2.56 | 3.13 | 2.10 |
| Compound 6 | 5.71 | 2.59 | 3.12 | 2.10 |
| Compound 7 | 5.70 | 2.59 | 3.11 | 2.22 |
| Compound 8 | 5.76 | 2.55 | 3.21 | 2.21 |
| Compound 9 | 5.72 | 2.63 | 3.09 | 2.17 |

Specifically, the physical properties shown in Tables 1 to 3 were measured using a RIKEN Surface analyzer model AC-2, the UV-vis spectra were measured using a Cary 8454 UV-Vis Diode Array system, and the Photoluminescence (PL) spectroscopy was performed using a PerkinElmer LS55 Luminescence Spectrometer. The above physical properties were measured by a METTLER TOLEDO DSC-1 and a METTLER TOLEDO TGA-1, the $^1$H and $^{13}$C NMR was performed using a Varian UNITY INOVA 500 spectrometer, and the HRMS was performed using a ThermoFisher Scientific LTQ Orbitrap XL.

Above measurements were performed using an Agilent 1200 series High Performance Liquid Chromatography (HPLC) system.

EXAMPLES

Example 1

A substrate for use in manufacturing a device was ultrasonically cleaned with distilled water for 10 minutes, dried in an oven at 100° C. for 30 minutes, then transferred to a vacuum deposition chamber.

The substrate used in the Examples was a top emission type, and an anode was formed with a metal/indium tin oxide (ITO) layer. Here, silver (Ag) was used as the metal, and the indium tin oxide (ITO) had a thickness of 10 nm. On the ITO electrode, a hole injection layer (HIL), a hole transport layer (HTL), an electron blocking layer (EBL), an organic emitting layer, an electron transport layer (ETL), and an electron injection layer (EIL) were deposited sequentially.

Specifically, the HIL was deposited to a thickness of 5 nm. The HTL was then deposited on the HIL to a thickness of 120 nm. Next, the EBL was deposited on the deposited HTL to a thickness of 15 nm. Subsequently, a BH compound was deposited to a thickness of 20 nm as an organic emitting layer, and 5 wt % of a BD compound was added to provide impurities. In addition, Compound 1 synthesized in Preparation Example 1 and lithium quinolate (LiQ) were mixed at a weight ratio of 2:1 and deposited on the organic emitting layer at a thickness of 30 nm to form the ETL. Further, the EIL was deposited to a thickness of 1 nm using LiF.

During the above processes, the deposition rate of the organic material layers was maintained at a speed of 0.5 to 1.0 Å/sec, and the degree of vacuum at the time of deposition was maintained at 1 to 4×10$^{-7}$ torr.

Further, in order to maximize the resonance effect, a semi-transparent electrode (cathode) was applied on the ETL, wherein the semi-transparent electrode was formed of a magnesium (Mg)-silver (Ag) alloy at a thickness of 14 nm.

Lastly, a light-efficiency improvement layer (capping layer) was deposited to a thickness of 63 nm. Further, after vacuum deposition, the substrate was transferred to a glove box and subjected to a sealing process. The sealing member was a glass cap provided with a getter inside. The compounds used at the time of deposition for each layer are as follows.

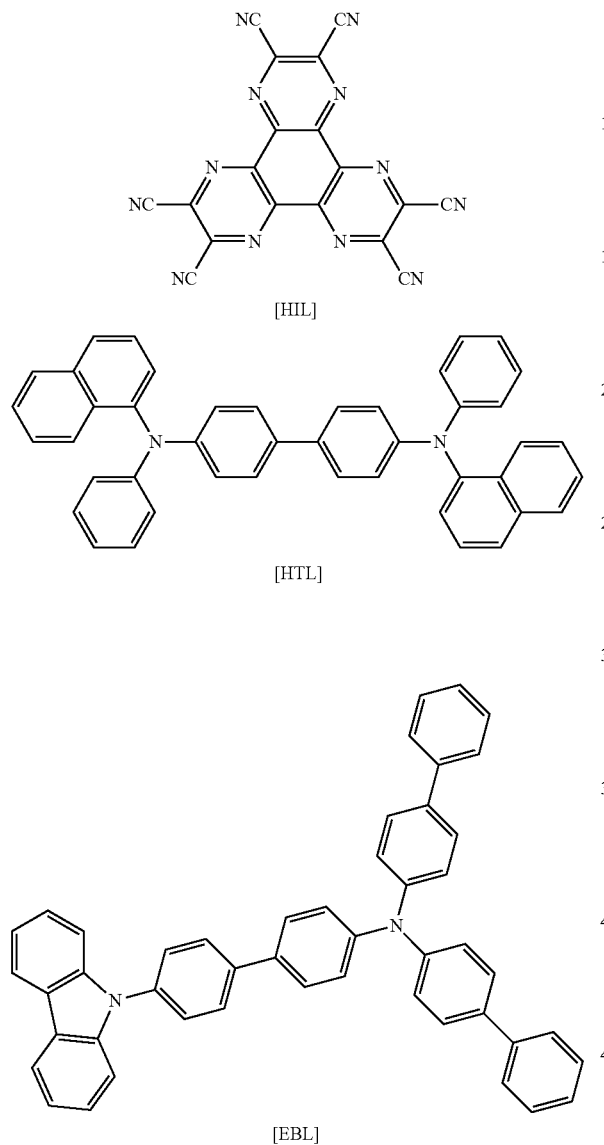

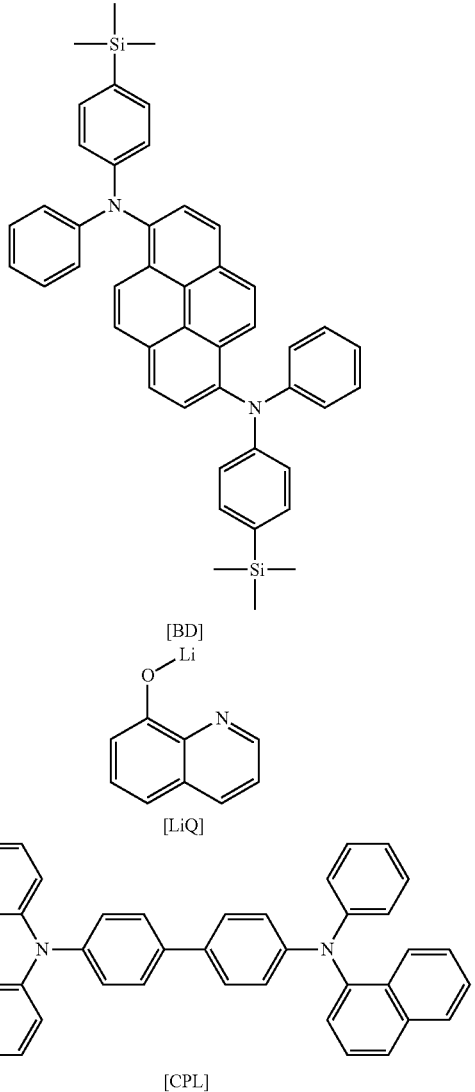

Example 2

Example 2 was performed in the same manner as in Example 1 except that Compound 2 was used instead of Compound 1.

Example 3

Example 3 was performed in the same manner as in Example 1 except that Compound 3 was used instead of Compound 1.

Example 4

Example 4 was performed in the same manner as in Example 1 except that Compound 4 was used instead of Compound 1.

Example 5

Example 5 was performed in the same manner as in Example 1 except that Compound 5 was used instead of Compound 1.

Example 6

Example 6 was performed in the same manner as in Example 1 except that Compound 6 was used instead of Compound 1.

Example 7

Example 7 was performed in the same manner as in Example 1 except that Compound 7 was used instead of Compound 1.

Example 8

Example 8 was performed in the same manner as in Example 1 except that Compound 8 was used instead of Compound 1.

Example 9

Example 9 was performed in the same manner as in Example 1 except that Compound 9 was used instead of Compound 1.

Comparative Example 1

Comparative Example 1 was performed in the same manner as in Example 1 except that ET1 was used instead of Compound 1.

[ET1] Chemical Formula

Comparative Example 2

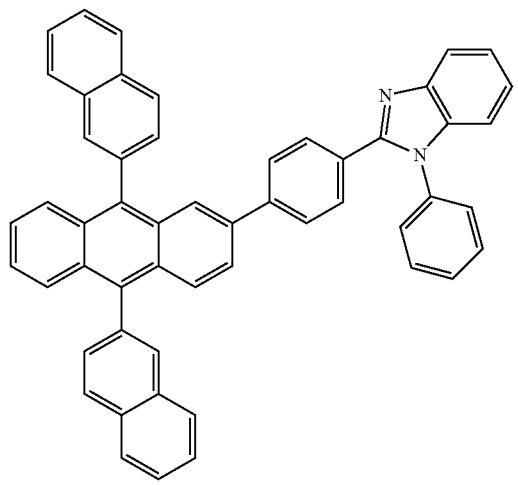

Comparative Example 2 was performed in the same manner as in Example 1 except that ET2 was used instead of Compound 1.

Comparative Example 3

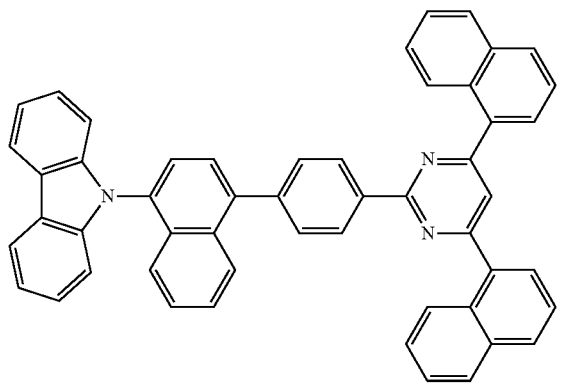

Comparative Example 3 was performed in the same manner as in Example 1 except that ET3 was used instead of Compound 1.

[ET3] Chemical Formula

Comparative Example 4

Comparative Example 4 was performed in the same manner as in Example 1 except that ET4 was used instead of Compound 1.

Comparative Example 5

[ET5] Chemical Formula

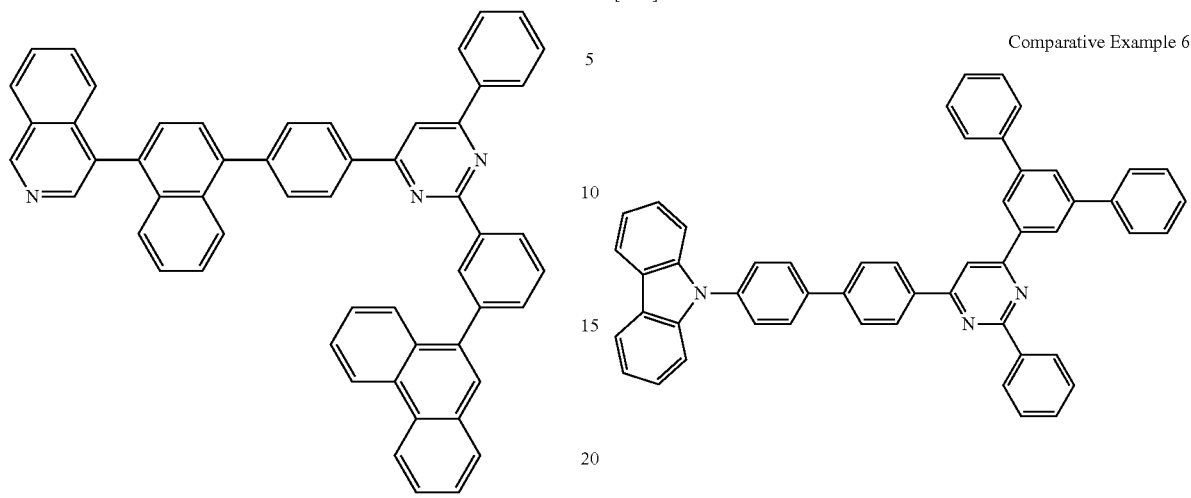

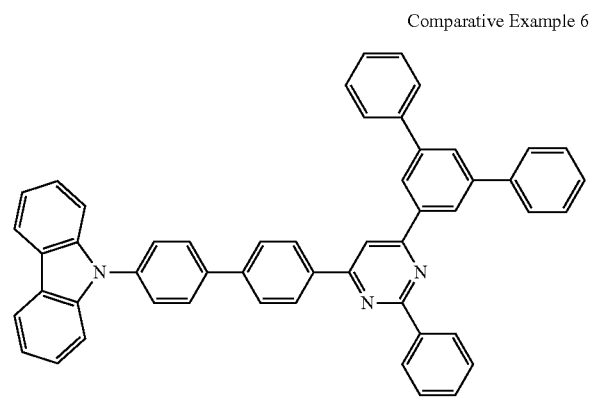

Comparative Example 5 was performed in the same manner as in Example 1 except that ET5 was used instead of Compound 1.

Comparative Example 6 was performed in the same manner as in Example 1 except that ET6 was used instead of Compound 1.

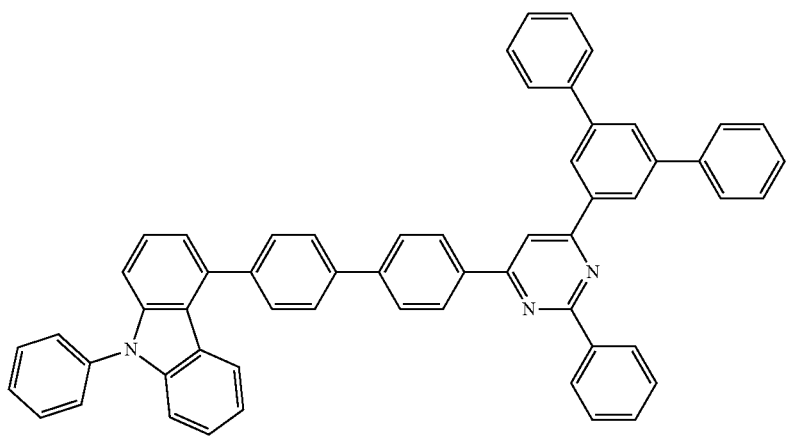

Comparative Example 7 was performed in the same manner as in Example 1 except that ET7 was used instead of Compound 1.

[ET7] Chemical Formula

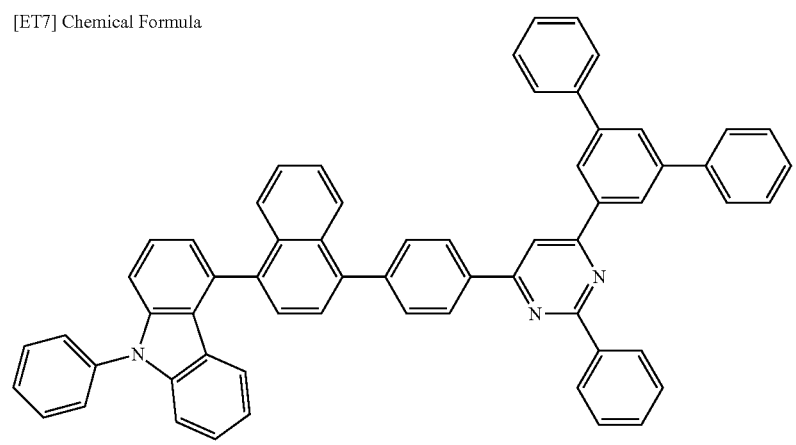

Experimental Examples

For the organic light emitting devices produced in the Examples and Comparative Examples, the driving voltage and luminous efficiency were measured at a current density of 10 mA/cm$^2$, along with the time required to reach 95% luminance (LT95) from an initial luminance of 1,000 cd/m$^2$. The results of measurement are shown in Table 4.

TABLE 4

| | Compound | Driving Voltage (V) | Luminous Efficiency (cd/A) | LT95 at 1000 cd/m$^2$ (time) |
|---|---|---|---|---|
| Experimental Example 1 | 1 | 3.91 | 8.20 | 183 |
| Experimental Example 2 | 2 | 3.98 | 8.18 | 203 |
| Experimental Example 3 | 3 | 4.06 | 8.15 | 192 |
| Experimental Example 4 | 4 | 4.02 | 8.13 | 183 |
| Experimental Example 5 | 5 | 3.92 | 8.16 | 212 |
| Experimental Example 6 | 6 | 3.95 | 8.12 | 219 |
| Experimental Example 7 | 7 | 4.00 | 8.08 | 224 |
| Experimental Example 8 | 8 | 4.03 | 8.22 | 198 |
| Experimental Example 9 | 9 | 4.08 | 8.11 | 226 |
| Comparative Example 1 | ET1 | 4.57 | 6.84 | 102 |
| Comparative Example 2 | ET2 | 4.21 | 7.56 | 156 |
| Comparative Example 3 | ET3 | 4.20 | 7.73 | 113 |
| Comparative Example 4 | E14 | 4.27 | 7.41 | 87 |
| Comparative Example 5 | E15 | 4.12 | 7.98 | 165 |
| Comparative Example 6 | E16 | 4.78 | 7.12 | 170 |
| Comparative Example 7 | ET7 | 4.84 | 7.01 | 181 |

As shown in Table 4, it could be confirmed that the organic light emitting devices (Examples 1 to 9) manufactured using the compounds of the present disclosure as a material for an electron transport layer exhibited excellent characteristics in view of luminous efficiency and stability as compared with the cases employing the materials of Comparative Examples 1 to 7.

The compounds of the present disclosure may be used as the hole injection material, the hole transport material, the host material, the electron injection material or the electron transport material of an organic light emitting device. In addition, the compounds possess excellent electron transport performance, hole or exciton blocking performance, and electron injection performance, which is significantly suitable as a material for organic light emitting devices.

Further, the organic light emitting devices comprising the compound has excellent electrochemical and thermal stability, thereby achieve excellent lifetime characteristics and high luminous efficiency even at a low driving voltage.

While preferable embodiments of the present disclosure are described as above, the present disclosure is not limited to these embodiments, and various modifications can be made within the scope of the appended claims and the detailed description of the present disclosure, which are also included in the scope of the present disclosure.

What is claimed is:

1. A compound comprising:
one or more selected from the group consisting of the following Chemical Formulas 1 to 9:

[Chemical Formula 1]

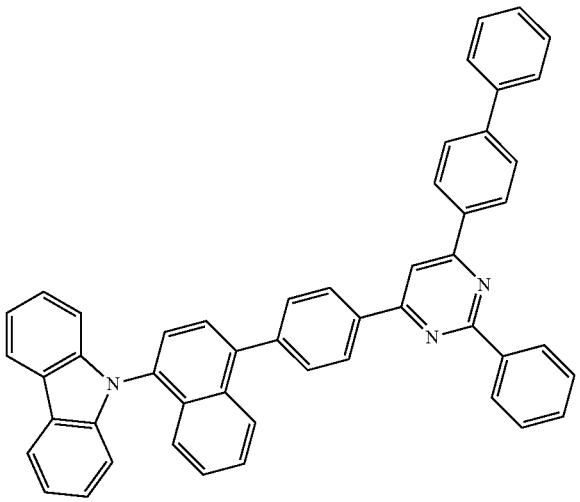

[Chemical Formula 2]

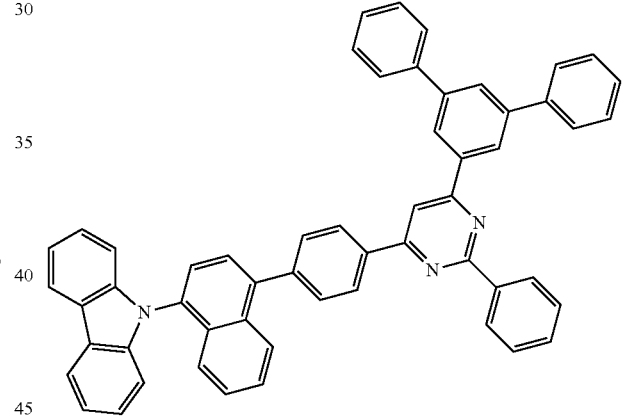

[Chemical Formula 3]

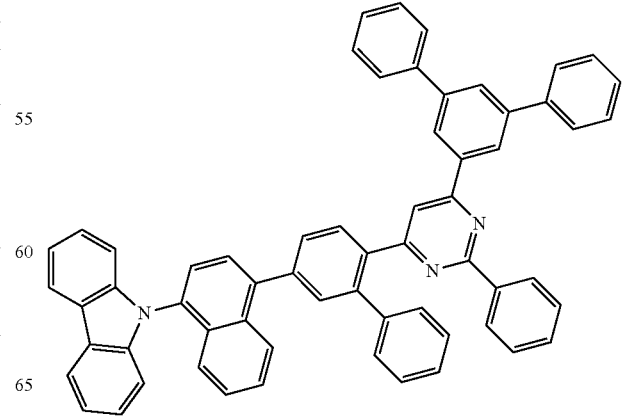

[Chemical Formula 4]
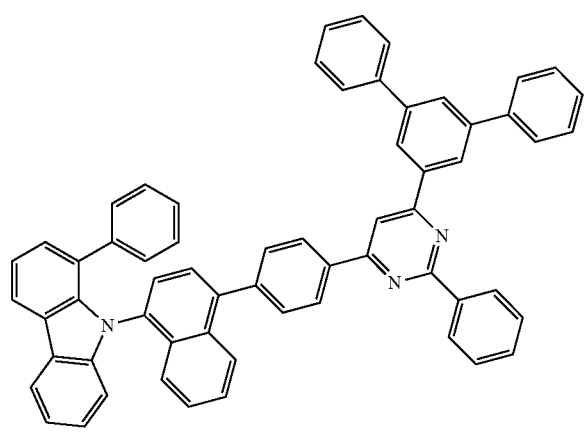
[Chemical Formula 5]
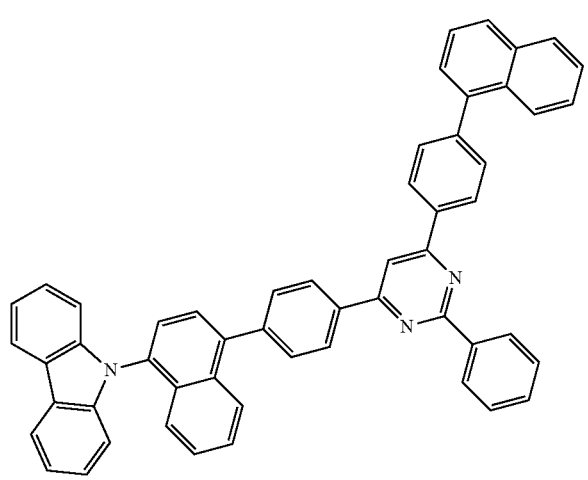
[Chemical Formula 6]
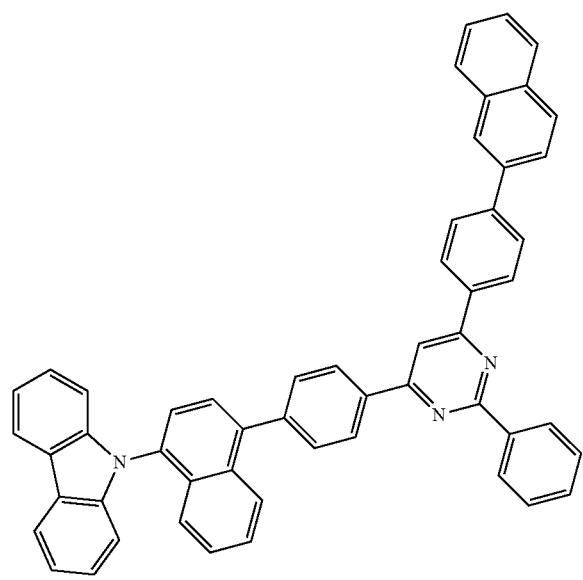
[Chemical Formula 7]
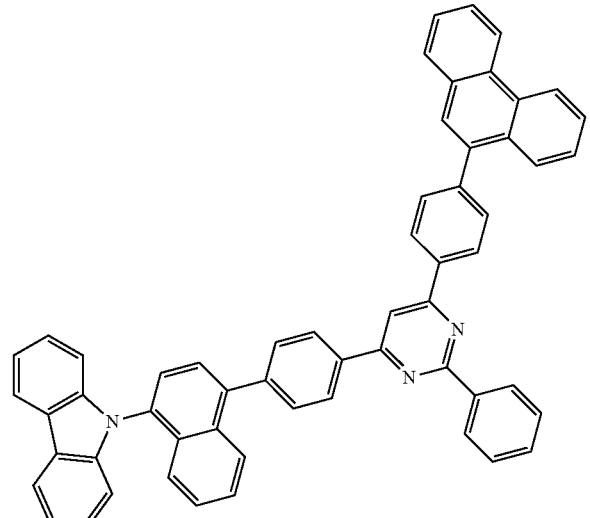
[Chemical Formula 8]
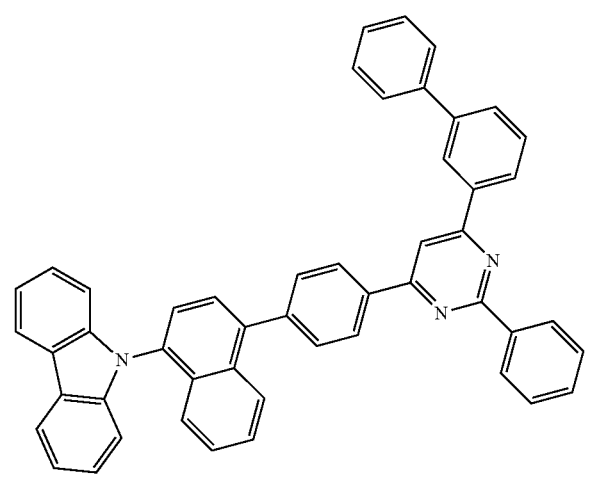
[Chemical Formula 9]
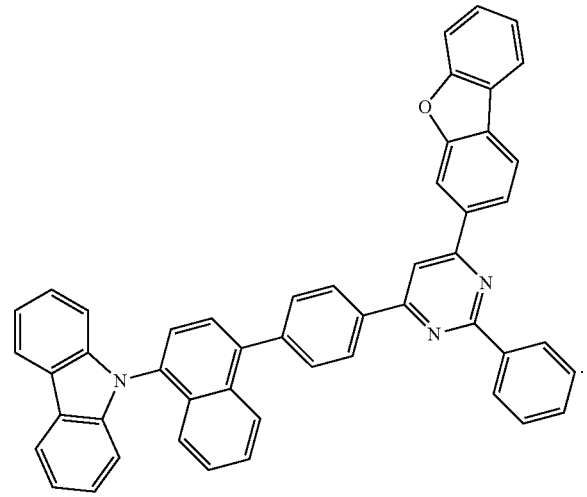
2. A material for an organic light emitting device comprising the compound of claim 1.
3. The material for an organic light emitting device of claim 2, wherein the material is used as one or more selected from the group consisting of a hole transport material, an electron injection material, an electron transport material, and a host material of a light emitting layer.

4. An organic light emitting device comprising the compound of claim 1.

5. The organic light emitting device of claim 4, wherein the organic light emitting device includes a first electrode, a second electrode, and one or more organic material layers provided between the first electrode and the second electrode, and the one or more organic material layers include the compound.

6. The organic light emitting device of claim 5, wherein the one or more organic material layers include at least one layer from among a hole transport layer, a light emitting layer, and an electron transport layer.

7. The organic light emitting device of claim 5, wherein the one or more organic material layers include an electron transport layer.

8. The organic light emitting device of claim 7, wherein the compound is used as an electron transport material.

9. An electronic equipment including the organic light emitting device of claim 4.

\* \* \* \* \*